(12) United States Patent
Amirouche et al.

(10) Patent No.: US 8,790,307 B2
(45) Date of Patent: *Jul. 29, 2014

(54) DRUG DELIVERY DEVICE AND METHODS THEREFOR

(75) Inventors: Farid Amirouche, Highland Park, IL (US); Arash N. Attar, Chicago, IL (US); Matthew L. Cantwell, Northbrook, IL (US)

(73) Assignee: Picolife Technologies, LLC, Deerfield, IL (US)

( * ) Notice: Subject to any disclaimer, the term of this patent is extended or adjusted under 35 U.S.C. 154(b) by 8 days.

This patent is subject to a terminal disclaimer.

(21) Appl. No.: 13/370,091

(22) Filed: Feb. 9, 2012

(65) Prior Publication Data

US 2013/0144254 A1 Jun. 6, 2013

Related U.S. Application Data

(63) Continuation-in-part of application No. 13/308,899, filed on Dec. 1, 2011.

(51) Int. Cl.
*A61M 1/00* (2006.01)

(52) U.S. Cl.
USPC .............. 604/151; 604/66; 604/500; 604/504

(58) Field of Classification Search
USPC ........... 604/131–132, 151–153, 66, 500, 504; 417/477.2
See application file for complete search history.

(56) References Cited

U.S. PATENT DOCUMENTS

| | | | |
|---|---|---|---|
| 2,398,435 A | 4/1946 | Marks | |
| 3,137,242 A | 6/1964 | Hahn | |
| 3,498,228 A | 3/1970 | Blumle et al. | |
| 3,691,263 A | 9/1972 | Stoy et al. | |
| 3,771,694 A | 11/1973 | Kaminski | |
| 3,827,565 A | 8/1974 | Matsumura | |
| 3,889,710 A | 6/1975 | Brost | |
| 3,915,609 A | 10/1975 | Robinson | |
| 4,017,238 A | 4/1977 | Robinson | |
| 4,197,266 A | 4/1980 | Clark et al. | |

(Continued)

FOREIGN PATENT DOCUMENTS

| | | |
|---|---|---|
| EP | 0 024 431 B1 | 8/1985 |
| EP | 0 299 628 A1 | 1/1989 |

(Continued)

OTHER PUBLICATIONS

"Bartels micropumps," Apr. 2009, [online] http://www.bartelsmikrotechnik.de/index.php/micropumps.html.

(Continued)

*Primary Examiner* — Theodore Stigell

(74) *Attorney, Agent, or Firm* — Finnegan, Henderson, Farabow, Garrett & Dunner, LLP

(57) ABSTRACT

A drug delivery device for delivery of medicament having a delivery pump system and a cartridge system, the delivery pump system operating electromagnetically by driving two disk magnets that are housed within pump body inserts of the cartridge system. The displacement of the magnets and an elastomer membrane placed between the magnets of the cartridge system results in a volumetric change within two reservoirs and the flow of medicaments. The medicament flows from the reservoirs to the inlet/outlet members via the pump body inserts and discharged to a patient user's body through an infusion set.

23 Claims, 63 Drawing Sheets

(56) References Cited

U.S. PATENT DOCUMENTS

| | | | |
|---|---|---|---|
| 4,257,416 A | 3/1981 | Prager | |
| 4,340,048 A | 7/1982 | Eckenhoff | |
| 4,376,618 A * | 3/1983 | Toyoda et al. | 417/417 |
| 4,415,003 A | 11/1983 | Paradis et al. | |
| 4,498,843 A | 2/1985 | Schneider et al. | |
| 4,544,369 A | 10/1985 | Skakoon et al. | |
| 4,552,561 A | 11/1985 | Eckenhoff et al. | |
| 4,657,486 A | 4/1987 | Stempfle et al. | |
| 4,712,583 A | 12/1987 | Pelmulder et al. | |
| 4,731,726 A | 3/1988 | Allen, III | |
| 4,784,644 A | 11/1988 | Sawyer et al. | |
| 4,797,144 A | 1/1989 | DeMeritt et al. | |
| 4,840,754 A | 6/1989 | Morgan | |
| 4,936,833 A | 6/1990 | Sams | |
| 4,938,742 A | 7/1990 | Smits | |
| 4,946,448 A | 8/1990 | Richmond | |
| 4,947,856 A | 8/1990 | Beard | |
| 4,958,661 A | 9/1990 | Holtermann et al. | |
| 4,966,199 A | 10/1990 | Ruschke | |
| 5,019,974 A | 5/1991 | Beckers | |
| 5,050,612 A | 9/1991 | Matsumura | |
| 5,147,323 A | 9/1992 | Haber et al. | |
| 5,218,993 A | 6/1993 | Steinberg et al. | |
| 5,246,634 A | 9/1993 | Ichikawa et al. | |
| 5,370,635 A | 12/1994 | Strausak et al. | |
| 5,584,815 A | 12/1996 | Pawelka et al. | |
| 5,645,855 A | 7/1997 | Lorenz | |
| 5,674,557 A | 10/1997 | Wildman et al. | |
| 5,709,662 A | 1/1998 | Olive et al. | |
| 5,762,632 A | 6/1998 | Whisson | |
| 5,775,671 A | 7/1998 | Cote, Sr. | |
| 5,822,715 A | 10/1998 | Worthington et al. | |
| 5,858,001 A | 1/1999 | Tsals et al. | |
| 6,003,736 A | 12/1999 | Ljunggren | |
| 6,017,331 A | 1/2000 | Watts et al. | |
| 6,056,718 A | 5/2000 | Funderburk et al. | |
| 6,305,661 B1 | 10/2001 | Kennedy | |
| 6,311,712 B1 | 11/2001 | Meyer | |
| 6,315,929 B1 | 11/2001 | Ishihara et al. | |
| 6,390,120 B1 | 5/2002 | Guala | |
| 6,409,707 B1 | 6/2002 | Guala | |
| 6,572,586 B1 | 6/2003 | Wojcik | |
| 6,627,124 B1 | 9/2003 | Herbrechtsmeier et al. | |
| 6,648,859 B2 | 11/2003 | Bitdinger et al. | |
| 6,723,086 B2 | 4/2004 | Bassuk et al. | |
| 6,813,906 B1 | 11/2004 | Hirota et al. | |
| 6,945,963 B2 | 9/2005 | Langley et al. | |
| 7,044,125 B2 | 5/2006 | Vedrine et al. | |
| 7,081,108 B2 | 7/2006 | Langley et al. | |
| 7,104,973 B2 | 9/2006 | Woolston et al. | |
| 7,123,985 B2 | 10/2006 | Wildsmith et al. | |
| 7,296,782 B2 | 11/2007 | Enerson et al. | |
| 7,302,311 B2 | 11/2007 | Varis | |
| 7,407,490 B2 | 8/2008 | Bendsen et al. | |
| 7,470,266 B2 | 12/2008 | Massengale et al. | |
| 7,510,544 B2 | 3/2009 | Vilks et al. | |
| 7,537,590 B2 | 5/2009 | Santini, Jr. et al. | |
| 7,585,167 B2 | 9/2009 | Lawton et al. | |
| 7,637,899 B2 | 12/2009 | Woolston et al. | |
| 7,846,146 B2 | 12/2010 | Woolston et al. | |
| 7,850,663 B2 | 12/2010 | Sullivan et al. | |
| 7,896,002 B2 | 3/2011 | Watanabe | |
| 7,914,499 B2 | 3/2011 | Gonnelli et al. | |
| 7,935,280 B2 | 5/2011 | Lawton et al. | |
| 7,967,795 B1 | 6/2011 | Cabiri | |
| 8,021,334 B2 | 9/2011 | Shekalim | |
| 2002/0119711 A1 | 8/2002 | VanAntwerp et al. | |
| 2003/0100883 A1 | 5/2003 | Kristensen et al. | |
| 2003/0180164 A1 | 9/2003 | Bunner et al. | |
| 2004/0050104 A1 | 3/2004 | Ghosh et al. | |
| 2004/0176727 A1 | 9/2004 | Shekalim | |
| 2005/0065500 A1 | 3/2005 | Couvillon, Jr. et al. | |
| 2005/0192557 A1 | 9/2005 | Brauker et al. | |
| 2006/0021386 A1 | 2/2006 | Wang | |
| 2006/0073232 A1 | 4/2006 | Wang | |
| 2006/0145372 A1 | 7/2006 | Jones et al. | |
| 2007/0073230 A1 | 3/2007 | Jasperson et al. | |
| 2007/0087068 A1 | 4/2007 | Eiha et al. | |
| 2007/0225147 A1 | 9/2007 | Hayashi et al. | |
| 2007/0233008 A1 | 10/2007 | Kristensen et al. | |
| 2007/0299398 A1 | 12/2007 | Alferness et al. | |
| 2008/0169444 A1 | 7/2008 | Guala | |
| 2009/0062767 A1 | 3/2009 | Van Antwerp et al. | |
| 2009/0105658 A1 | 4/2009 | Jennewine | |
| 2010/0004603 A1 | 1/2010 | Kristensen et al. | |
| 2010/0081993 A1 | 4/2010 | O'Connor | |
| 2010/0185322 A1 | 7/2010 | Bylsma et al. | |
| 2010/0225013 A1 | 9/2010 | Eiha et al. | |
| 2010/0255366 A1 | 10/2010 | Myland | |
| 2010/0280461 A1 | 11/2010 | Forstreuter | |
| 2010/0317093 A1 | 12/2010 | Turewicz et al. | |
| 2011/0021905 A1 | 1/2011 | Patrick et al. | |
| 2011/0066131 A1 | 3/2011 | Cabiri | |
| 2011/0114744 A1 | 5/2011 | Ricciardi et al. | |
| 2011/0118675 A1 | 5/2011 | Miller et al. | |
| 2011/0137287 A1 | 6/2011 | Gonnelli et al. | |
| 2011/0168294 A1 | 7/2011 | Jakobsen et al. | |
| 2011/0251546 A1 | 10/2011 | Sullivan et al. | |
| 2011/0274566 A1 | 11/2011 | Amirouche et al. | |
| 2011/0308650 A1 | 12/2011 | Amirouche et al. | |
| 2011/0309229 A1 | 12/2011 | Amirouche et al. | |
| 2011/0309552 A1 | 12/2011 | Amirouche et al. | |
| 2012/0002422 A1 | 1/2012 | Lia et al. | |
| 2012/0053571 A1 | 3/2012 | Petri | |
| 2013/0144214 A1 | 6/2013 | Amirouche et al. | |
| 2013/0237947 A1 | 9/2013 | Amirouche et al. | |
| 2013/0274576 A1 | 10/2013 | Amirouche et al. | |
| 2013/0274577 A1 | 10/2013 | Amirouche et al. | |
| 2013/0345650 A1 | 12/2013 | Amirouche | |

FOREIGN PATENT DOCUMENTS

| | | |
|---|---|---|
| GB | 2 248 891 A | 4/1992 |
| JP | 62-297120 A | 12/1987 |
| JP | 2007-015906 A | 1/2007 |
| JP | 2007-0119280 A | 5/2007 |
| JP | 2008-96089 A | 4/2008 |
| WO | WO 03/047426 A1 | 6/2003 |
| WO | WO 2004/067964 A | 8/2004 |
| WO | WO 2006/111775 A | 10/2006 |
| WO | WO 2007/055642 A1 | 5/2007 |
| WO | WO 2009/048462 A1 | 4/2009 |
| WO | WO 2010/128914 A1 | 11/2010 |

OTHER PUBLICATIONS

"Diabetes Basics: Diabetes Statistics," American Diabetes Association, [Online]. Available at: http://www.diabetes.org/diabetes-basics/. [Accessed May 14, 2012] (3 pages).

"Diabetic Neuropathy, Living With Numbness and Pain," A Diabetic Life, [Online]. Available at: http://www.a-diabetic-life.com/diabetic-neuropathy.html. [Accessed May 5, 2012] (3 pages).

"Electromyogram (EMG)," MedicineNet.com, [Online]. Available at: http://www.medicinenet.com/electromyogram/article.htm. [Accessed May 15, 2012] (3 pages).

"Nerve conduction velocity," MedlinePlus®, A Service of the U.S. National Library of Medicine, National Institutes of Health, [Online]. Available at: http://www.nlm.nih.gov/medlineplus/ency/article/003927.htm; updated Jun. 18, 2011 (3 pages).

"Peripheral Neuropathy Fact Sheet," National Institute of Neurological Disorders and Stroke, NIH Publication No. 04-4853, [Online]. Available: http://www.ninds.nih.gov/disorders/peripheralneuropathy/detail_peripheralneuropathy.htm; updated Sep. 19, 2012 (9 pages).

"Peripheral Neuropathy Market Approaches US$1B by 2012," PR Newswire, United Business Media [Online]. Available at: http://www.prnewswire.co.uk/news-releases/peripheral-neuropathymarket-approaches-us1b-by-2012-154534705.html, Apr. 7, 2012 (2 pages).

"*Silasic*® BioMedical Grade ETR elastomers", Dow Corning, 2002-2011, accessed at http://www4.dowcorning.com/DataFiles/090007c88028669a.pdf (5 pages).

(56) References Cited

OTHER PUBLICATIONS

"Silastic © Biomedical Grade Liquid Silicone Rubbers", Dow Corning, 2006, accessed at http://www4.dowcorning.com/DataFiles/090007c880097f96.pdf (6 pages).
"Small, powerful, light, precise: micro diaphragm pumps made of plastics: thinXXS micropumps" Mar. 2009, [online] http://www.thinxxs.com/main/produkte/micropumps.html (2 pages).
"*Sylgard®* 184 Silicone Elastomer", Dow Corning, 2007, accessed at http://ncnc.engineering.ucdavis.edu/pages/equipment/Sylgard_184_data_sheet.pdf (3 pages).
Acevedo, "Creation of Dual Chamber Micropump Using Rapid Prototyping," Milwaukee School of Engineering, Research Experience for Undergraduates Paper, 2005. Available online at: http://www/msae.edu/academics/research_centers/reu/pdf/2005/Creation%20of%20a%20Dual%20Chamber%20Micropump%20using%20Rapid%20Prototyping.pdf (6 pages).
Amirouche et al., "Current Micropump Technologies and Their Biomedical Applications," Microsystem Technology, 2009, pp. 647-666, vol. 15.
Anhalt et al., "Insulin Patch Pumps: Their Development and Future in Closed-Loop Systems," *Diabetes Technology & Therapeutics*, 2010, pp. 51-58, vol. 12.
Bak et al., "Multiple Insulin Injections Using a Pen Injector Versus Insulin Pump Treatment in Young Diabetic Patients," Diabetes Research, 1987, pp. 155-158, vol. 6.
Barbano et al., "Effectiveness, Tolerability, and Impact on Quality of Life of the 5% Lidocaine Patch in Diabetic Polyneuropathy," Archives of Neurology, 2004, pp. 914-918, vol. 61, No. 6.
Bohm et al., "A plastic micropump constructed with conventional techniques and materials," Sensors and Actuators A, vol. 77-3, pp. 223-228, 1999.
Casella et al., "Accuracy and Precision of Low-Dose Insulin Administration," Pediatrics, 1993, pp. 1155-1157, vol. 91.
Dario et al., "A fluid handling system for a chemical microanalyzer," J. Micromech. Microeng., vol. 6, pp. 95-98, 1996.
Davis et al., "Techniques for Improved Soft Lens Fitting"; Aug. 1, 2005, p. 2, accessed at http://www.cispectrum.com/articleviewer.aspx?articleid=12852 (5 pages).
Einhorn et al., "Advances in Diabetes for the Millennium: Insulin Treatment and Glucose Monitoring," Medscape General Medicine, 2004, p. 8, vol. 6, (3 Suppl.) [Online]. Available at: http://www.medscape.org/viewarticle/488996 (9 pages).
Elleri et al., "Closed-Loop Insulin Delivery for Treatment of Type 1 Diabetes," BMC Medical, 2011, p. 120, vol. 9 [Online]. Available at: http://www.biomedcentral.com/1741-7015/9/120 (9 pages).
Farnbach, "Peripheral Nerve Testing and Electromyography," [Online]. Available at: http://cal.vet.upenn.edu/projects/saortho/appendix_d/appd.htm. [Accessed May 18, 2012] (10 pages).
Fu et al. "TiNi-based thin films in MEMS applications: a review," Sensors and Actuators A, 2004, pp. 395-408, vol. 112, No. 23.
Galer et al. "The Lidocaine Patch 5% Effectively Treats All Neuropathic Pain Qualities: Results of a Randomized, Double-Blind, Vehicle-Controlled, 3-Week Efficacy Study with Use of the Neuropathic Pain Scale," The Clinical Journal of Pain, 2002, pp. 297-301, vol. 18, No. 5 (Abstract).
Gammaitoni et al., "Pharmacokinetics and Tolerability of Lidocaine Patch 5% with Extended Dosing," The Annals of Pharmacotherapy, 2002, pp. 236-240, vol. 36, No. 2, (Abstract).
Ha et al., "Disposable thermo-pneumatic micropump for bio lab-on-a-chip application," Microelectronic Engineering, 2009, pp. 1337-1339, vol. 86.
Ignaut et al., "Comparative Device Assessments: Humalog KwikPen Compared with Vial and Syringe and FlexPen," The Diabetes Educator, 2009, pp. 789-798, vol. 35, No. 2.
International Search Report and Written Opinion issued in International Patent Application No. PCT/US2009/059020, mailed Mar. 9, 2010 (17 pages).
International Search Report and Written Opinion issued in International Patent Application No. PCT/US2012/066937, mailed Mar. 7, 2013 (7 pages).
International Search Report and Written Opinion issued in International Patent Application No. PCT/US2013/035918, mailed Jun. 21, 2013 (9 pages).
International Search Report and Written Opinion issued in International Patent Application No. PCT/US2013/035921, mailed Jul. 1, 2013 (11 pages).
International Search Report and Written Opinion issued in International Patent Application No. PCT/US2013/046546, mailed Aug. 8, 2013 (11 pages).
Irawan et al., "Fabrication and performance testing of disposable micropump suitable for microfluidic chip," in Intl. Conf. on Biomedical and Pharmaceutical Engineering, Orchard Hotel, Singapore, Dec. 2006, pp. 252-255.
Jeong, et al., "Fabrication of a peristaltic PDMS micropump," Sensors and Actuators A, vol. 123-124, pp. 453-458, 2005.
Junwu et al., "Design and test of a high-performance piezoelectric micropump for drug delivery," Sensors and Actuators A, vol. 121, pp. 156-161, 2005.
Klonoff et al., "Insulin Pump Safety Meeting: Summary Report," Journal of Diabetes Science and Technology, 2009, pp. 396-402, vol. 3, No. 2.
Koch, et al., "PDMS and tubing-based peristaltic micropumps with direct actuation," Sensors and Actuators B, vol. 135, pp. 664-670, 2009.
Laser et al., "A review of micropumps," J. Micromech. Microeng., vol. 14(6), pp. R35-R64, 2004.
Lee et al., "Microfluidic mixing: A review," Int. J. Mol. Sci., 2011, pp. 3263-3287, vol. 12.
Li et al., "A high frequency high flow rate piezoelectronically driven MEMS micropump" in Proceedings IEEE Solid State Sensors and Actuators Workshop, Hilton Head, SC, Jun. 2000 (4 pages).
Ma et al., "Development and application of a diaphragm micro-pump with piezoelectric device," Microsyst. Technol., vol. 14, pp. 1001-1007, 2008.
Manz, et al., "Miniaturized total chemical analysis systems: a novel concept for chemical sensing," Sensors and Actuators B, vol. 1, pp. 244-248, 1990.
Meece et al., "Effect of Insulin Pen Devices on the Management of Diabetes Mellitus," Am J Health-Syst. Pharm., 2008, pp. 1076-1082, vol. 65.
Melin et al., "A fast passive and planar liquid sample micromixer," Lab on a Chip, 2004, pp. 214-219, vol. 4.
Morrow, "Transdermal Patches Are More Than Skin Deep," Managed Care [Online]. Available at: http://www.managedcaremag.com/archives/0404/0404.biotech.html. Apr. 2004 (4 pages).
Mundell, "Antidepressant Cymbalta Might Ease Chemo-Linked Pain," MSN Healthy Living, 2013 [Online]. Available at: http://health.msn.com/health-topics/cancer/antidepressant-cymbalta-might-ease-chemo-linked-pain (4 pages).
Nguyen et al., "MEMS-micropumps: a review," Journal of Fluids Engineering, vol. 124, p. 384-392, 2002.
Nguyen et al., "Microfluidics for Internal Flow Control: Micropumps," in *Fundamentals and Applications of Microfluidics*. Norwood, MA: Artech House, Inc., 2002; pp. 293-341.
Nisar et al., "MEMS-based Micropumps in Drug Delivery and Biomedical Applications," Sensors and Actuators B, 2008, pp. 917-942, vol. 130.
Pallikaris, "Intracorneal mico-lens a minimally invasive option for presbyopia"; Aug. 10, 2010, p. 1, paragraph 003, accessed at http://www.rigneygraphics.com/clients/presbia/website/newsmedia/pdfs/press-osn-presbia.pdf (2 pages).
Pan et al, "A magnetically driven PDMS micropump with ball-check-valves," J. Micromech. Microeng, vol. 15, pp. 1021-1026, 2005.
Rapp et al., "Liga micropump for gases and liquids," Sensors and Actuators A, 1994, pp. 57-61, vol. 40, No. 1.
Richardson et al., "Peripheral Neuropathy: A True Risk Factor for Falls," The Journal of Gerontology: Series A, 1995, pp. 211-215, vol. 50, No. 4 (Abstract).
Roberts, "Blind Attack on Wireless Insulin Pumps Could Deliver Lethal Dose," Threatpost.com, The Kaspersky Lab Security News Service, Oct. 27, 2011 (2 pages).

(56) References Cited

OTHER PUBLICATIONS

Rosielle, "The Lidocaine Patch," Medical College of Wisconsin [Online]. Available: http//:www.eperc.mcw.edu/EPERC/FastFactsIndex/ff_148.htm. [May 15, 2012] (3 pages).

Santra et al., "Fabrication and testing of a magnetically actuated micropump," Sensors and Actuators B, vol. 87, pp. 358-364, 2002.

Selam, "Evolution of Diabetes Insulin Delivery Devices," Journal of Diabetes Science and Technology, 2010, pp. 505-513, vol. 4, No. 3.

Shen et al., "Miniaturized PMMA ball-valve micropump with cylindrical electromagnetic actuator," Microelectronic Engineering, vol. 85, pp. 1104-1107, 2008.

Singhal, et al., "Microscale pumping technologies for microchannel cooling systems," Appl. Mech. Rev., vol. 57(3), pp. 191-221, 2004.

Star Micronics Co. Ltd., "Precision products," Mar. 2009, [online]. Accessed at: http://www.star-m.jp/eng/products/precision/index/html, on Aug. 22, 2011 (4 pages).

Trenkle et al., "Normally-closed peristaltic micropump with re-usable actuator and disposable fluidic chip," Sensors and Actuators B, vol. 154, pp. 137-141, 2011.

Tasi et al., "Review of MEMS-based drug delivery and dosing systems," Sensors and Actuators A, vol. 134, No. 2, pp. 555-564, 2007.

U.S. Appl. No. 13/174,598, filed Jun. 30, 2011, by Amirouche et al.: Non-Final Rejection, dated May 14, 2013.

U.S. Appl. No. 13/174,598, filed Jun. 30, 2011, by Amirouche et al.: Final Rejection, dated Oct. 3, 2013.

U.S. Appl. No. 13/174,624, filed Jun. 30, 2011 by Amirouche et al.: Non-Final Rejection, dated Jun. 28, 2012.

U.S. Appl. No. 13/174,624, filed Jun. 30, 2011 by Amirouche et al.: Final Rejection, dated Nov. 21, 2012.

U.S. Appl. No. 13/174,624, filed Jun. 30, 2011 by Amirouche et al.: Non-Final Rejection, dated Feb. 8, 2013.

U.S. Appl. No. 13/174,624, filed Jun. 30, 2011 by Amirouche et al.: Final Rejection, dated Jul. 31, 2013.

U.S. Appl. No. 13/174,643, filed Jun. 30, 2011 by Amirouche et al.: Non-Final Rejection, dated May 2, 2013.

U.S. Appl. No. 13/174,643, filed Jun. 30, 2011 by Amirouche et al.: Notice of Allowance, dated Oct. 21, 2013.

U.S. Appl. No. 13/308,899, filed Dec. 1, 2011, by Amirouche et al.: Non-Final Rejection, dated Aug. 8, 2013.

U.S. Appl. No. 13/649,202, filed Oct. 11, 2012, by Amirouche: Non-Final Rejection, dated Jun. 18, 2013.

U.S. Appl. No. 13/649,202, filed Oct. 11, 2012, by Amirouche: Final Rejection, dated Jan. 15, 2014.

U.S. Appl. No. 13/692,868, filed Dec. 3, 2012, by Amirouche et al.

Van Lintel, et al., "A piezoelectric micropump based on micromachining of silicon," Sensors and Actuators A, vol. 15, p. 153-167, 1988.

Yadav et al., "Various Non-injectable Delivery Systems for the Treatment of Diabetes Mellitus," Endocrine, Metabolic & Immune Disorders—Drug Targets, 2009, pp. 1-13, vol. 9, No. 1.

Yamahata, et al. "A PMMA valveless micropump using electromagnetic actuation," Microfluidic Nanofluid, vol. 1, pp. 197-207, 2005.

Zhu et al., "Optimization design of multi-material micropump using finite element method," Sensors and Actuators A, vol. 149, pp. 130-135, 2009.

\* cited by examiner

DRUG DELIVERY DEVICE AND METHODS THEREFOR

CROSS-REFERENCE TO RELATED APPLICATIONS

This application is a continuation-in-part of U.S. application Ser. No. 13/308,899 filed on Dec. 1, 2011.

BACKGROUND OF THE INVENTION

1. Field of the Invention

The present invention relates to the field of medical devices and, in particular, to devices for delivery of medicament(s). More particularly, the present invention relates to a drug delivery device for delivery of insulin or other medicament(s), and methods therefor.

2. Description of the Related Art

Diabetes is a disease caused by the body's failure to produce adequate insulin or the cell's failure to respond to insulin resulting in high levels of sugar in the blood. If left untreated, diabetes can cause numerous complications. Typically, treatment for diabetes required both repeated checking of blood glucose levels and several injections of insulin throughout the day. Major drawbacks of such treatment were the need to draw blood and test glucose levels throughout the day, improper or low dosage amounts of insulin, contamination of the insulin delivery system, or lifestyle restriction. Low dosages of insulin over an extended period may cause heart disease, stroke, kidney failure, hypertension, or retinal damage.

Diabetes may be controlled by insulin replacement therapy in which insulin is delivered to the diabetic person, usually by injection, to counteract elevated blood glucose levels. Injectable insulin may be problematic due to the presence of air bubbles in a syringe, possibility of needle contamination, pain and infection. Recent therapies include the basal/bolus method of treatment in which basal, a long acting insulin medication, for example, Humalog® and Apidra®, is delivered via injection once every day. The basal provides the body with a relatively constant dose of insulin throughout the day. At mealtime, an additional dose of insulin, or bolus, is administered based on the amount of carbohydrate and protein in the meal. Accurate calculations of various parameters including the amount of carbohydrates and proteins consumed, and the lapse in time since the last dosage are necessary to determine the appropriate dosage of insulin. The dosages are thus prone to human error and the method is ineffective when doses are skipped, forgotten or miscalculated. Exercise, stress and other factors can also cause the calculations to be inaccurate.

To address these problems, programmable insulin delivery devices or insulin pumps were developed which seek to mimic the way a normal, healthy pancreas delivers insulin to the body. Insulin pumps are programmed to deliver a continual basal dose of insulin and occasionally a bolus dose in response to a patient's meal intake and physical activities. Additionally, the number of times a patient is required to draw blood and test their glucose during the day is reduced, thus lessening the pain and inconvenience of this disease. Also, micro-doses of insulin that can be delivered by programmable insulin delivery devices are more easily tolerated and rapidly metabolized by the body and thus, more effective.

Conventional insulin pumps are worn on the body and are connected to a patient via a cannula that is inserted somewhere on the patient's abdomen. The insulin is delivered under the skin and is absorbed into the body through the subcutaneous fat layer. Insulin pumps in the past have been quite large, some requiring the use of a shoulder bag to transport. Over time, they have become smaller in size and most pumps today are roughly the size of a deck of cards. Currently available insulin pumps include Animas OneTouch® Ping®, Deltec Cozmo®, Disetronic Accu-Chek Spirit®, Insulet OmniPod, Medtronic Paradigm™, Sooil USA Diabecare®II, and Nipro Amigo®.

With the decreased size of the pump unit also comes a decreased size in the medication reservoir. This reduced reservoir size means more frequent refilling, greater potential for contamination of the reservoir, more frequent changes of the cannula and tubing, and greater expense overall in treating the condition. Sooil USA Diabecare®II, Medtronic Paradigm®, Deltec Cozmo®, and Disetronic Accu-Chek Spirit® all require manual filling of the reservoir. The present invention overcomes the disadvantages of the existing systems by utilizing 300 u dual reservoirs prefilled with medicaments, with an option to redesign or re-conform the reservoirs to accommodate larger volumes.

Recent medical data suggests that a combination of insulin and another medication, such as glucagon, infused at different times or simultaneously, leads to better results in patients. An advantage of the dual reservoirs of the present invention is that they can be manufactured to contain two dissimilar medicaments within the same cartridge, for instance, insulin in one reservoir and a different medicament in a second reservoir.

Another disadvantage of many existing devices is the relatively short battery life, from 2-4 weeks for the Animas OneTouch® Ping® to 8-10 weeks for the Sooil USA Diabecare®II. The present invention has a rechargeable battery life of two (2) years, far surpassing all currently available insulin pumps. Yet another disadvantage of many existing insulin pumps is the size of the basal increment dose. The present invention currently allows a basal increment dose in the range of 0 to 0.5 u (in increments of tenths or hundredths of the maximum value of the range) that allows for more flexibility in dosing.

Among the other advantages of the present invention over prior art is the increased memory storage capacity. The present invention can store 5000 past basal and bolus events as well as 5000 past glucose readings in an onboard non-volatile memory, substantially more than existing insulin pumps including the Paradigm® Revel™. Storing more events is very helpful to physicians treating diabetic patients. Additionally, the present invention has a larger display screen than most other existing insulin pumps at 900 sq. mm. One advantage of a larger screen is that patients who may have impaired vision can easily read the display information on the screen.

Therefore, the need exists for a low-cost drug delivery device having a cartridge system containing a plurality of reservoirs, capable of working in tandem with a delivery pump system, for the delivery of more than one drug.

SUMMARY OF THE INVENTION

The present invention overcomes the disadvantages of the prior art and fulfills the needs noted above by providing a drug delivery device having a delivery pump system, and a cartridge system.

More specifically, the present invention includes a drug delivery device having a delivery pump system, a cartridge system, a cannula and an insertion mechanism, and a plurality of conduits. The cartridge system of the drug delivery device snaps into the delivery pump system and is securely engaged to it.

The delivery pump system includes a plurality of electromagnetic coils that drive a plurality of magnets on the cartridge system that applies a force to a pump membrane of the cartridge system. The delivery pump system has a controller in communication with the electromagnetic coils to adjust the force applied by the electromagnetic coils, a power source, and a user interface configured to present information to a user. Additionally, the delivery pump system has a membrane switch that is communicatively linked to the controller. The membrane switch has a plurality of buttons, for example, "Up", "Down" and "Select/Enter" (shaped as a drip) buttons, for input of information. The delivery pump system further includes a touch screen, display and backlight assembly that is communicatively linked to the controller, the touch screen providing the user with an alternative and easy to use medium to input information to the drug delivery device.

The plurality of conduits each includes a proximal end, a distal end, and a lumen extending from its proximal end to its distal end. The proximal ends of the plurality of conduits are securely engaged to the distal ends of the cannula and the insertion mechanism, and the distal ends are securely engaged to the proximal ends of a fluid outlet component of inlet/outlet members of the cartridge system.

The present invention further includes a drug delivery device having an integrated glucose meter that enables the user to measure his or her blood glucose level by inserting a test strip into a strip connector housed on a circuit board of the delivery pump system. The user is then able to apply a blood sample to the test strip and read his or her blood glucose level directly from the user interface display. Additionally, the drug delivery device can interpret the blood glucose readings and either make a dosage recommendation to the patient user or administer a dose based on user configuration and settings.

The present invention further includes a cartridge system having a plurality of reservoirs each with volume, preferably, of 1.5 ml. Each of the plurality of reservoirs can be pre-filled with different medicaments. A pump membrane is placed between two gold-plated neodymium-iron-boron disk magnets that are each housed within a pump body insert. Each of the pump body inserts has a fluid receiving opening, a fluid discharge opening, a plurality of inlet channels, and a plurality of outlet channels. The pump body inserts are placed between two inlet/outlet members. Each of the inlet/outlet members has a fluid receiving opening, a fluid discharge opening, and a fluid outlet component. Additionally, each of the inlet/outlet members has a male part that securely engages to a female part of the reservoir forming an airtight seal. The reservoir, the fluid receiving opening of the inlet/outlet member and the pump body insert, the plurality of inlet channels, the plurality of outlet channels, and the fluid discharge opening of the pump body insert, the fluid discharge opening and the fluid outlet component of the inlet/outlet member are in fluid communication. The cartridge system further includes valve membranes that are placed between the fluid receiving openings of the pump body inserts and the inlet/outlet members, and between the fluid discharge openings of the pump body inserts and the inlet/outlet members.

The valve membranes of the cartridge system can be pre-stressed and formed, for example, of Silastic Q7-4840. The reservoirs can be formed, for example, of Silastic Q7-4840, or Medical Grade Polyisoprene. The pump body inserts and the inlet/outlet members can be formed, for example, of clear polypropylene homopolymer, or clear Medical Grade Acrylic such as OPTIX CP-927. The pump membrane can be formed, for example, of Silastic Q7-4840.

The present invention also includes a cartridge system having a plurality of orifices to fill or re-fill a plurality of medicaments in the reservoirs. The plurality of orifices can be located on the reservoirs, or on the inlet/outlet members, the plurality of orifices being in fluid communication with the reservoirs.

The present invention further includes a method of delivering medicament using a drug delivery device having a cartridge system. The method includes the steps of providing a drug delivery device having a delivery pump system and a cartridge system, loading a plurality of pre-filled reservoirs containing fluid medicament to the cartridge system, engaging securely the cartridge system and the delivery pump system, selecting various parameters on a user interface of the delivery pump system including selecting pre-determined values or specifying user-defined values for the parameters, and connecting an infusion set to the drug delivery device.

The method of delivering medicament using the drug delivery device includes the additional steps of placing an inset of the infusion set on a body part of a patient, attaching the infusion set to the patient's body, and switching on the drug delivery device.

The method of delivering medicament using the drug delivery device wherein the step of connecting an infusion set to the drug delivery device further includes the steps of connecting one end of a Y-catheter to an outlet component of an inlet/outlet member, and delivering fluid medicament at a given rate. The step of delivering fluid medicament at a given rate can further include delivering fluid medicament at a controlled and continuous rate for a pre-determined or user-defined period of time. Alternatively, the step of delivering fluid medicament at a given rate can further include delivering fluid medicament at a programmable rate that is regulated by the patient.

The present invention also includes a method of delivering medicament using the drug delivery device having the cartridge system. The method includes the steps of providing a drug delivery device having a delivery pump system and a cartridge system, loading a plurality of reservoirs to the cartridge system, using an instrument to inject a plurality of fluid medicaments into the plurality of reservoirs, engaging securely the cartridge system and the delivery pump system, selecting various parameters on a user interface of the delivery pump system including selecting pre-determined values or specifying user-defined values for the parameters, and connecting an infusion set to the drug delivery device. The step of connecting an infusion set to the drug delivery device further includes the steps of connecting one end of a Y-catheter to an outlet component of an inlet/outlet member, and delivering fluid medicament at a given rate. The step of delivering fluid medicament at a given rate can further include delivering fluid medicament at a controlled and continuous rate for a pre-determined or user-defined period of time. Alternatively, the step of delivering fluid medicament at a given rate can further include delivering fluid medicament at a programmable rate that is regulated by the patient.

Other features and advantages of the present invention will become apparent from the following description of the invention, which refers to the accompanying drawings.

DETAILED DESCRIPTION OF THE PREFERRED EMBODIMENTS

Figure 1A:
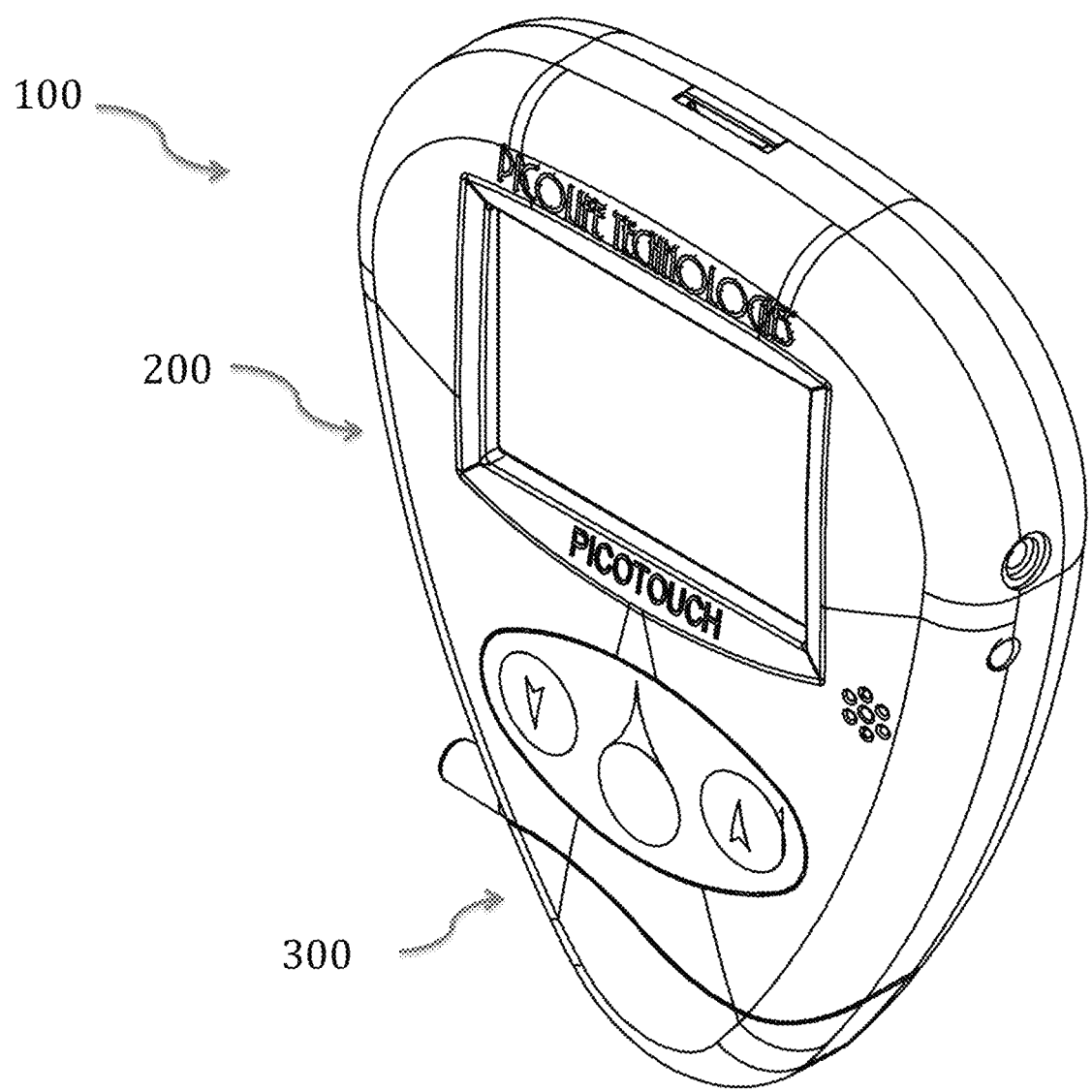
FIGS. 1A-1F illustrate a perspective view, front view, rear view, right side view, left side view, and bottom view, respectively, of a drug delivery device comprising a delivery pump system and a cartridge system in accordance with an embodiment of the present invention.
Figure 1B:
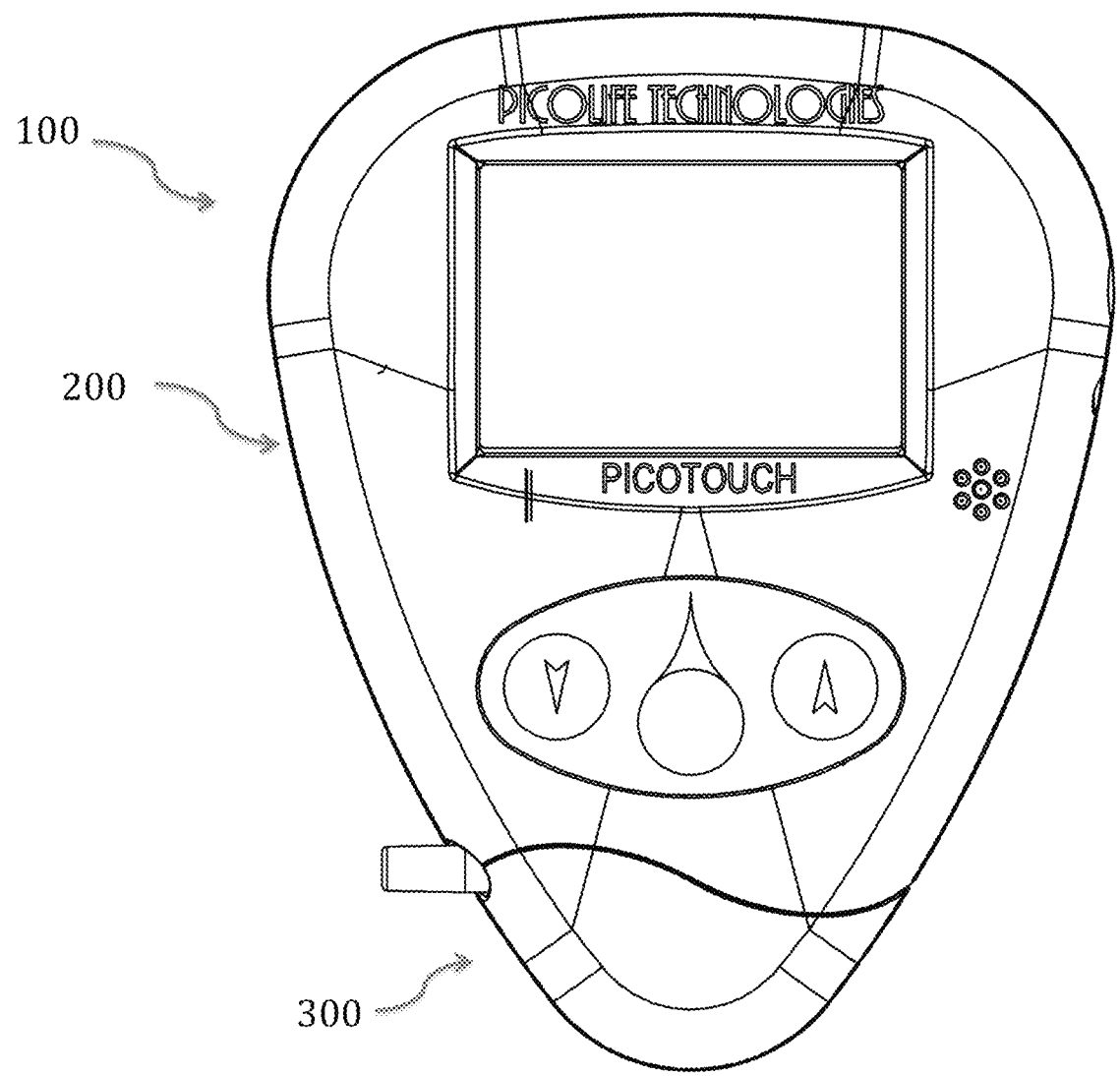
Figure 1C:
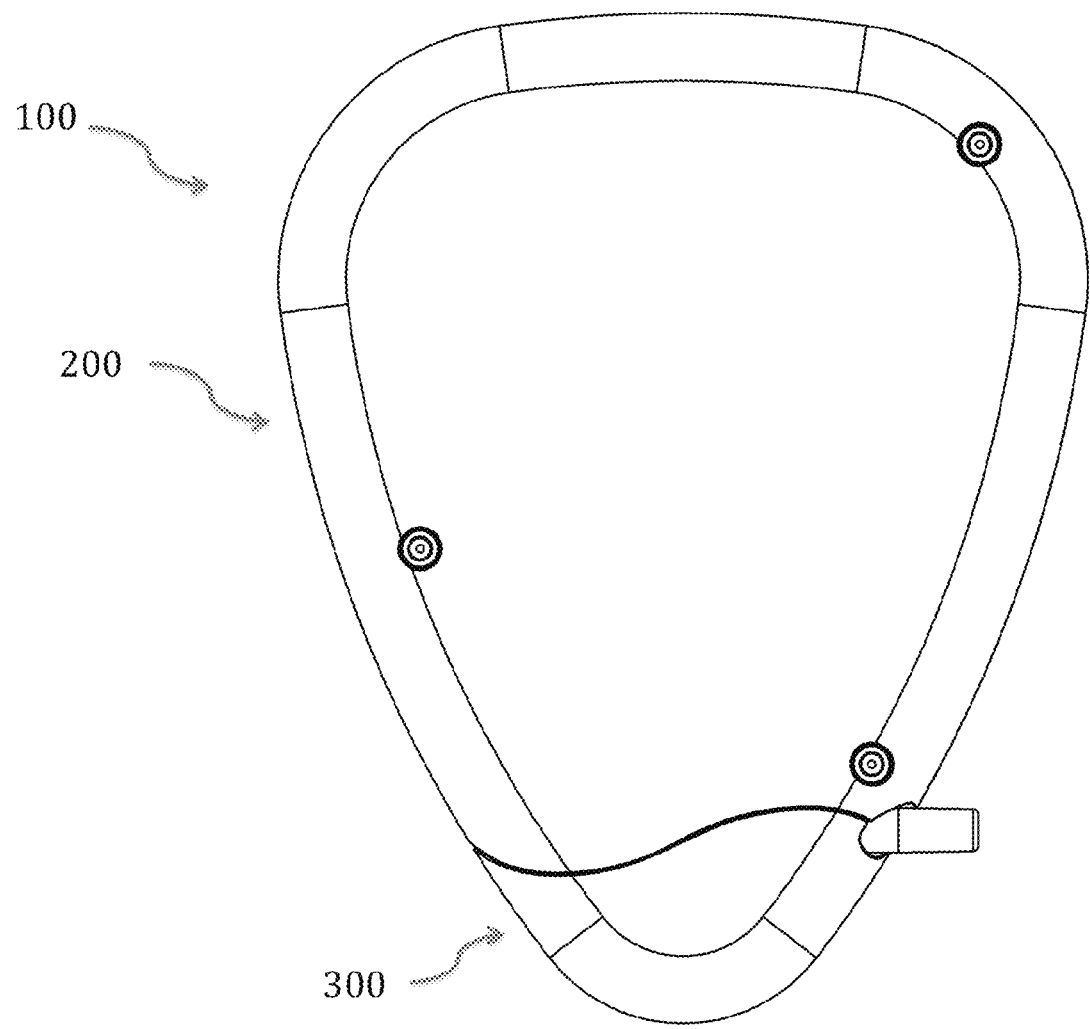
Figure 1D:
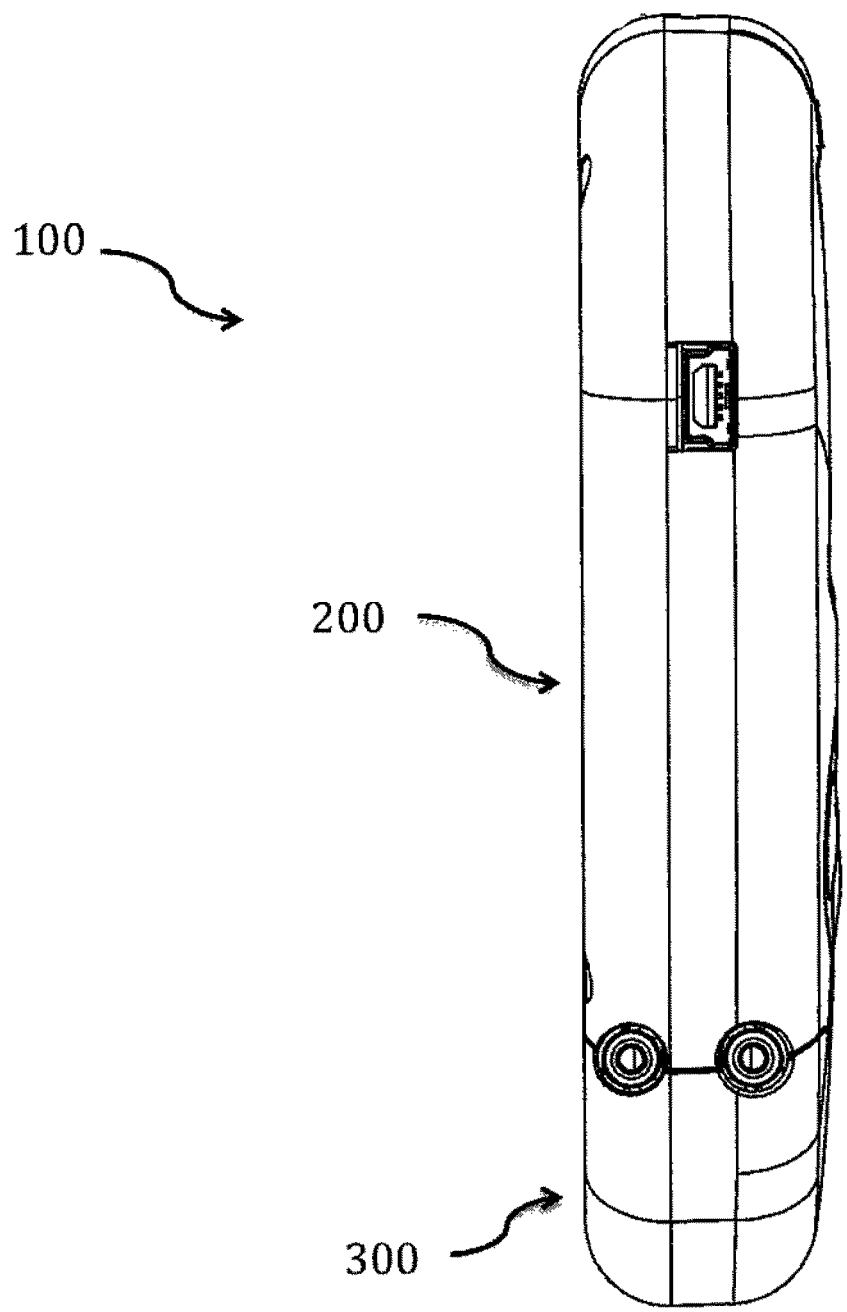
Figure 1E:
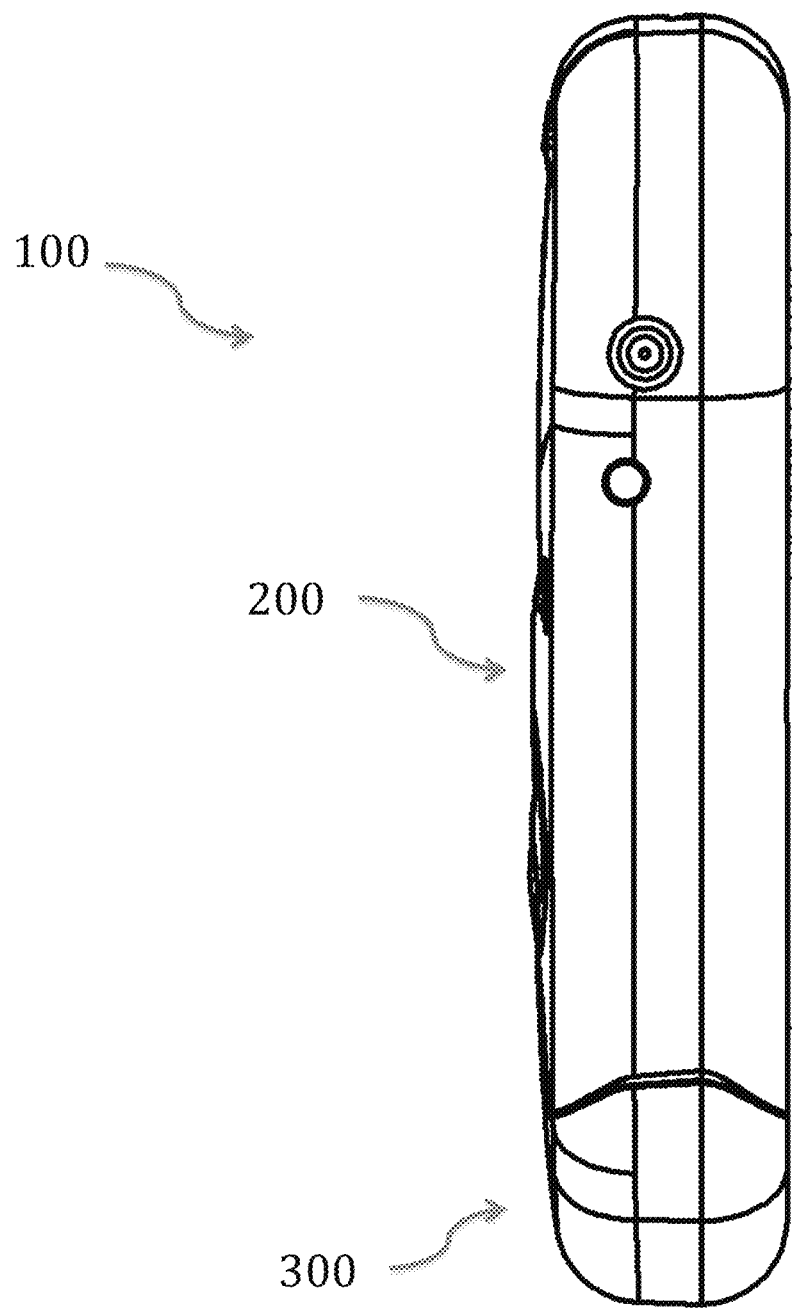
Figure 1F:
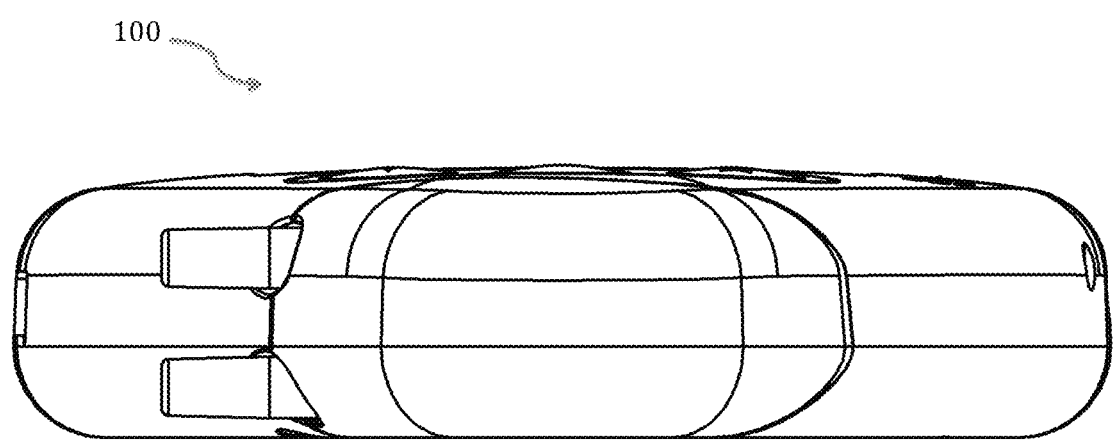

Disclosed embodiments relate to a drug delivery device for delivery of medicament, the device having a delivery pump system, and a cartridge system.

The term "fluid" is defined as a state of matter or substance (liquid or gas) whose particles can move about freely, and has no fixed shape or conform to the shape of their containers.

The term "channel" is defined as a passage for fluids to flow through.

The term "medicament" is defined as a substance used in therapy, a substance that treats, prevents or alleviates the symptoms of disease, a medicine in a specified formulation, or an agent that promotes recovery from injury or ailment.

The term "user" or "patient user" is defined as a person who uses or operates the drug delivery device.

Referring now to the drawings, where like elements are designated by like reference numerals, FIGS. 1A-1F illustrate a drug delivery device 100 in accordance with an embodiment of the invention. The drug delivery device 100 includes a delivery pump system 200 and a cartridge system 300. The overall dimensions of the drug delivery device 100 are preferably 3.75" (length)×3.0" (width)×0.74" (thickness). The drug delivery device 100 is preferably powered by a multi-cell set of rechargeable batteries, for example, Lithium-ion batteries, and the drug delivery device 100 has delivery flow rates in the range of 0 to 0.5 u in increments of tenths or hundredths of the value of the range.

Figure 2A:
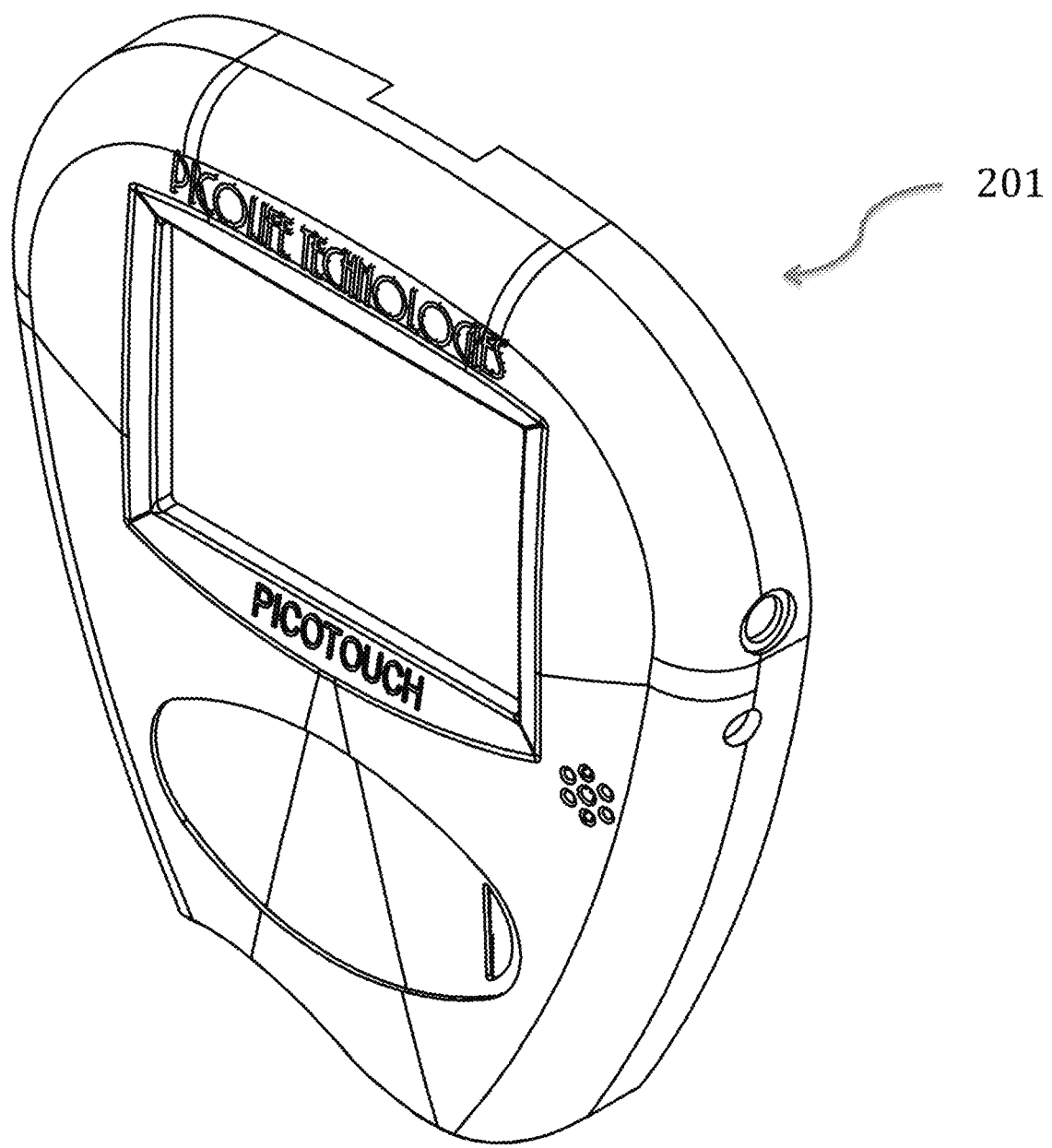
FIGS. 2A-2C illustrate a perspective view, front view and back view, respectively, of a front-top case of the delivery pump system in accordance with an embodiment of the present invention.
Figure 2B:
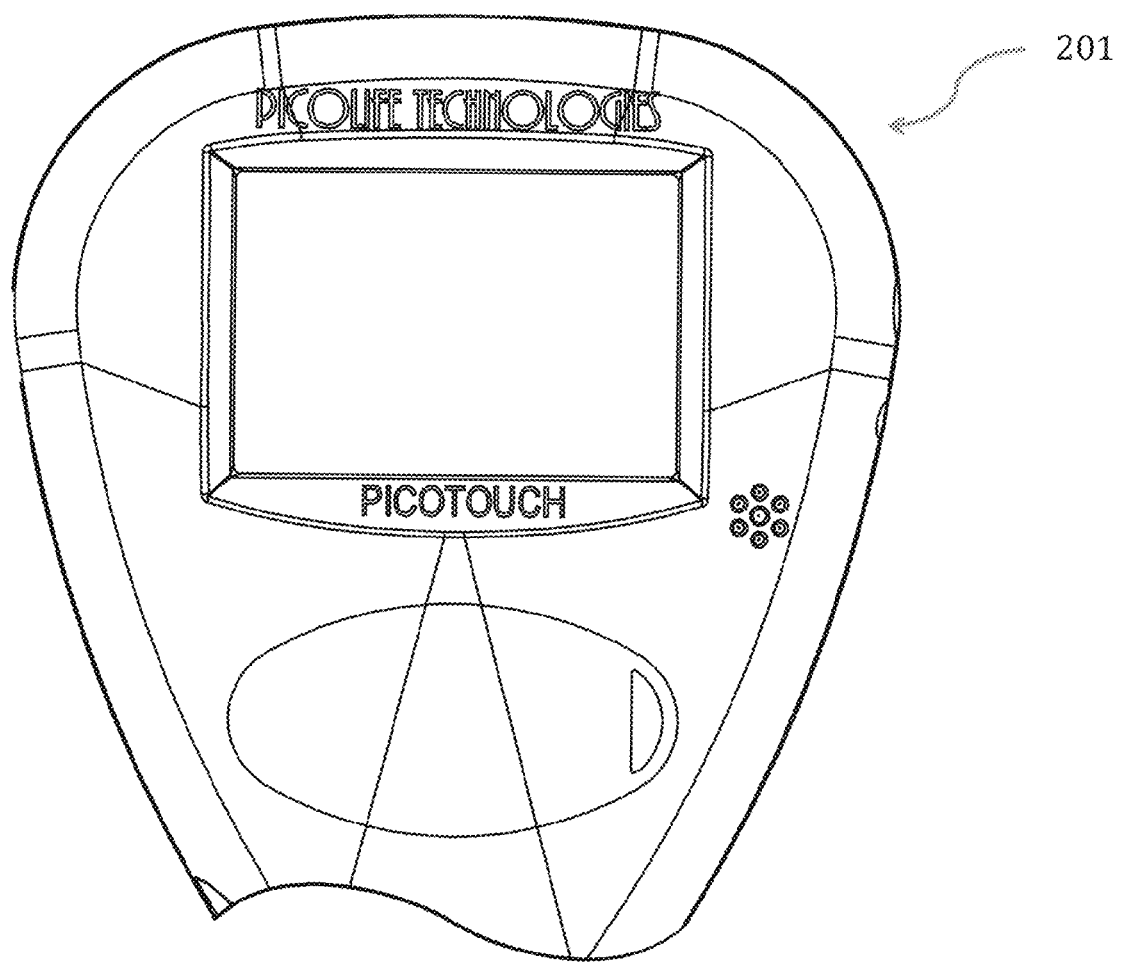
Figure 2C:
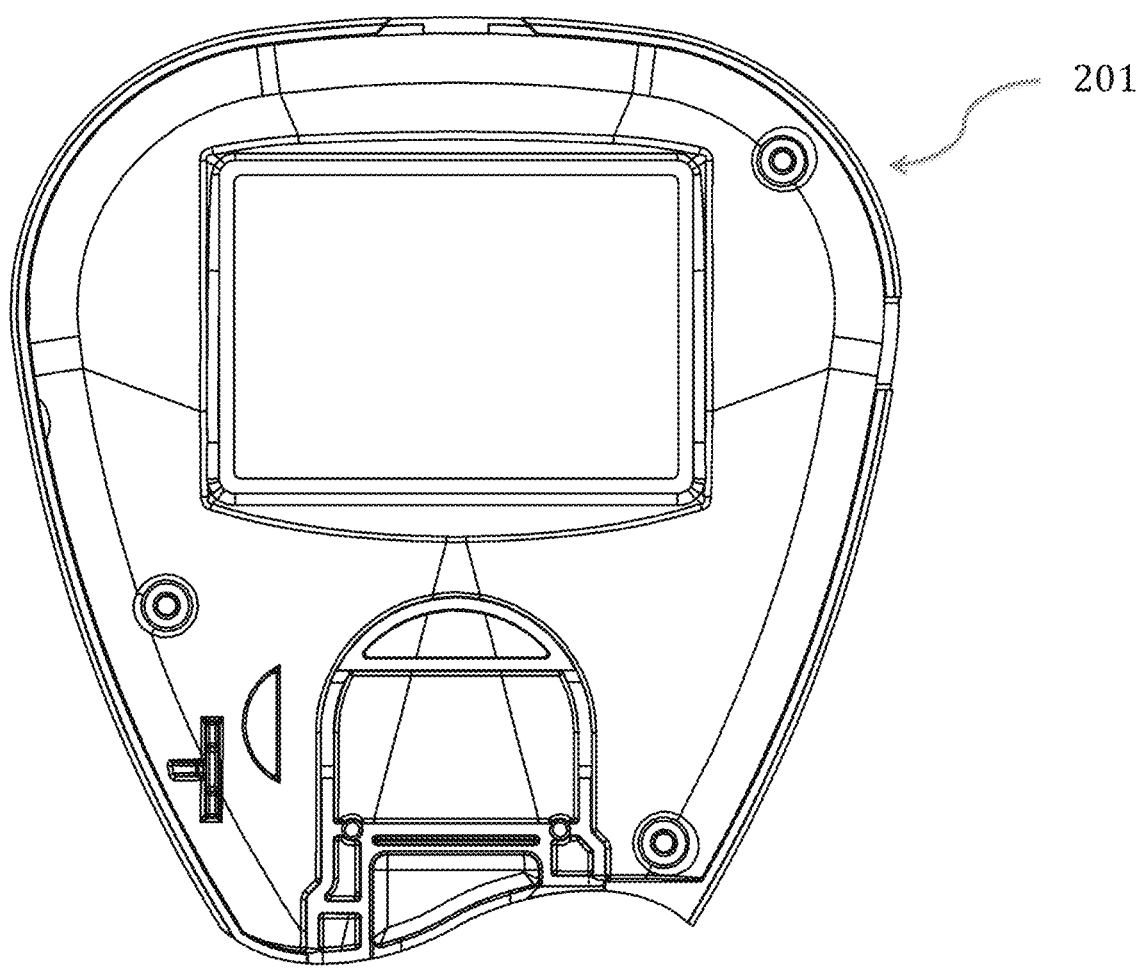
Figure 3A:
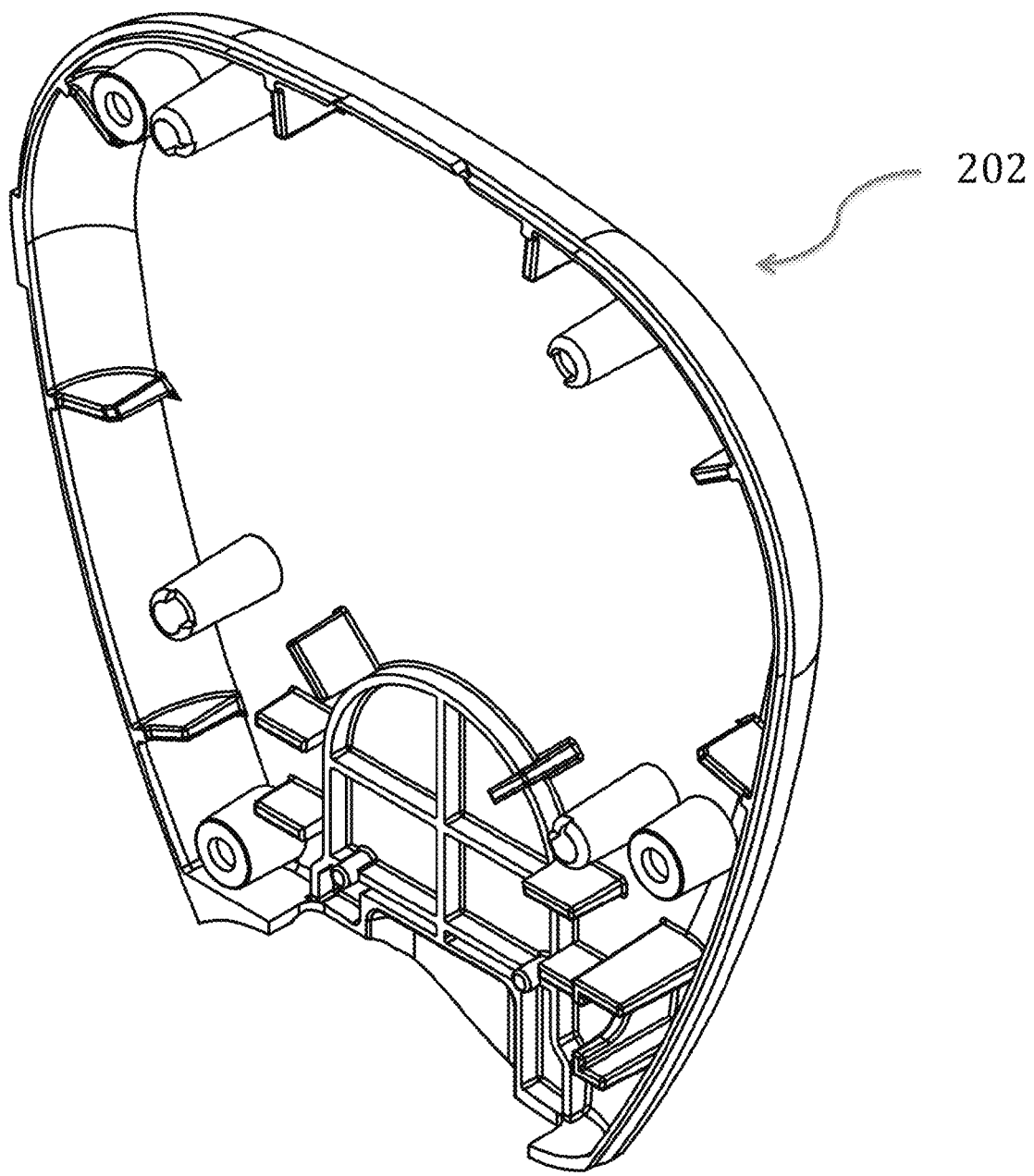
FIGS. 3A-3C illustrate a perspective view, back view and front view, respectively, of a rear-top case of the delivery pump system in accordance with an embodiment of the present invention.
Figure 3B:
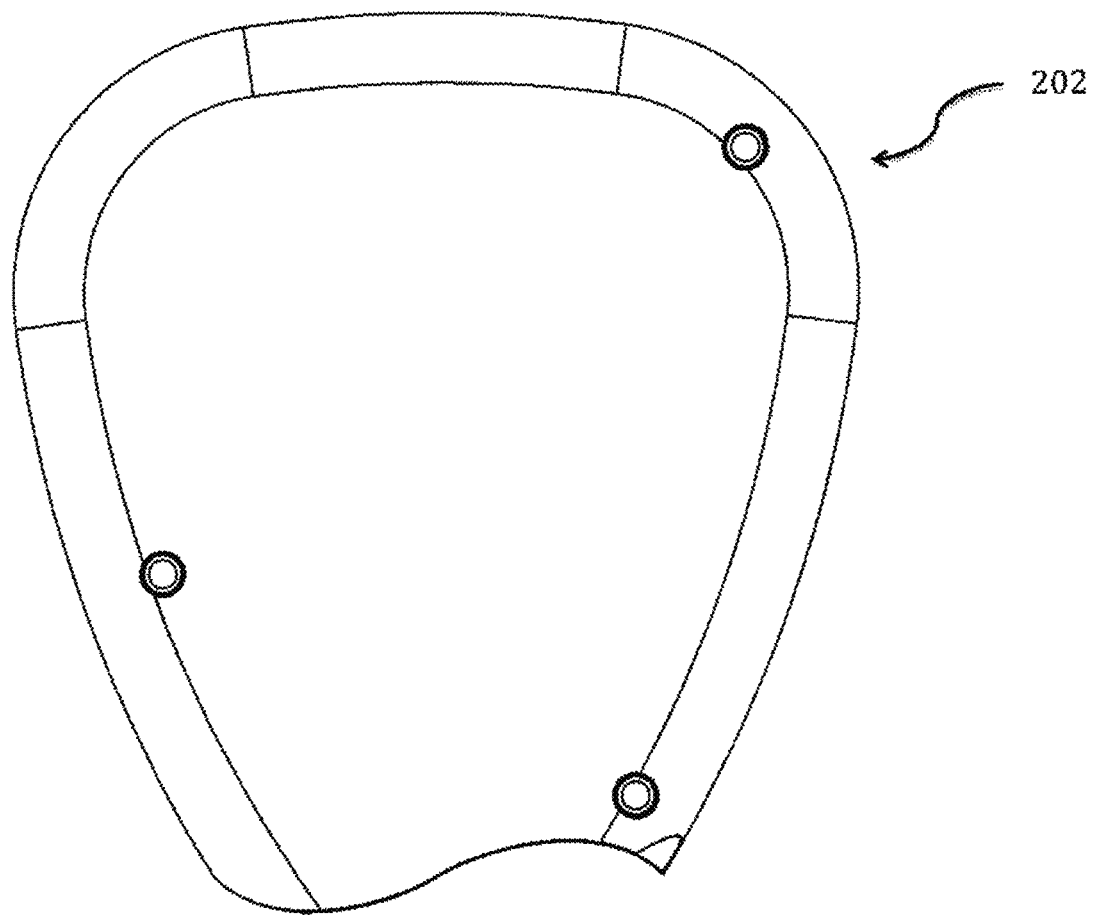
Figure 3C:
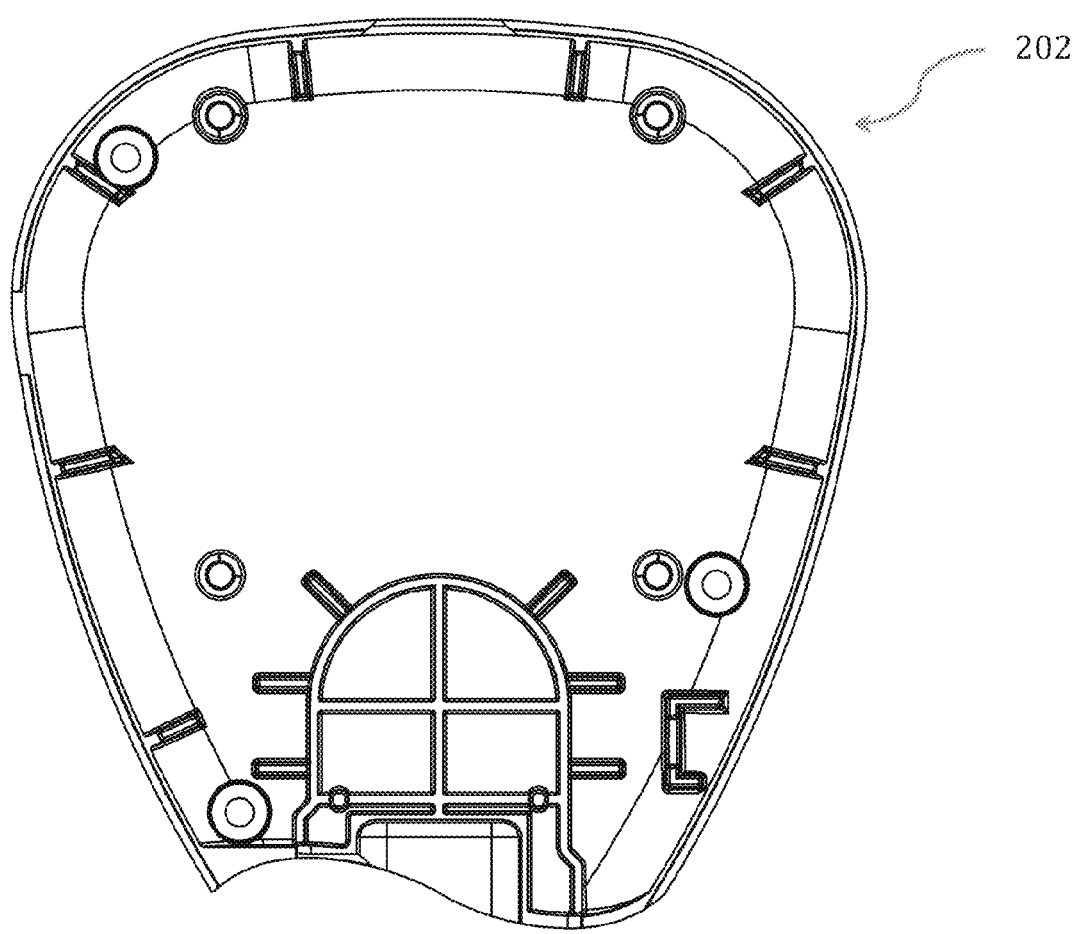

In a preferred embodiment of a delivery pump system 200 in accordance with the invention, as shown in FIGS. 2-9, the delivery pump system 200 has a front-top case 201, shown in FIGS. 2A-2C, and a rear-top case 202, shown in FIGS. 3A-3C. The front-top case 201 and the rear-top case 202 may preferably be designed to accommodate a horseshoe-shaped PCB board 208 (FIGS. 9A-9B), various parts of the delivery pump system 200 including a controller 208c (FIGS. 9A-9B) and a fully integrated glucose meter. The front-top case 201 and the rear-top case 202 are preferably made of ABS polymers and are securely engaged to each other using fasteners, for example, screws, or mated through thermoplastic welding, to form a delivery pump system housing.

The cartridge system 300 having reservoirs 302 (FIGS. 11A-11b), 302' (not shown) completes the shape of the drug delivery device 100 when inserted. The cartridge system 300 snaps into the delivery pump system housing forming a close fit and can be decoupled easily by the user from the delivery pump system housing

TABLE 1

Delivery Pump System of the Present Invention

Front-Top Case

| | |
|---|---|
| Overall dimensions: | 3.2" (length) × 3.0" (width) × 0.5" (thickness) |
| Basic shape: | Shape as shown in FIGS. 2A-2C |
| Material: | Medical Grade ABS polymer |
| Number: | Preferably, one |

Rear-Top Case

| | |
|---|---|
| Overall dimensions: | 3.2" (length) × 3.0" (width) × 0.28" (thickness) |
| Basic shape: | Shape as shown in FIGS. 3A-3C |
| Material: | Medical Grade ABS polymer |
| Number: | Preferably, one |

Membrane Switch

Figure 4:
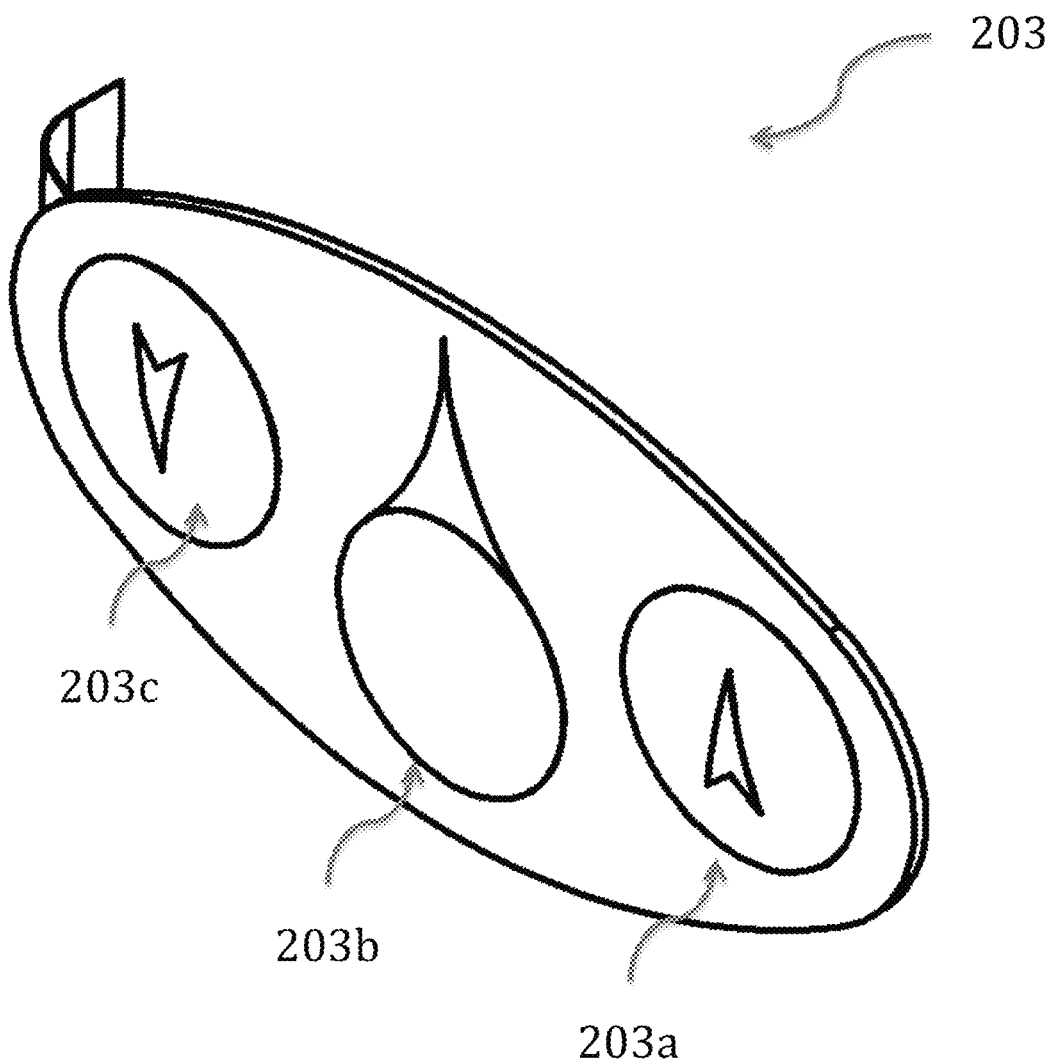
FIG. 4 illustrates a perspective view of a membrane switch of the delivery pump system in accordance with an embodiment of the present invention.

| | |
|---|---|
| Overall dimensions: | 0.77" (length) × 1.5" (width) × 0.020" (thickness) |
| Basic shape: | Shape as shown in FIG. 4 |
| Material: | Polyester |
| Number: | Preferably, one |

Touch Screen, Display and Back-Light

Figure 5:
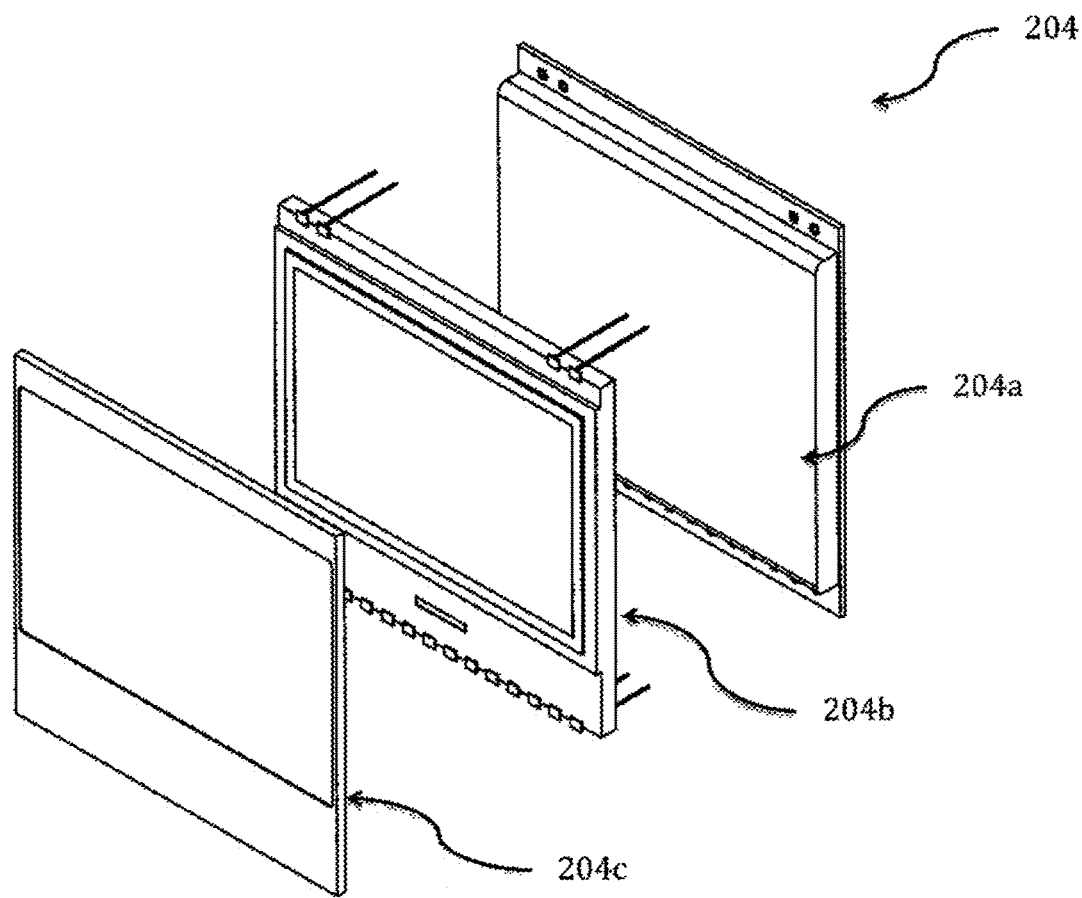
FIG. 5 illustrates a perspective view of a touch screen, display and back-light assembly of the delivery pump system in accordance with an embodiment of the present invention.

| | |
|---|---|
| Overall dimensions: | 1.6" (length) × 1.5" (width) × 0.26" (height) |
| Basic shape: | Shape as shown in FIG. 5 |
| Sub-Parts: | Touch screen, display, back-light |
| Material: | Glass, polymer, semiconductor, and metallic composite |
| Number: | Preferably, one |

Pump Housing

Figure 6A:
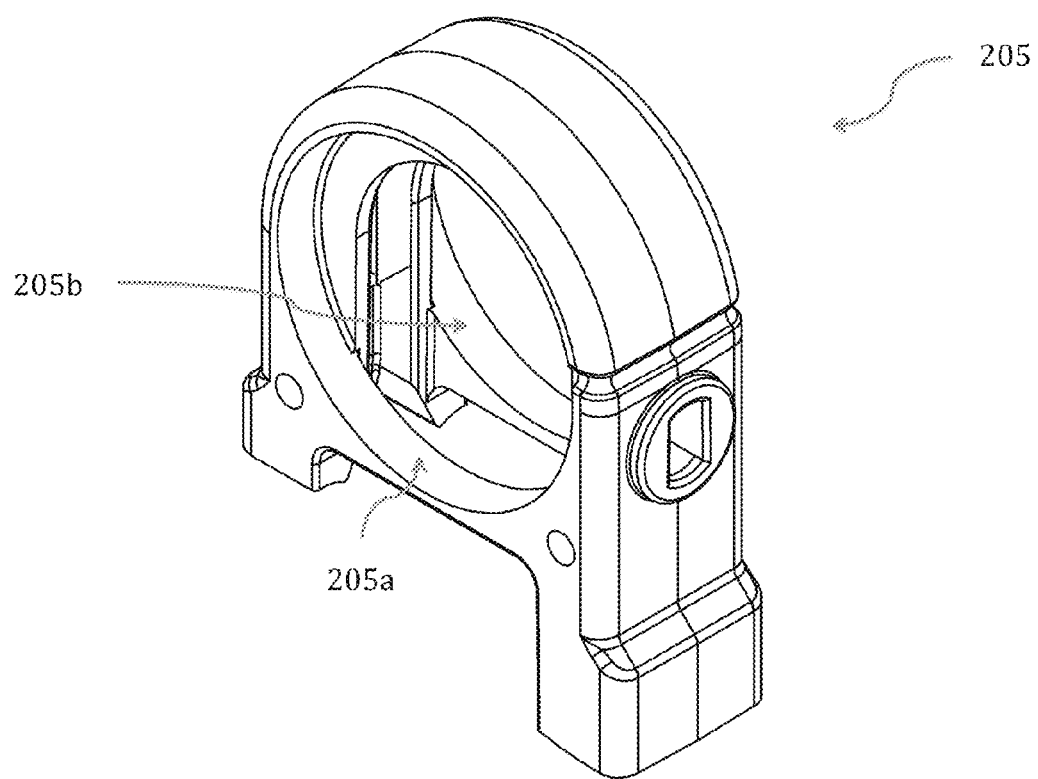
FIGS. 6A-6C illustrate a perspective view, back view and left view, respectively, of a pump housing of the delivery pump system in accordance with an embodiment of the present invention.
Figure 6B:
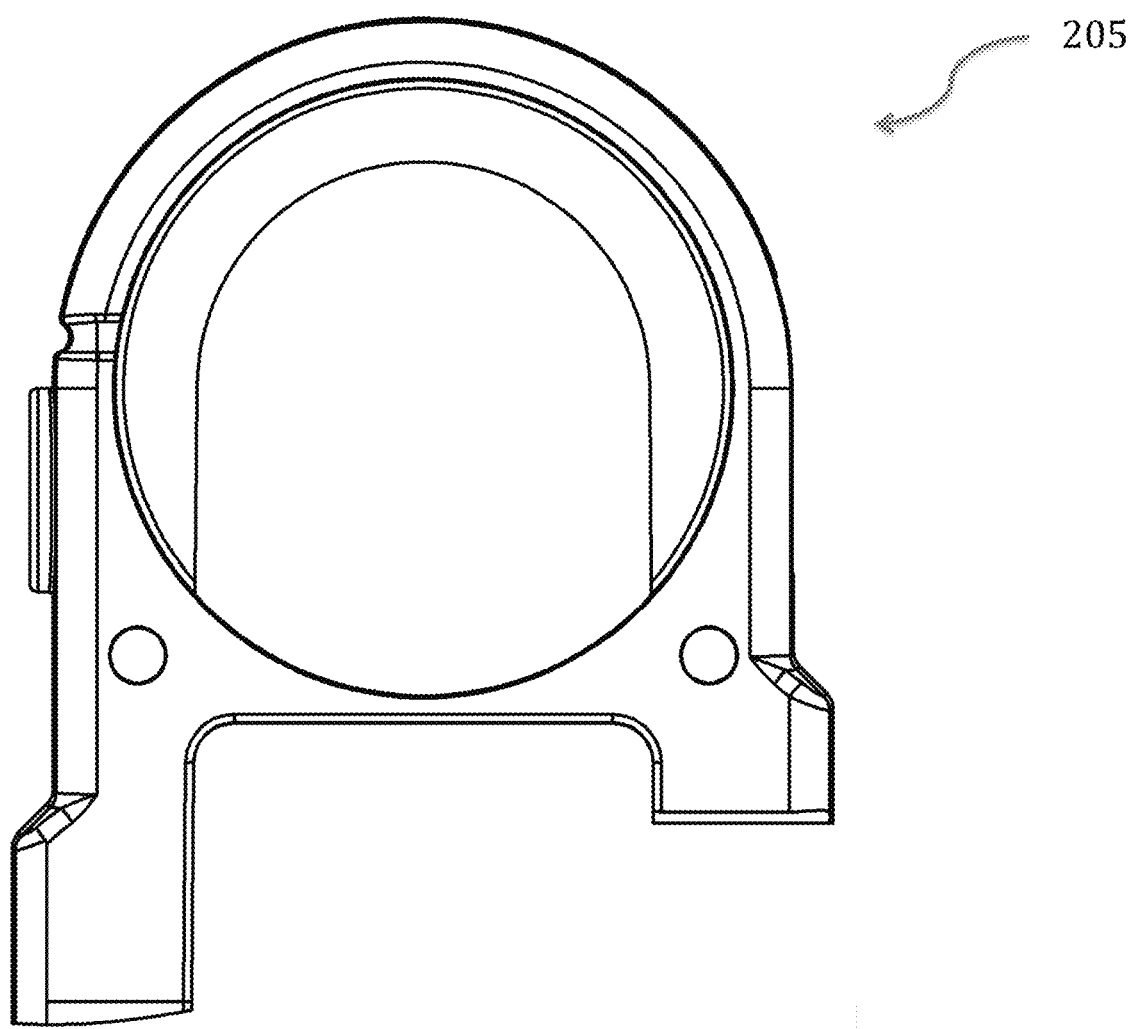
Figure 6C:
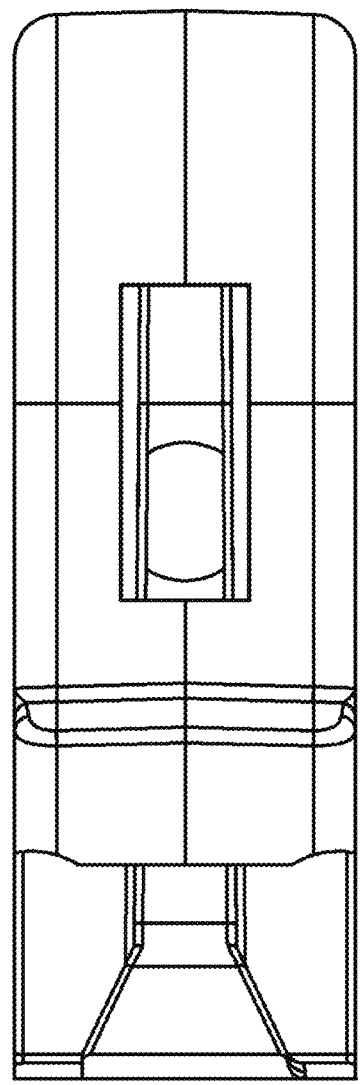

| | |
|---|---|
| Overall dimensions: | 1.2" (length) × 1.0" (width) × 0.39" (height) |
| Basic shape: | Shape as shown in FIGS. 6A-6C |
| Material: | Medical Grade ABS polymer |
| Number: | Preferably, one |

Electromagnetic Coil

Figure 7:
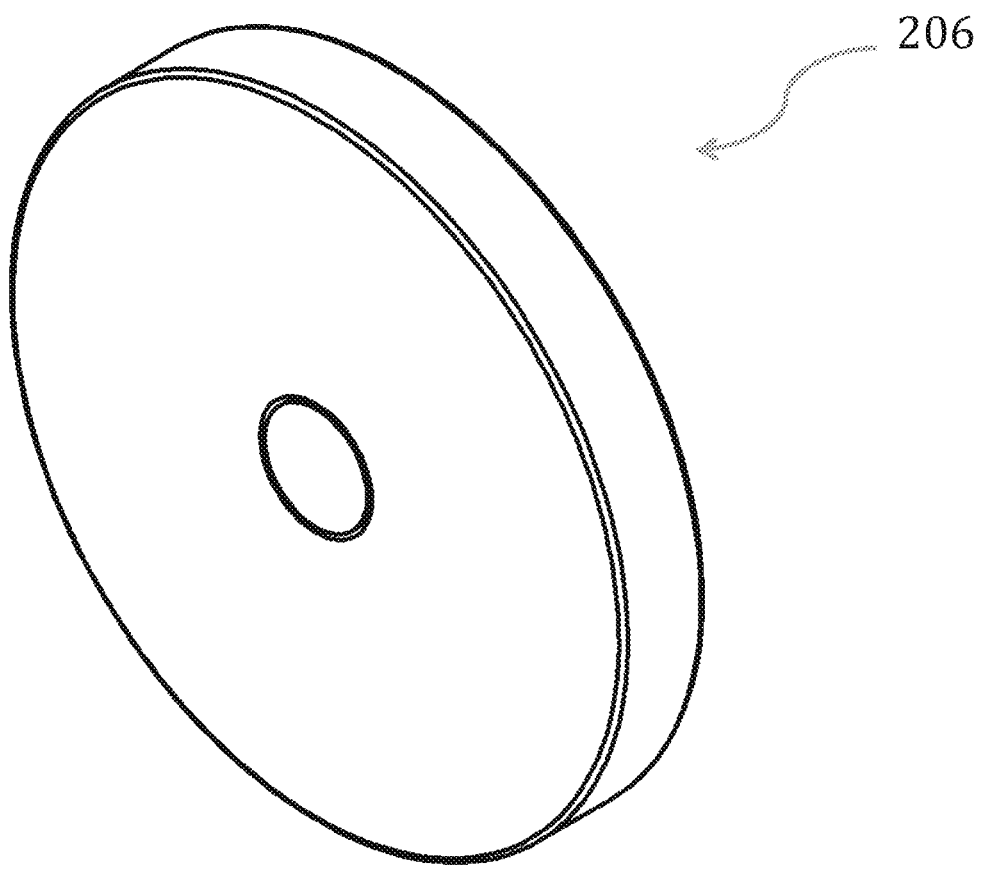
FIG. 7 illustrates a perspective view of an electromagnetic coil of the delivery pump system in accordance with an embodiment of the present invention.

| | |
|---|---|
| Overall dimensions: | 0.75" (diameter) × 0.10" (thickness) |
| Basic shape: | Shape as shown in FIG. 7 |
| Material: | Bond coated copper wire |
| Number: | Preferably, two |

Locking Plunger

Figure 8:
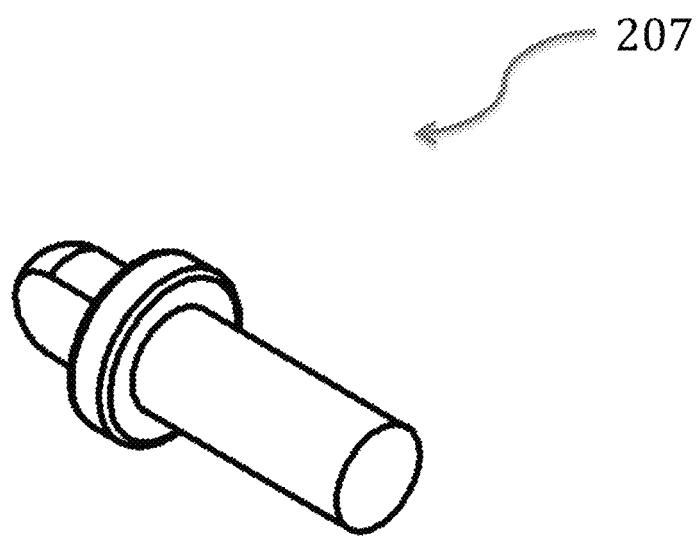
FIG. 8 illustrates a perspective view of a locking plunger of the delivery pump system in accordance with an embodiment of the present invention.

| | |
|---|---|
| Overall dimensions: | 0.63" (length) × 0.125" (radius) |
| Basic shape: | Shape as shown in FIG. 8 |
| Material: | Medical Grade ABS polymer |
| Number: | Preferably, one |

Circuit Board

TABLE 1-continued

Delivery Pump System of the Present Invention

Sub-Assembly

Figure 9A:
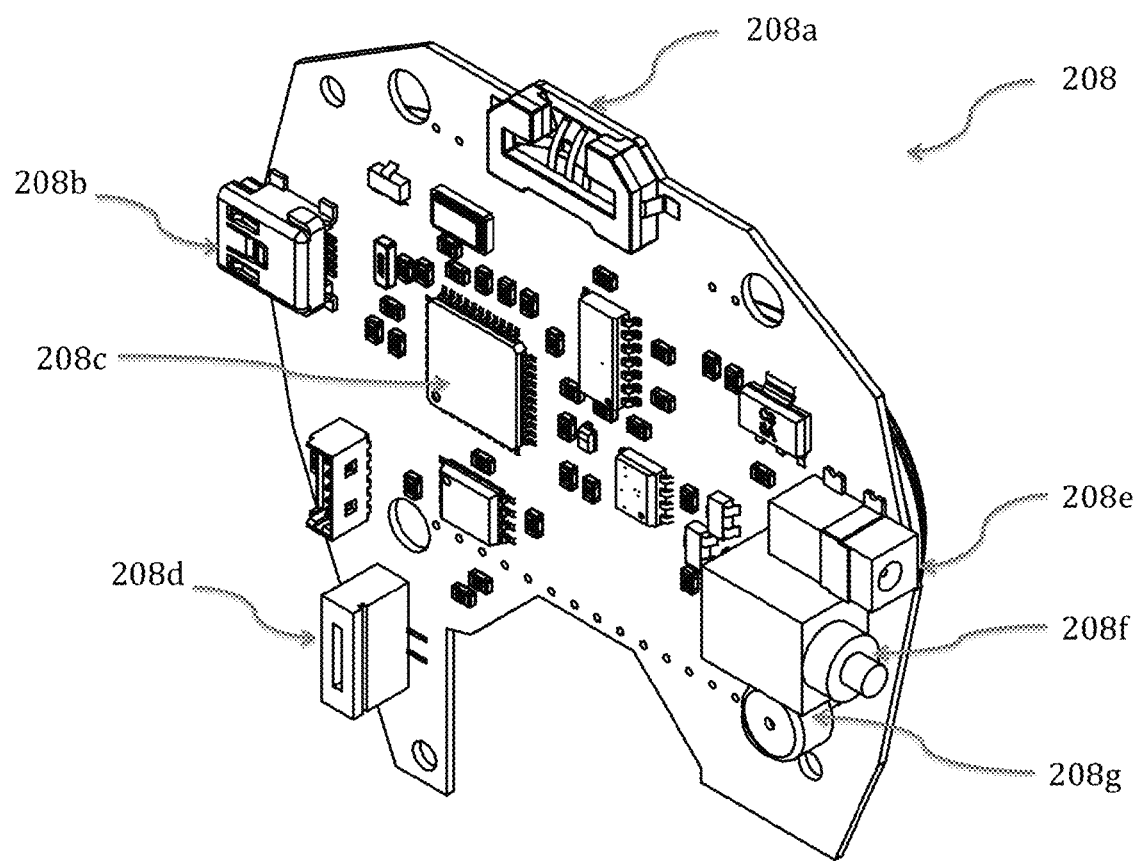
FIGS. 9A-9B illustrate a perspective view and back view, respectively, of a circuit board assembly of the delivery pump system in accordance with an embodiment of the present invention.
Figure 9B:
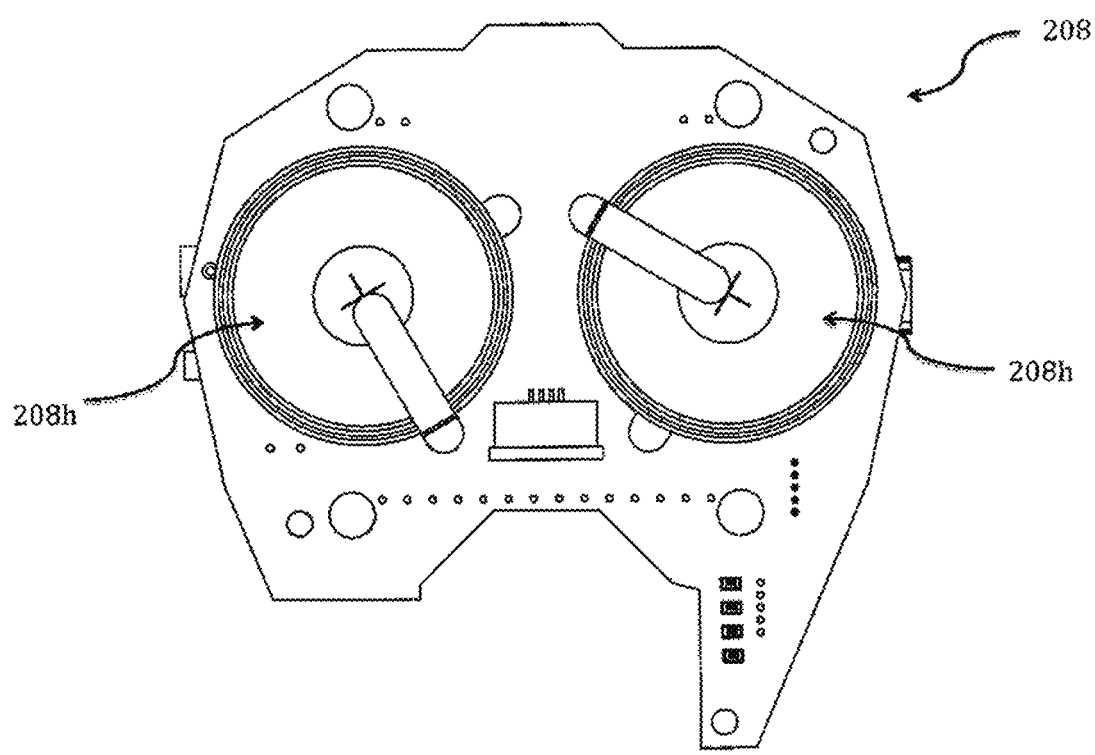

| | |
|---|---|
| Basic shape: | Shape as shown in FIGS. 9A-9B |
| Sub-parts: | Micro controller, strip connector, charging connector, USB port, ZIF connector, buzzer, power button |
| Number: | Preferably, one |

The clamshell housing is designed to accommodate two electromagnetic coils 206 (FIG. 7), 206' (not shown) on its juxtaposed surfaces. The diameter of the clamshell housing is determined by the size and design of the electromagnetic coils 206 (FIG. 7), 206' (not shown), which is directly related to the electromagnetic force required for fluid flow. For example, the diameter of the electromagnetic coils 206 (FIG. 7), 206' (not shown) for a drug delivery device 100 can be 0.75" diameter by 0.10" thick. When the cartridge system 300 is inserted into the clamshell housing, the electromagnetic coils 206 (FIG. 7), 206' (not shown) and magnets 305 (FIG. 14) are substantially axially aligned. Furthermore, the positioning of the electromagnetic coils 206 (FIG. 7), 206' (not shown) in the clamshell housing and the magnets 305 (FIG. 14) results in optimum actuation of a pump membrane 304 (FIG. 13), improving overall pump efficiency.

Referring to FIG. 4, the delivery pump system 200 has a membrane switch 203 for input of information into the drug delivery device 100. The membrane switch has three buttons—"Up" button 203a, "Select/Enter" button 203b, and "Down" button 203c. These buttons are used for the following: to navigate menus, administer medicament(s), review saved data, change or modify user settings, wakeup device from standby operation, and input general information to the drug delivery device 100. The membrane switch 203 is connected to a circuit board 208 (FIGS. 9A-9B), preferably, using flexible flat cables (FFC) that may be attached using Zero Insertion Force (ZIF) connectors soldered to the circuit board 208.

The delivery pump system 200 has a touch screen, display and backlight assembly 204, as shown in FIG. 5. The touch screen 204c is a panel overlay that allows a user to input information into the drug delivery device 100. The touch screen 204c mimics the functions of the three buttons of the membrane switch 203. The touch screen 204c has three active regions: (a) a lower portion that mimics the functions of the "Select/Enter" button 203b; (b) an upper left portion that mimics the functions of the "Down" button 203c; and (c) an upper right portion that mimics the functions of the "Up" button 203a. The touch screen 204c and the buttons 203a, 203b, 203c can be used interchangeably, although the touch screen 204c cannot be used to "wake up" the drug delivery device 100 from its sleep mode. The touch screen, display and backlight assembly 204 is connected to a circuit board 208 (FIGS. 9A-9B), preferably, using flexible flat cables (FFC) that may be attached using Zero Insertion Force (ZIF) connectors soldered to the circuit board 208.

Referring to FIGS. 6A-6C, the delivery pump system 200 has a pump clamshell housing 205 to house electromagnetic coils 206 (FIG. 7), 206' (not shown). The pump clamshell housing 205 has cylindrical bores 205a, 205b on opposite ends designed to house the electromagnetic coils 206 (FIG. 7), 206' (not shown) both in thickness and diameter. The two electromagnetic coils 206 (FIG. 7), 206' (not shown) are connected to the circuit board 208 (FIGS. 9A-9B). A locking plunger 207, shown in FIG. 8, is used to securely lock the cartridge system 300 to the delivery pump system 200.

Referring to FIGS. 9A-9B, the circuit board 208 of the delivery pump system 200 includes a controller 208c, a strip connector 208a, a charging connector 208e, a power button 208f, a buzzer 208g, a ZIF connector 208d, a USB port 208b, which are electrically connected. The controller 208c may preferably be a single integrated circuit containing a processor core, memory and programmable input/output peripherals, for example, a PIC18F47J53. The controller 208c stores the software application program that controls the functioning of the drug delivery device 100. The strip connector 208a can preferably use a prepackaged glucose oxidase based electrochemical diagnostic strip. The USB port 208b can be used for communication with a computer and for downloading programs and software updates from a proprietary website. The drug delivery device 100 can be switched on or off using the power button 208f on the circuit board 208 and the drug delivery device 100 can be connected to a power source using the charge connector 208e via an AC/DC adaptor.

There are battery compartments 208h on the back of the controller 208c to house batteries, for example, two rechargeable Lithium-ion 3.6V batteries that may last an average of two years with repeated and regular charging. The port 208e for charging the batteries is housed conveniently along the side of the controller 208c directly above the start/reset button 208f. The start/reset button 208f can be activated with the use of an item with a small and rigid tip.

The drug delivery device 100 has a fully integrated glucose meter (embedded within the circuitry 208 and working collectively with the controller 208c) that enables the user to measure his or her blood glucose level by inserting a test strip into the strip connector 208a housed on the circuit board 208 of the delivery pump system 200. The user is then able to apply a blood sample to the test strip whereby the integrated glucose meter will automatically sense the application of blood and subsequently obtain a reading.

Figure 10A:
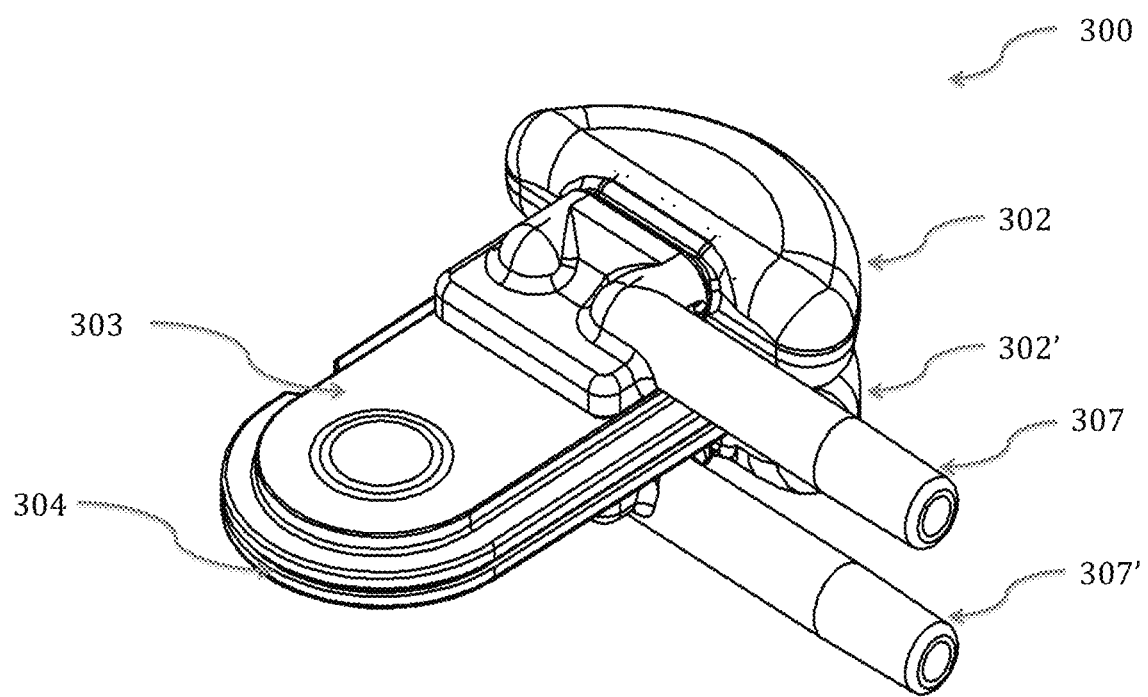
FIGS. 10A-10C illustrate a perspective view, rear elevation and top view, respectively, of a cartridge system in accordance with an embodiment of the present invention.
Figure 10B:
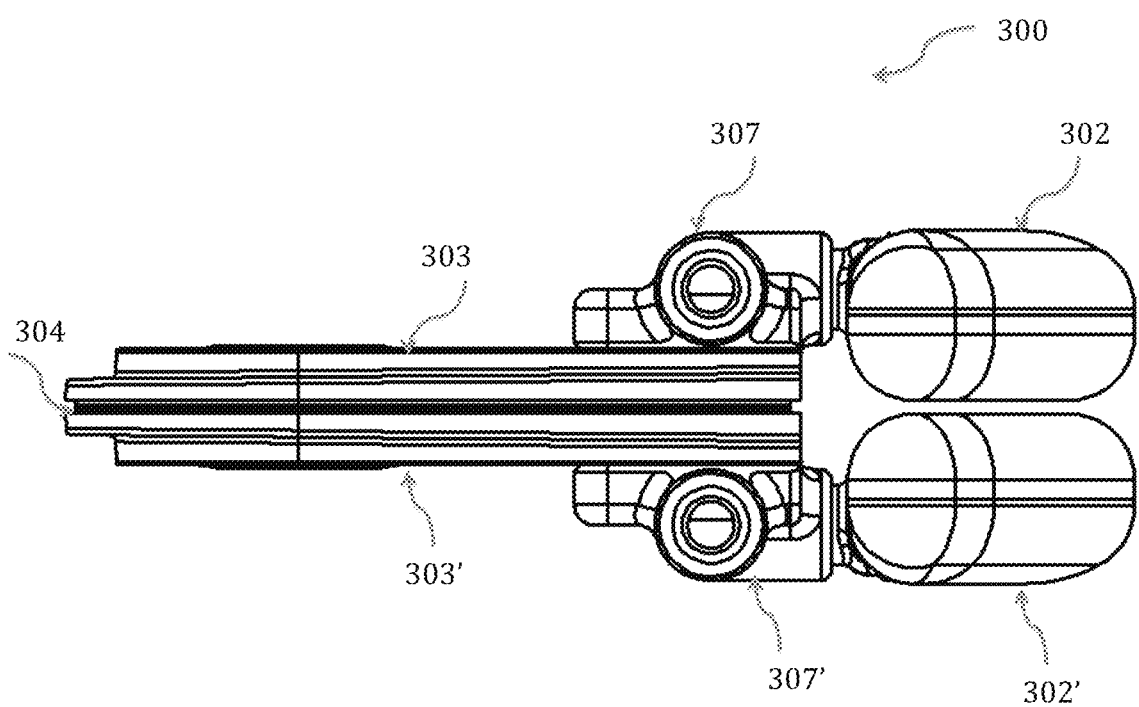
Figure 10C:
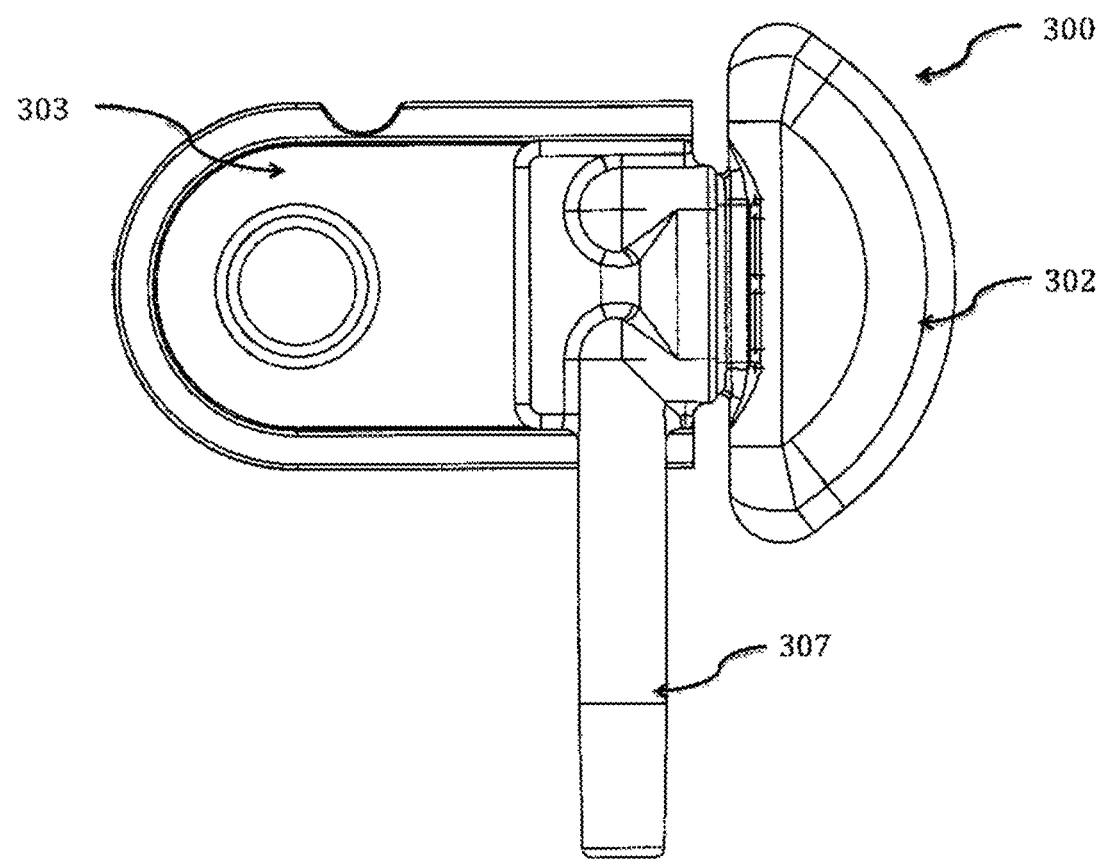

FIGS. 10A-10C illustrate the internals of a cartridge assembly 300 in accordance with an embodiment of the invention. The cartridge assembly 300 includes a plurality of reservoirs 302, 302', a plurality of pump body inserts 303, 303', a pump membrane 304, and a plurality of inlet/outlet members 307, 307'.

TABLE 2

Cartridge System of the Present Invention

Reservoir Shell

| | |
|---|---|
| Overall dimensions: | 1.56" (length) × 0.80" (width) × 0.71" (height) |
| Basic shape: | Shape as shown in FIGS. 19A-19C, 20A-20C |
| Material: | RTP 699 × 122676 NS—Acrylonitrile Butadiene Styrene (ABS) Medical Grade |
| Number: | Preferably, two |

Reservoir

Figure 11A:
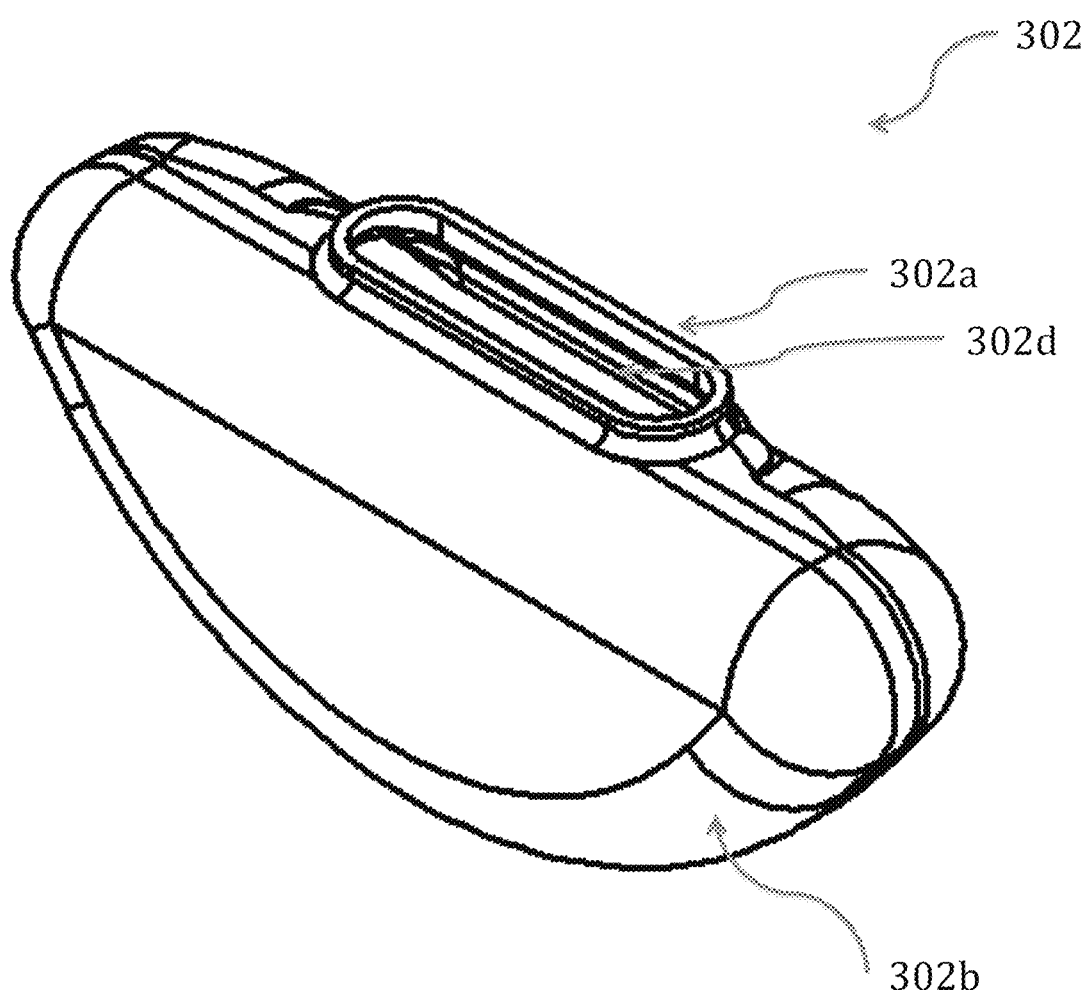
FIGS. 11A-11B illustrate a perspective view and top view, respectively, of a reservoir of the cartridge system in accordance with an embodiment of the present invention.
Figure 11B:
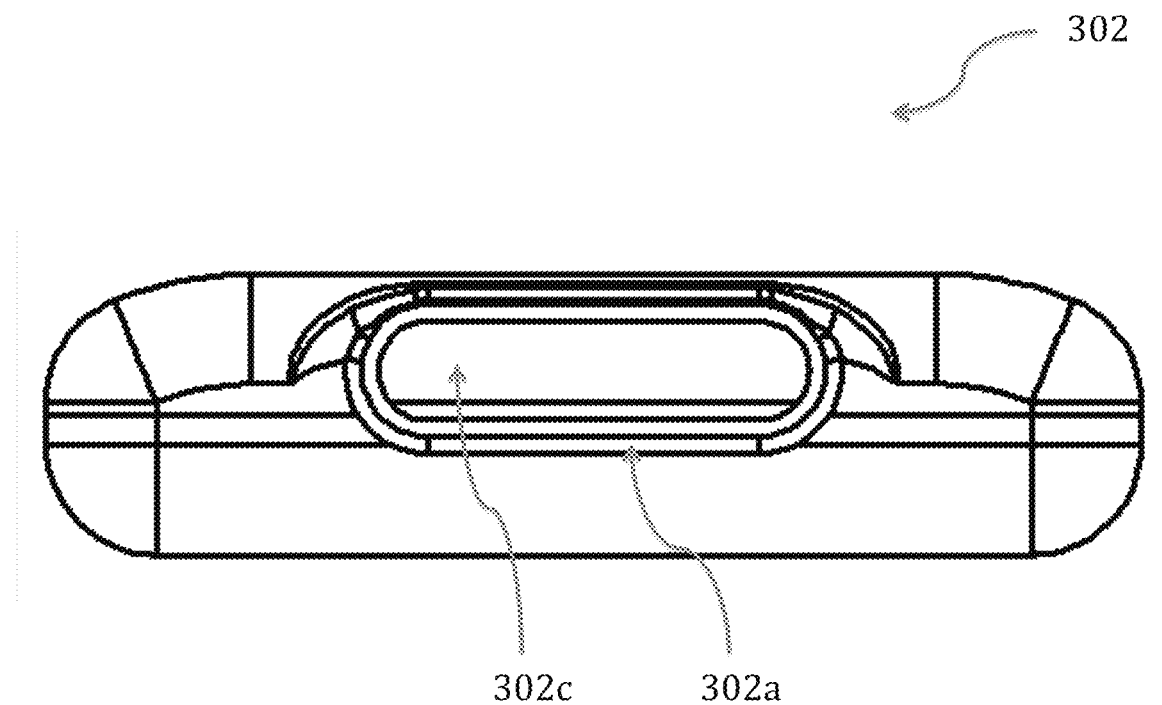

| | |
|---|---|
| Overall dimensions: | 0.99" (length) × 0.46" (width) × 0.26" (height) |
| Basic shape: | Shape as shown in FIGS. 11A-11B, and made of a material from a group consisting of elastomers, and the material having property such that the geometry is deformable |
| Material: | Silastic Q7-4840 or Medical Grade Polyisoprene |
| Number: | Preferably, two |

Pump Body Insert

| | |
|---|---|
| Overall dimensions: | 1.1" (length) × 0.7" (width) × 0.09" (height) |
| Basic shape: | Shape as shown in FIGS. 12A-12D, and having a plurality of flow channels, a fluid receiving opening, and a fluid discharge opening |

TABLE 2-continued

Cartridge System of the Present Invention

| | |
|---|---|
| Material: | Clear polypropylene homopolymer or medical grade acrylic |
| Number: | Preferably, two |

Inlet/Outlet Member

| | |
|---|---|
| Overall dimensions: | 1.37" (length) × 0.49" (width) × 0.2" (height) |
| Basic shape: | Shape as shown in FIGS. 16A-16D, and having a fluid receiving opening, a fluid discharge opening, and a fluid outlet component |
| Material: | Clear polypropylene homopolymer or medical grade acrylic |
| Number: | Preferably, two |

Magnets

| | |
|---|---|
| Overall dimensions: | 0.13" (diameter) × 0.06" (height) |
| Basic shape: | Cylindrical |
| Material: | Neodymium-iron-boron grade N42 magnets, gold plated (NdFeB) |
| Number: | Two |

Pump Membrane

Figure 13:
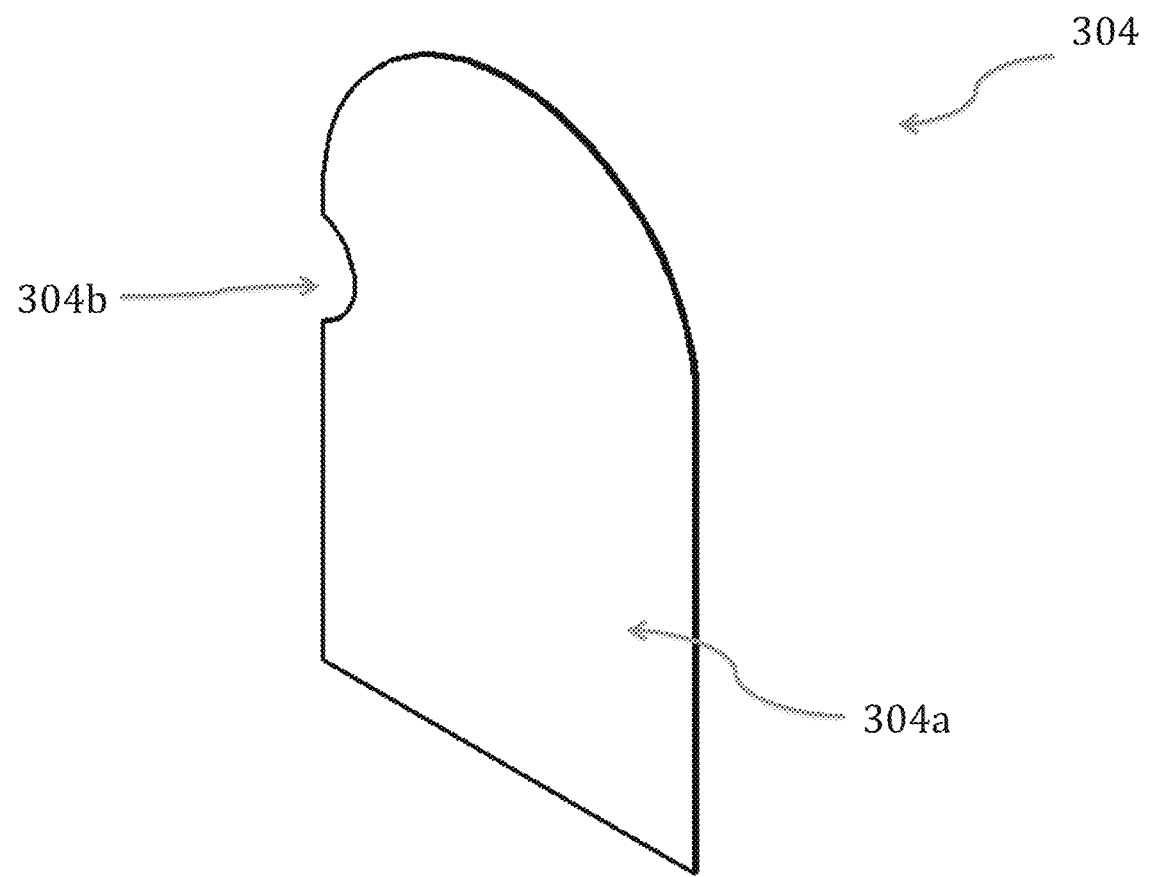
FIG. 13 illustrates a perspective view of a pump membrane of the cartridge system in accordance with an embodiment of the present invention.

| | |
|---|---|
| Overall dimensions: | 1.07" (length) × 0.67" (width) × 0.01" (thickness) |
| Basic shape: | Shape as shown in FIG. 13 |
| Material: | Silastic Q7-4840 |
| Number: | One |

Valve Membrane

| | |
|---|---|
| Overall dimensions: | 0.19" (diameter) × 0.04" (height) |
| Basic shape: | Cylindrical and domed |
| Material: | Silastic Q7-4840 |
| Number: | Four |

Referring to FIGS. 11A-11B, a reservoir 302 having an opening 302c is shown. The reservoir 302 is preferably made of elastomers and preferably made by liquid injection molding of Silastic Q7-4840 or transfer molding of Medical Grade Polyisoprene.

The advantages of using polymer materials to make the reservoirs 302, 302', pump body inserts 303, 303', inlet/outlet members 307, 307', and any housing portion is that they can be made in any size, designed in any way and manufactured with biocompatible materials. The polymer reservoirs allow better use of the interior volume available within the pump body, and the collapsible nature of the material allows for more innovative methods for withdrawing the liquid contents. The methods used in the manufacture of the polymer components as well as the arrangement and design of the cartridge system lends itself to being readily adaptable to commonly used sterilization techniques such as gamma irradiation, steam sterilization, or fluidic chemical sterilization.

Figure 16A:
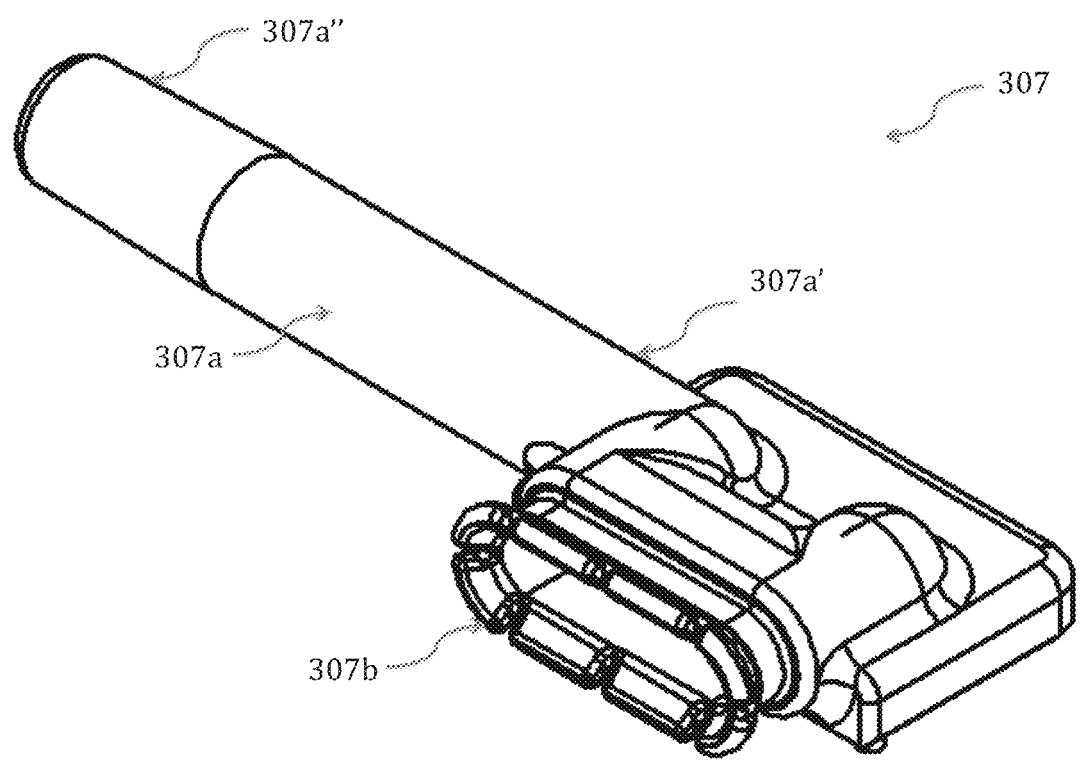
FIGS. 16A-16B illustrate a perspective view and bottom view, respectively, of a first inlet/outlet member of the cartridge system in accordance with an embodiment of the present invention.

The reservoir 302 has a substantially symmetrical body having a top end (not shown), a bottom end (not shown), an inner wall 302d, and an outer wall 302b. The top end of the reservoir 302 has an opening 302c that is encircled by the inner wall 302d and the outer wall 302b. At the top end, the inner wall 302d and the outer wall 302b project in an upward direction to form a female part 302a. The female part 302a is preferably of length about 0.42 inches. The female part 302a is securely engaged to a male part 307b (FIG. 16A) of an inlet/outlet member 307 (FIG. 16A).

The thickness of the reservoir 302 is preferably between 50μ and 200μ. The top end, the bottom end, the inner wall 302d and the outer wall 302b enclose a reservoir space for storage of fluid medicament. The reservoirs 302, 302' of the cartridge system 300 are preferably dual reservoir, pre-filled with fluid medicaments, each of the reservoirs 302, 302' capable of holding 1.5 ml of fluid medicament. Although FIGS. 11A-11B illustrate reservoir 302, it must be understood that reservoir 302' is substantially the same.

In another preferred embodiment of the invention, the reservoirs 302, 302' can be any free-form shaped body. The reservoirs 302, 302' can be mounted within a reservoir shell (not shown), the inside of the reservoir shell (not shown) having an insulation and sealed layer (not shown).

Figure 16B:
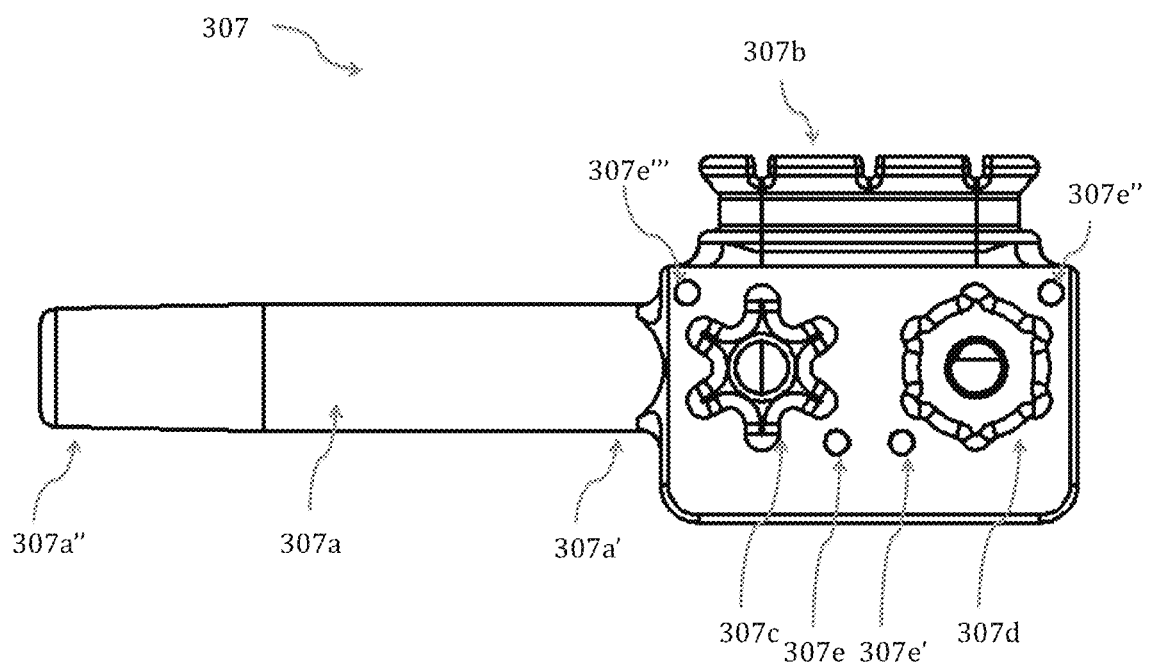
Figure 16C:
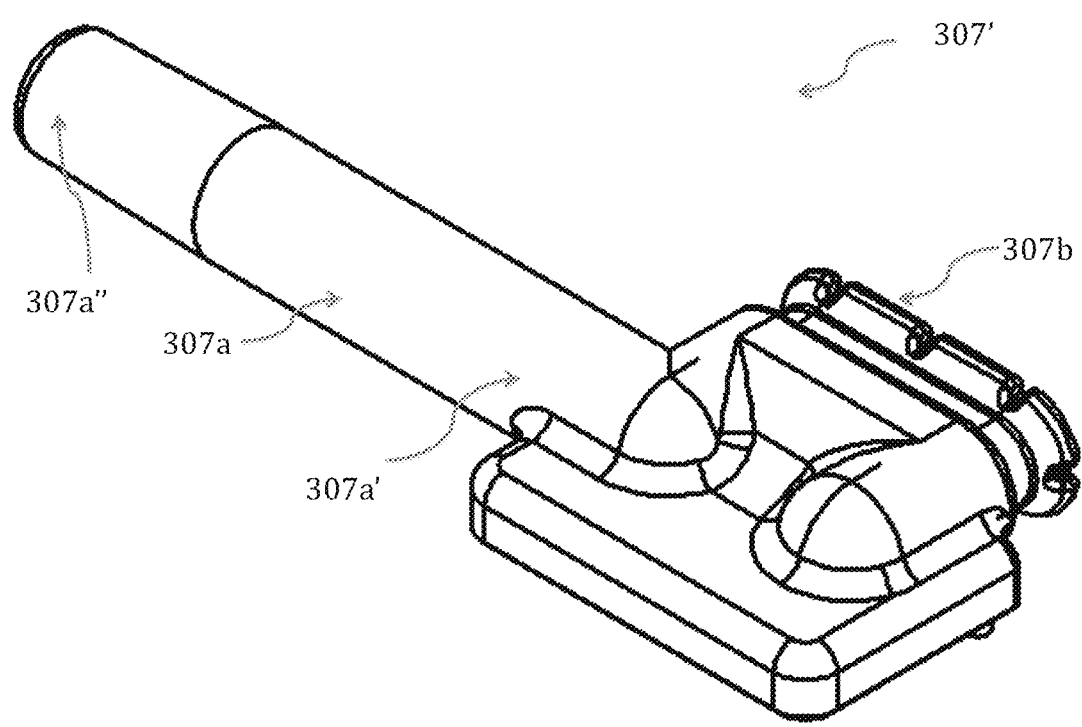
FIGS. 16C-16D illustrate a perspective view and bottom view, respectively, of a second inlet/outlet member of the cartridge system in accordance with an embodiment of the present invention.
Figure 16D:
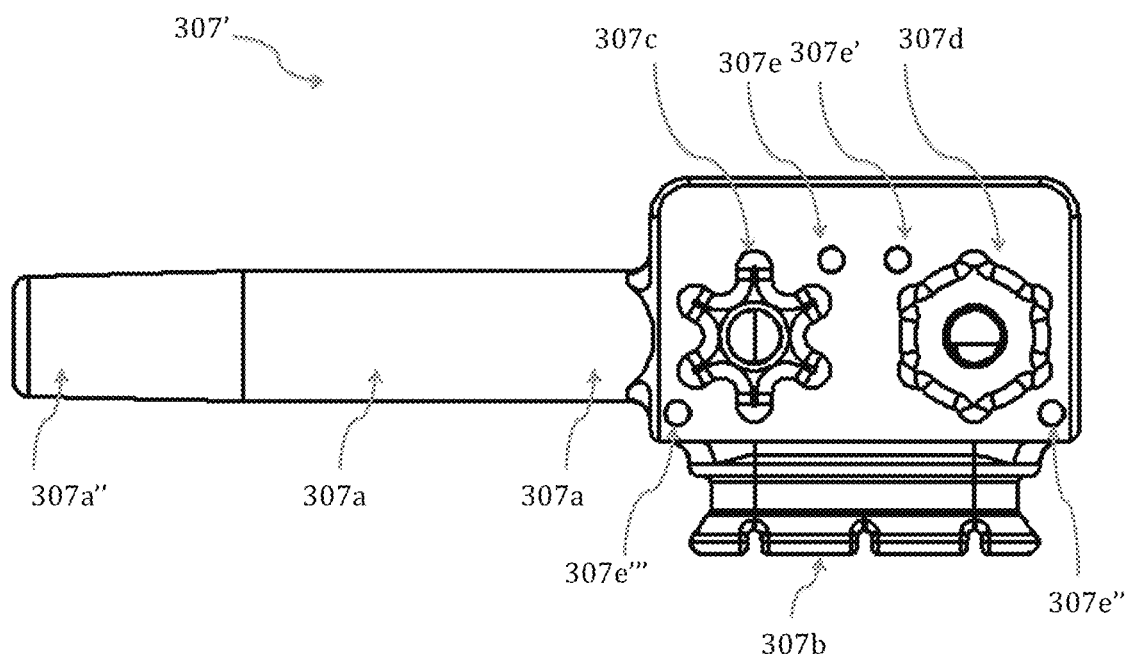
Figure 17A:
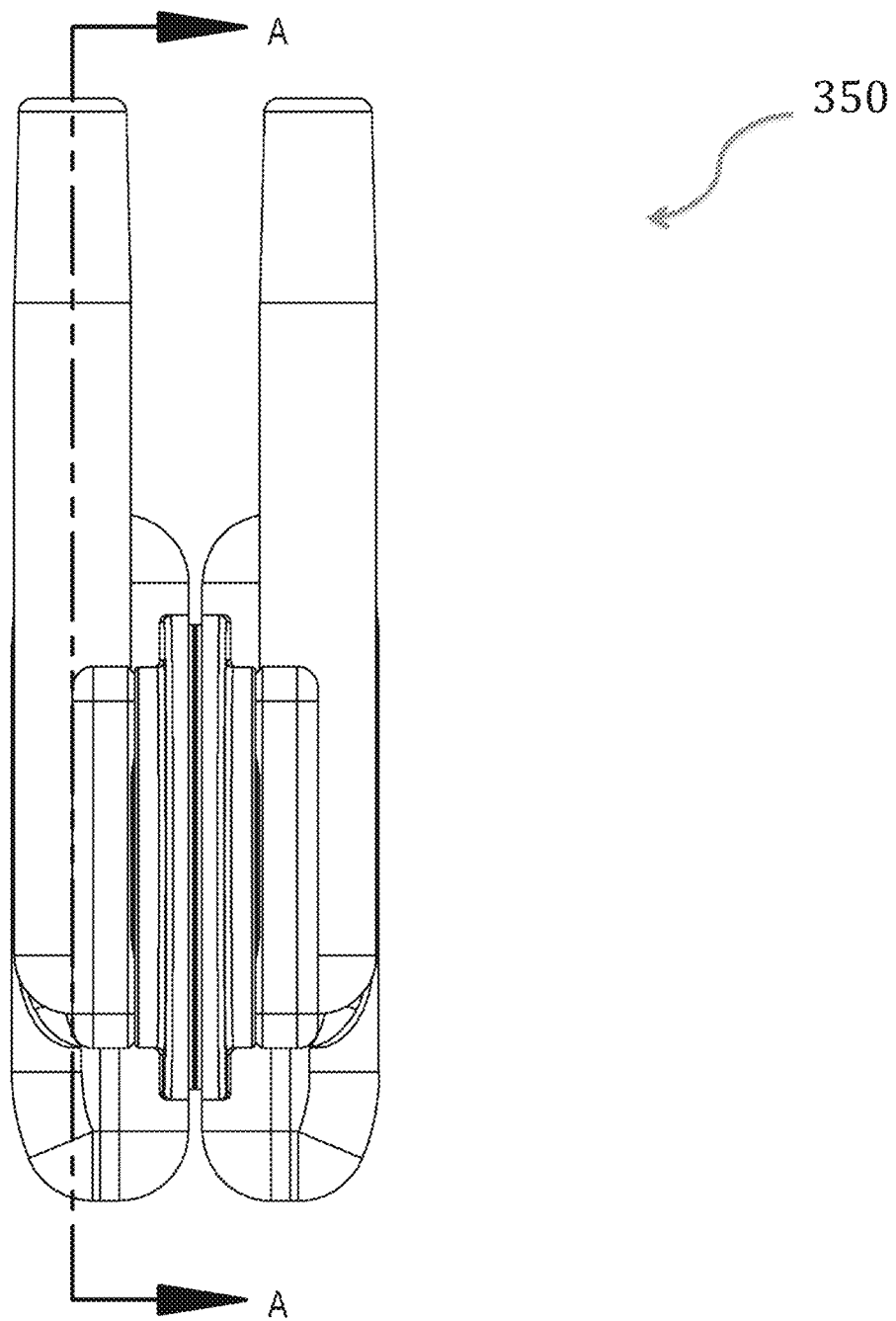
FIGS. 17A-17B illustrate a back view and sectional view, respectively, of a reservoir and inlet/outlet member of the cartridge system in accordance with another embodiment of the present invention.
Figure 17B:
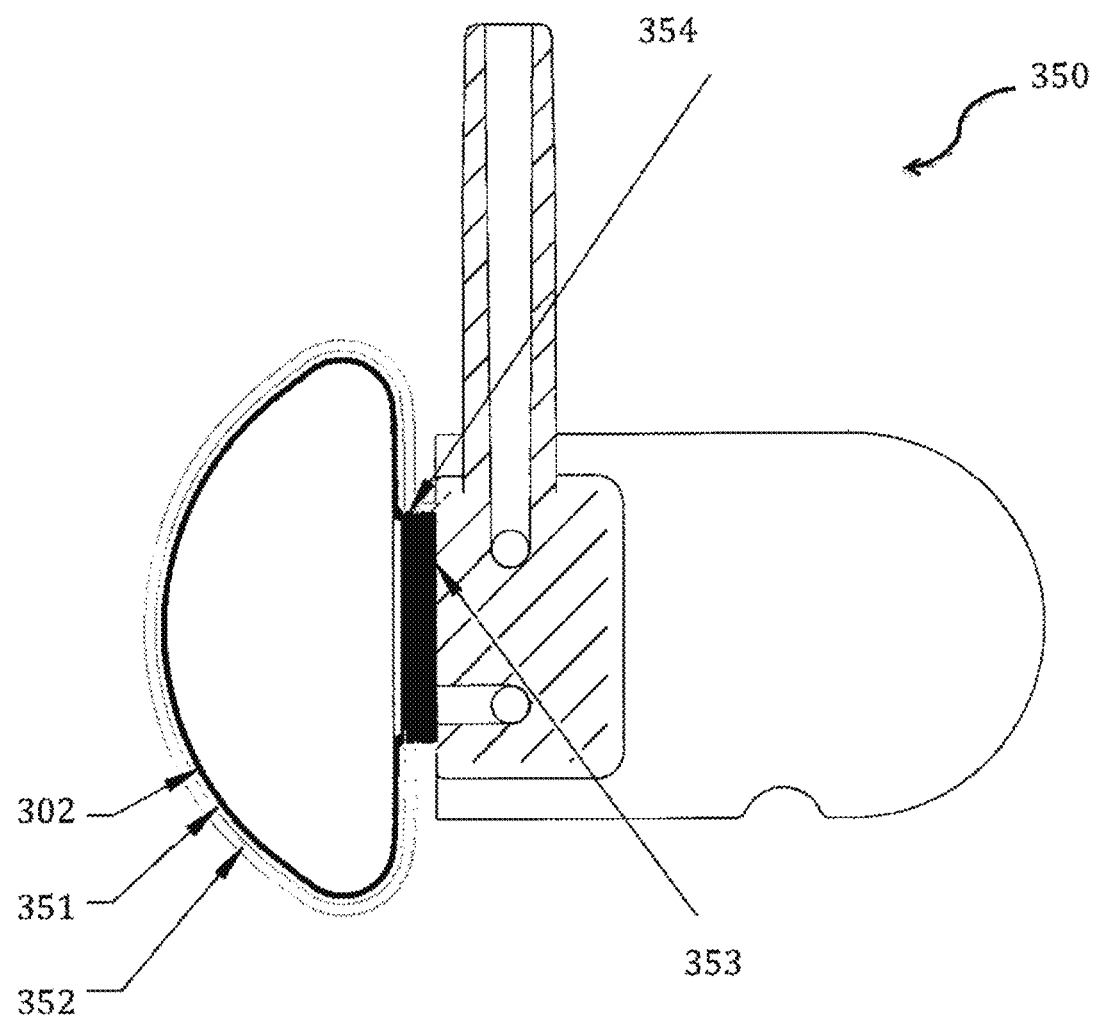

In yet another preferred embodiment of the invention, as shown in FIGS. 17A-17B, the cartridge assembly 350 includes the reservoir 302 mounted within a reservoir shell 352. The inside of the reservoir shell 352 is provided with an insulation and sealed layer 351 that enables temperature control of the fluid medicament within the reservoir 302. A cap 353 can be coupled, for example, through molding 354, to the inner wall 302d near the opening 302c. The reservoir shell 352 is coupled to the cap 353 and the cap 353 is securely engaged to a male part of the inlet/outlet members 307, 307' (FIGS. 16A-16D).

Figure 17C:
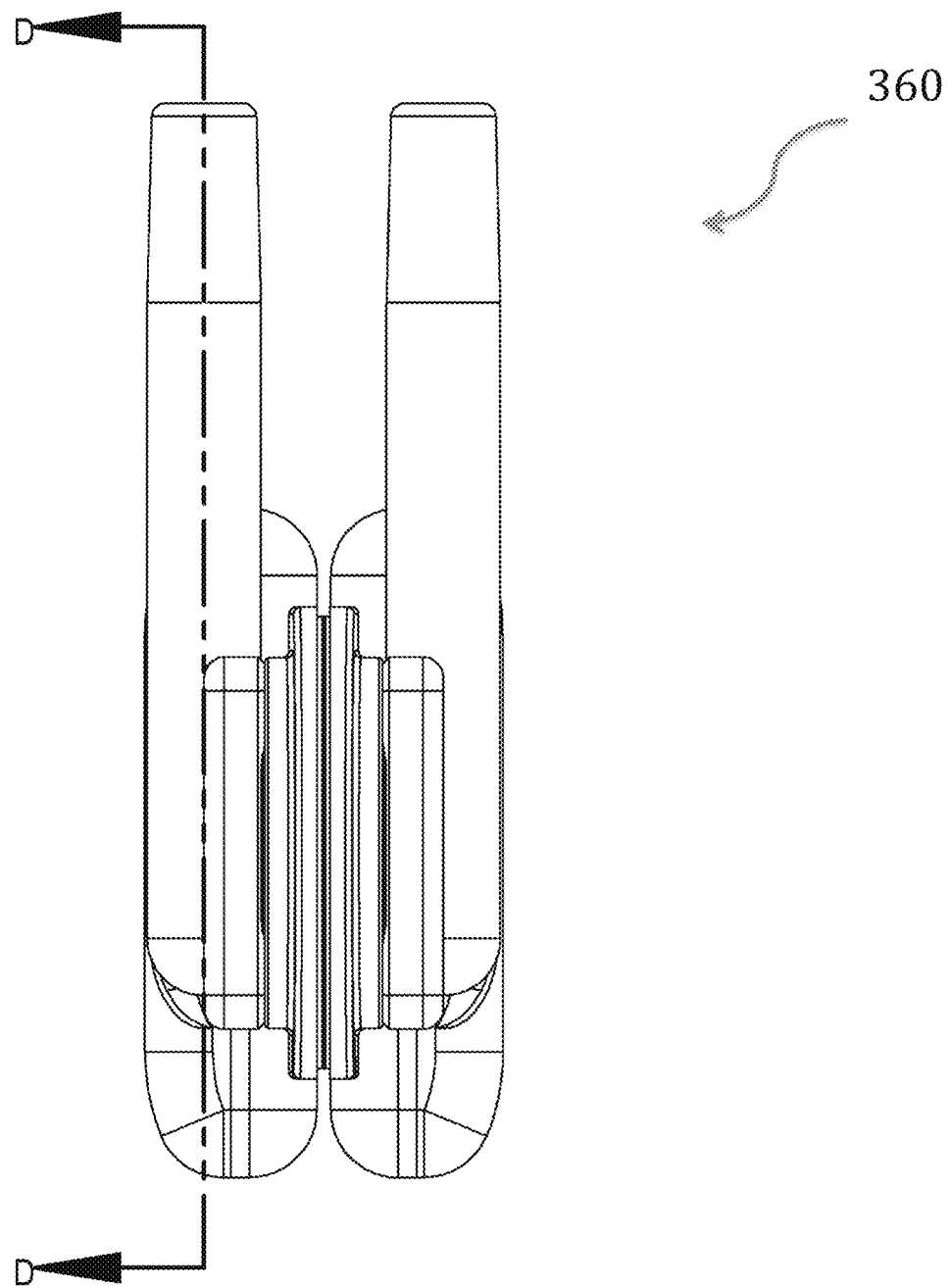
FIGS. 17C-17D illustrate a back view and sectional view, respectively, of a reservoir and inlet/outlet member of the cartridge system in accordance with yet another embodiment of the present invention.
Figure 17D:
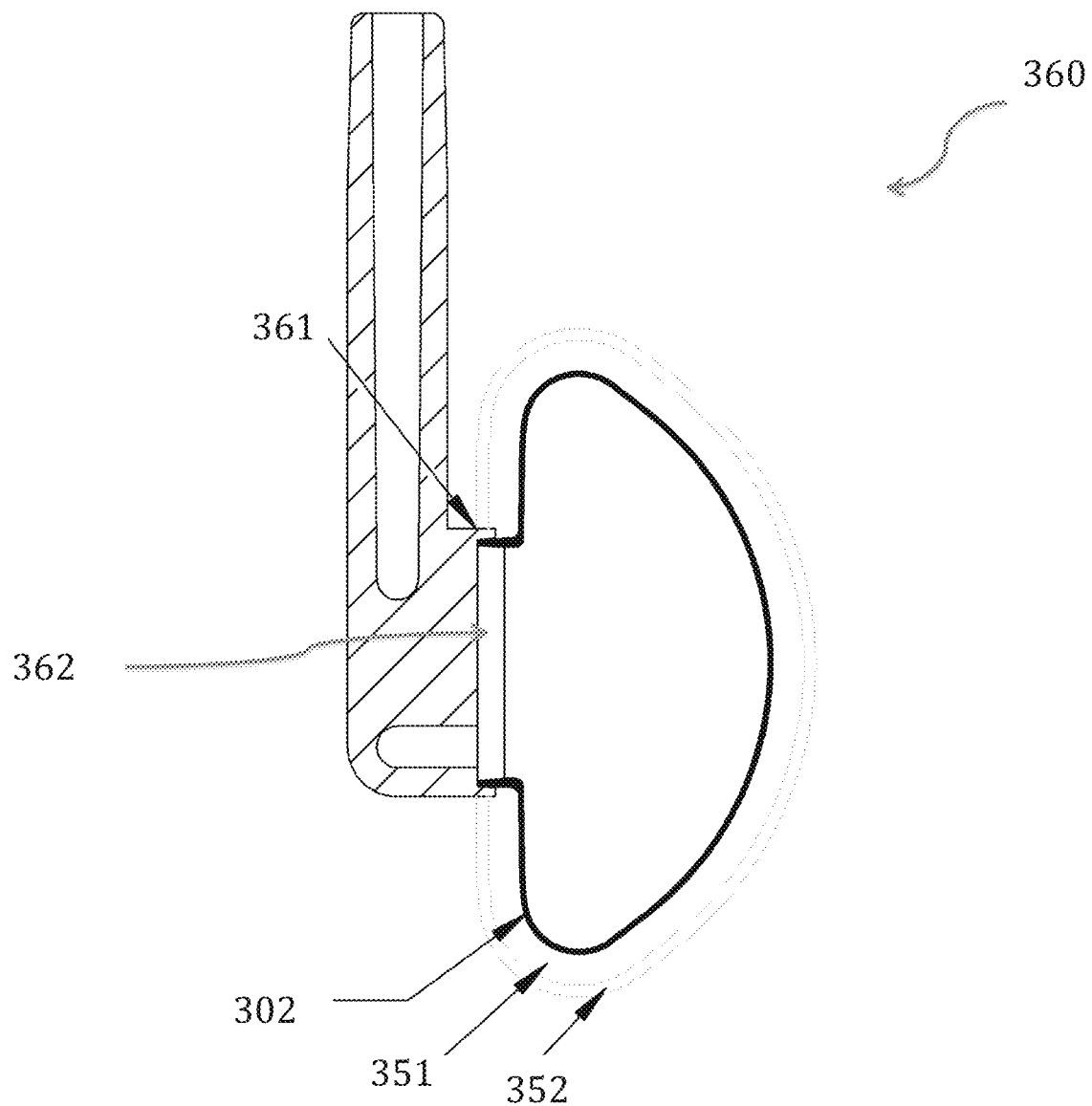

In yet another preferred embodiment of the invention, as shown in FIGS. 17C-17D, the cartridge assembly 360 includes the reservoir 302 mounted within a reservoir shell 352. The inside of the reservoir shell 352 is provided with an insulation and sealed layer 351 that enables temperature control of the fluid medicament within the reservoir 302. A cap 362 can be coupled to the inner wall 302d near the opening 302c. The reservoir shell 352 is coupled to the cap 362 and the cap 362 is threadedly 361 engaged to a male part of the inlet/outlet members 307, 307' (FIGS. 16A-16D).

It is to be understood that the reservoirs 302, 302' mounted within a reservoir shell 352 having an insulation and sealed layer 351 or without the reservoir shell 352 can include a cap for removably closing the opening 302c. The reservoirs 302, 302' may be designed to work with any drug delivery device for delivery of medicaments. Additionally, the drug delivery device 100 can be equipped with a detection device that alerts the user when a new medication cartridge has been properly inserted and is ready for use.

Figure 12A:
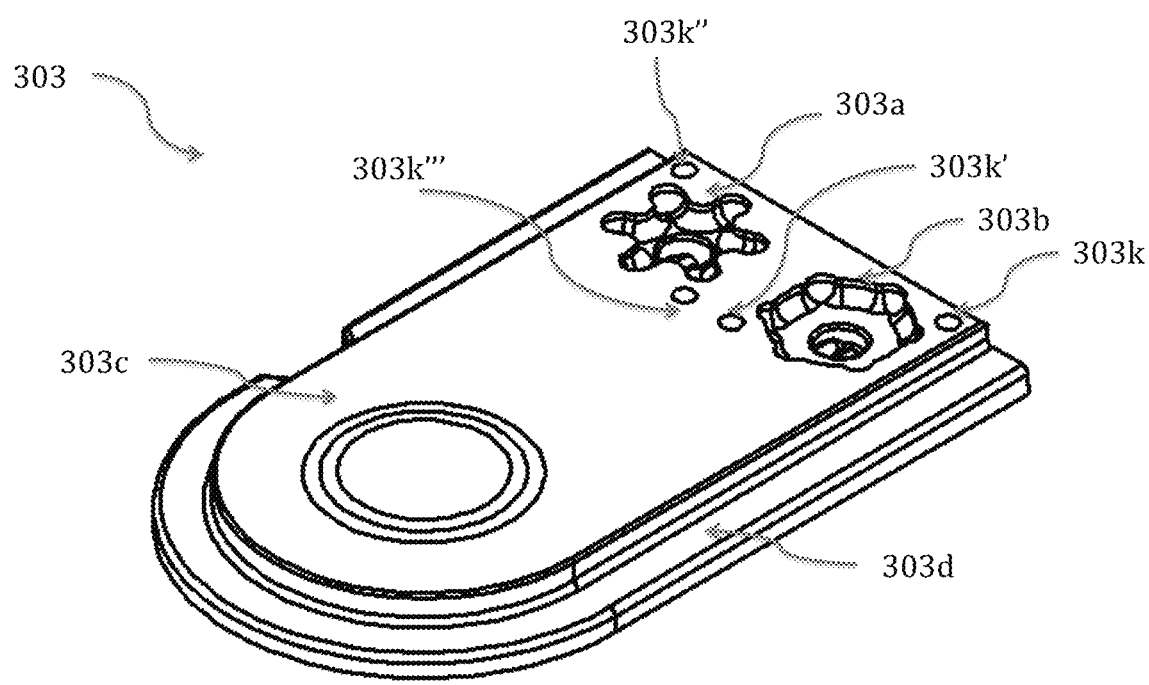
FIGS. 12A-12B illustrate a perspective view and bottom view, respectively, of a first pump body insert of the cartridge system in accordance with an embodiment of the present invention.
Figure 12B:
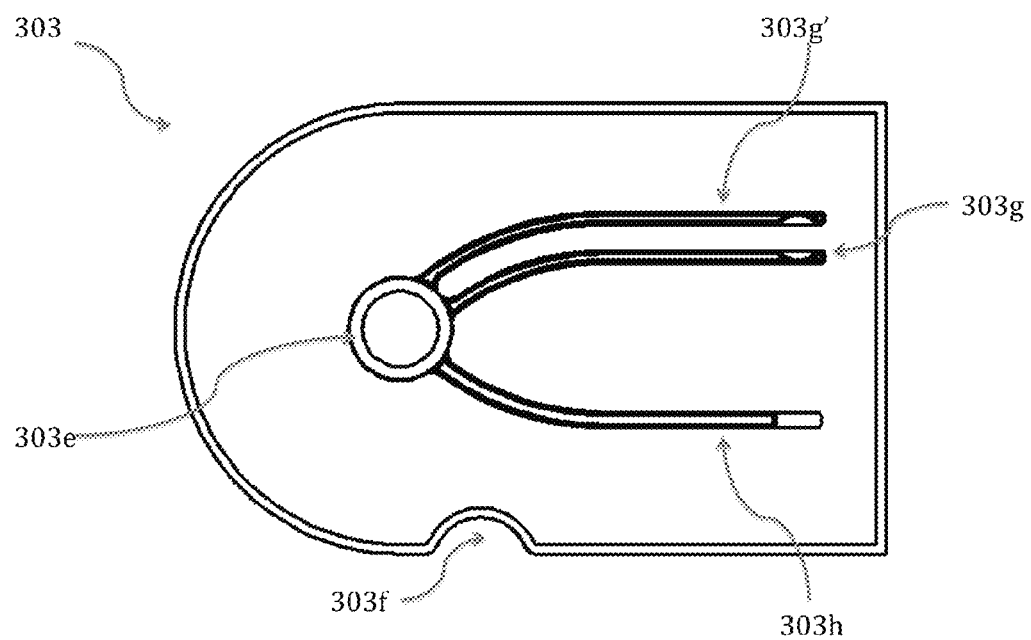
Figure 14:
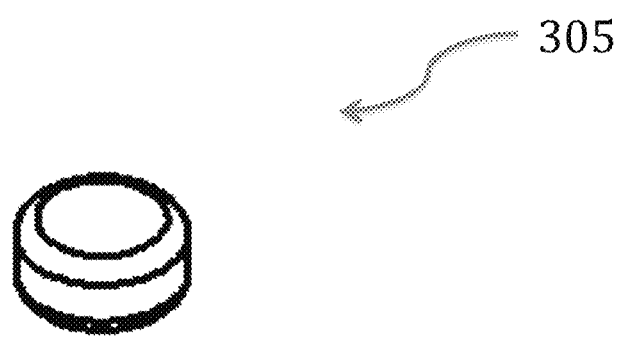
FIG. 14 illustrates a perspective view of a magnet of the cartridge system in accordance with an embodiment of the present invention.

Referring to FIGS. 12A-12B, a first pump body insert 303 having a fluid receiving opening 303a, and a fluid discharge opening 303b is shown. The first pump body insert 303 also includes a plurality of output channels 303g, 303g', for example, two output channels, and a plurality of input channels 303h, for example, one input channel. The plurality of output channels 303g, 303g' and the plurality of input channels 303h are in fluid communication with the fluid discharge opening 303b, and the fluid receiving opening 303a, respectively. The plurality of output channels 303g, 303g' and input channels 303h are designed to provide membrane support thereby preventing deformation and reverse flow of fluids. The first pump body insert 303 has an opening 303e to house a magnet 305 (FIG. 14). Apertures 303k, 303k', 303k'', 303k''' can be used to align and/or secure the first pump body insert 303 to other elements of the cartridge system 300.

Figure 12C:
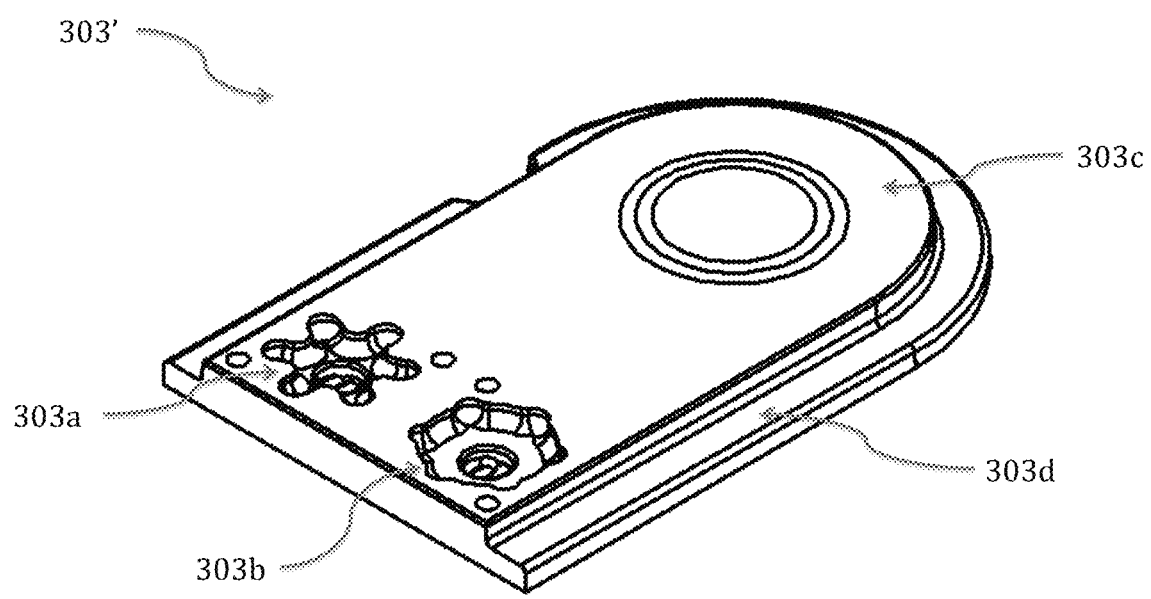
FIGS. 12C-12D illustrate a perspective view and bottom view, respectively, of a second pump body insert of the cartridge system in accordance with an embodiment of the present invention.
Figure 12D:
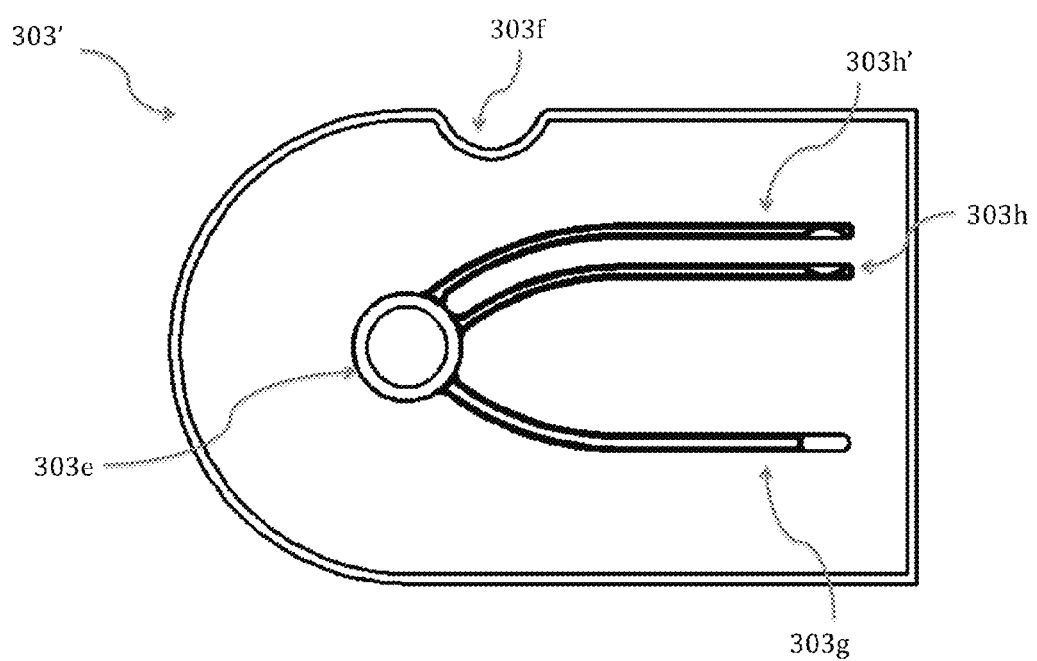

The second pump body insert 303', shown in FIGS. 12C-12D is substantially symmetrical in geometry to the first pump body insert 303 except having a plurality of output channels 303g, for example, one output channel, and a plurality of input channels 303h, 303h', for example, two input channels. The first pump body insert 303 and second pump body insert 303' are preferably made of clear polypropylene homopolymer or medical grade acrylic.

The cartridge system 300 has a pump membrane 304 as shown in FIG. 13. The pump membrane 304 is a bio-compatible elastomer membrane, preferably made of Silastic Q7-4840. The pump membrane 304 is placed between two disk magnets 305, shown in FIG. 14, which are housed within opening 303e of the first pump body insert 303 and the second pump body insert 303'. The disk magnets 305 are preferably gold-plated neodymium-iron-boron grade N42 magnets. The volume of flow of medicaments in the cartridge system 300 is related to the diameter of the magnets 305 and the stroke length. The stroke length may be electromagnetically controlled and monitored by a driver feedback system.

Referring to FIGS. 16A-16B, a first inlet/outlet member 307 having a fluid receiving opening 307d, and a fluid discharge opening 307c is shown. The inlet/outlet member 307 has a fluid outlet component 307a having a proximal end 307a'', a distal end 307a' and a cylindrical body connecting the distal and the proximal ends to form a hollow for receiving fluid medicament. In one embodiment, the proximal end 307a'' can preferably have a tapered end with a luer slip. The inlet/outlet member 307 includes a male part 307b that securely engages to the female part 302a of the reservoir 302. Apertures 307e, 307e', 307e'', 307e''' may be used to align and/or secure the first inlet/outlet member 307 to other elements of the cartridge system 300.

The second inlet/outlet member 307', shown in FIGS. 16C-16D is substantially symmetrical in geometry to the first pump body insert 307. Inlet/outlet members 307, 307' are preferably made of clear polypropylene homopolymer or medical grade acrylic.

The male part 307b of the inlet/outlet members 307, 307' can have tooth-like channels to ensure that a low resistance path for fluid flow exists for all configurations of the reservoirs 302, 302'. The reservoirs 302, 302', the pump body inserts 303, 303', the pump membrane 304, and the inlet/outlet members 307, 307' are securely engaged using housing units 308, 308' shown in FIGS. 19A-19C, 20A-20C.

Figure 15:
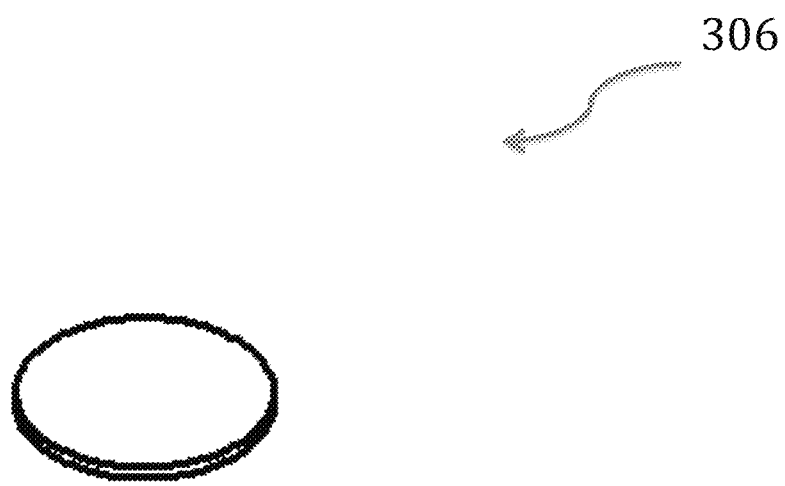
FIG. 15 illustrates a perspective view of a valve membrane of the cartridge system in accordance with an embodiment of the present invention.

Four valve membranes 306, shown in FIG. 15, preferably made of Silastic Q7-4840, are placed between (i) the fluid receiving opening 303a of the pump body inserts 303, 303' and the fluid receiving opening 307d of the inlet/out members 307, 307', and (ii) the fluid discharge opening 303b of the pump body inserts 303, 303' and the fluid discharge opening 307c of the inlet/out members 307, 307'. The introduction of the valve membranes 306 within said openings produce passive, one-way valves which direct fluid flow within the cartridge assembly 301.

When cartridge system 300 is assembled together, the first reservoir 302, the fluid receiving opening 307d of the first inlet/outlet member 307, the fluid receiving opening 303a of the first pump body insert 303, the plurality of inlet channels 303h and the plurality of outlet channels 303g, 303g' of the first pump body insert 303, the fluid discharge opening 303b of the first pump body insert 303, and the fluid discharge opening 307c and the fluid outlet component 307a of the first inlet/outlet member 307 are in fluid connection. Likewise, the second reservoir 302', the fluid receiving opening 307d of the second inlet/outlet member 307', the fluid receiving opening 303a of the second pump body insert 303', the plurality of inlet channels 303h, 303h' and the plurality of outlet channels 303g of the second pump body insert 303', the fluid discharge opening 303b of the second pump body insert 303', and the fluid discharge opening 307c and the fluid outlet component 307a of the second inlet/outlet member 307' are in fluid connection.

Figure 18A:
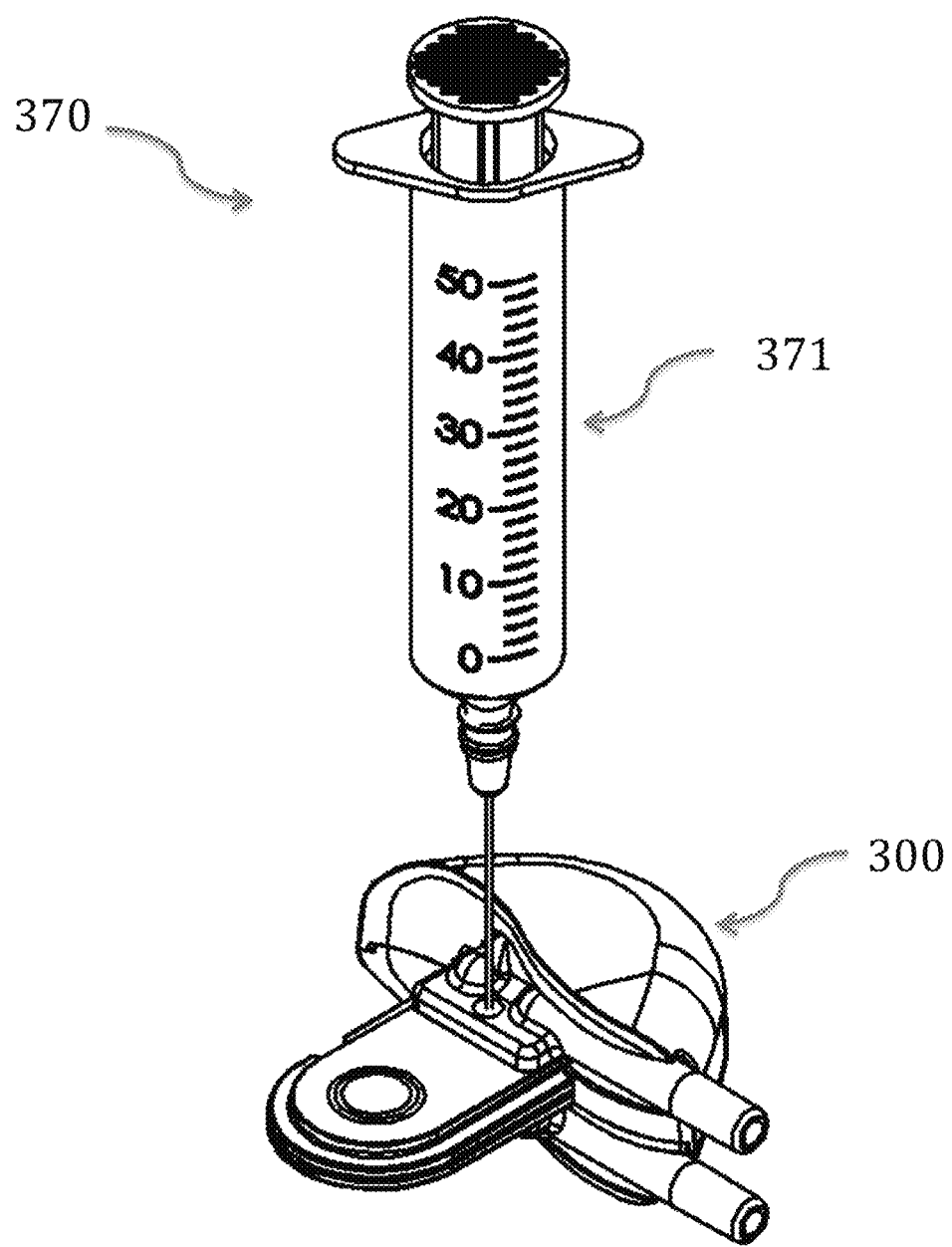
FIG. 18A illustrates a perspective view of a cartridge system, and a syringe, in accordance with another embodiment of the present invention.
Figure 18B:
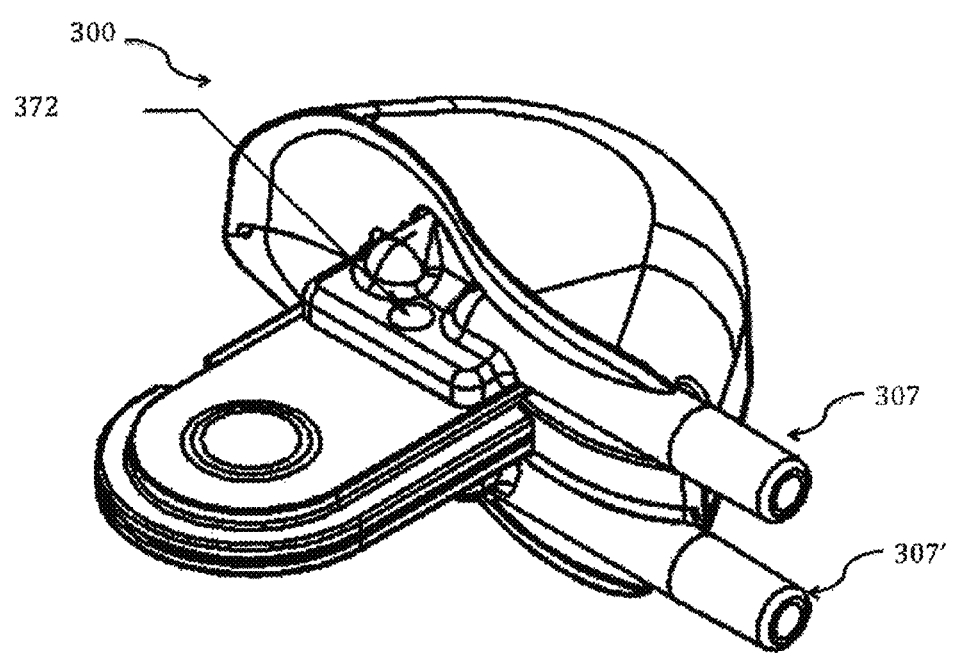
FIGS. 18B-18C illustrate perspective views of the cartridge system in accordance with another embodiment of the present invention.
Figure 18C:
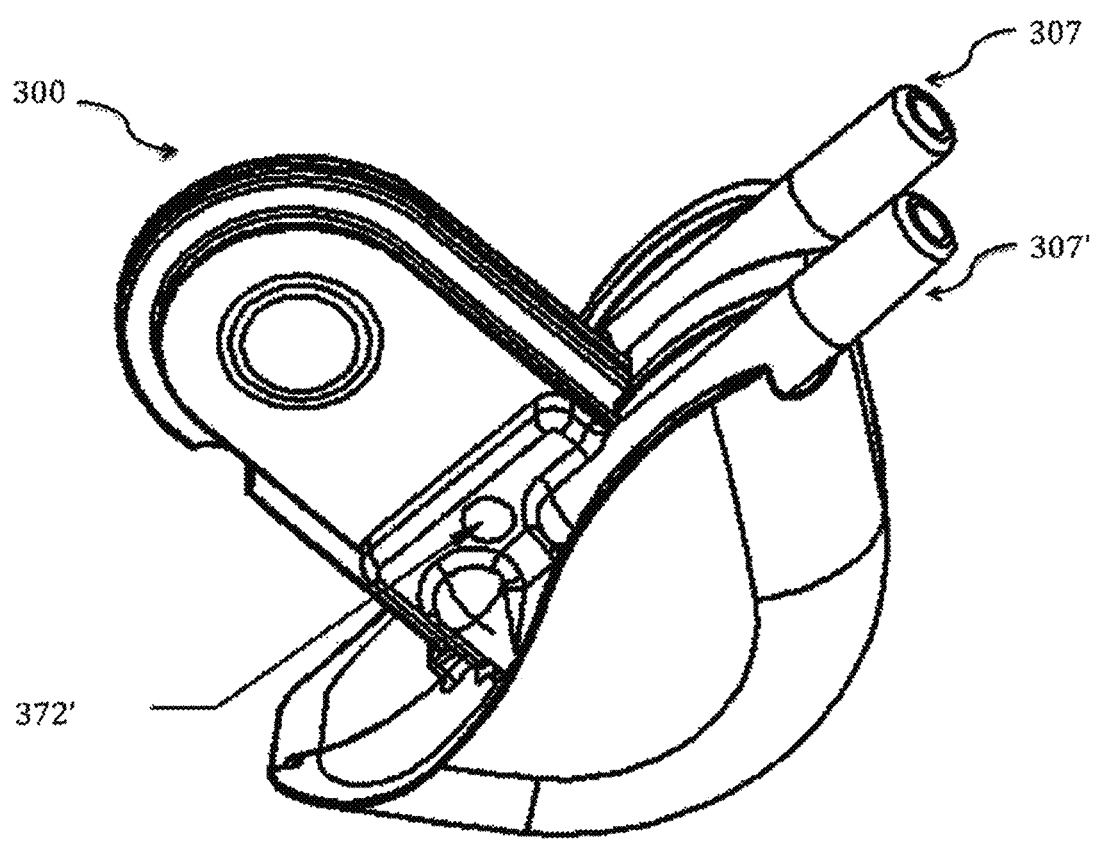
Figure 19A:
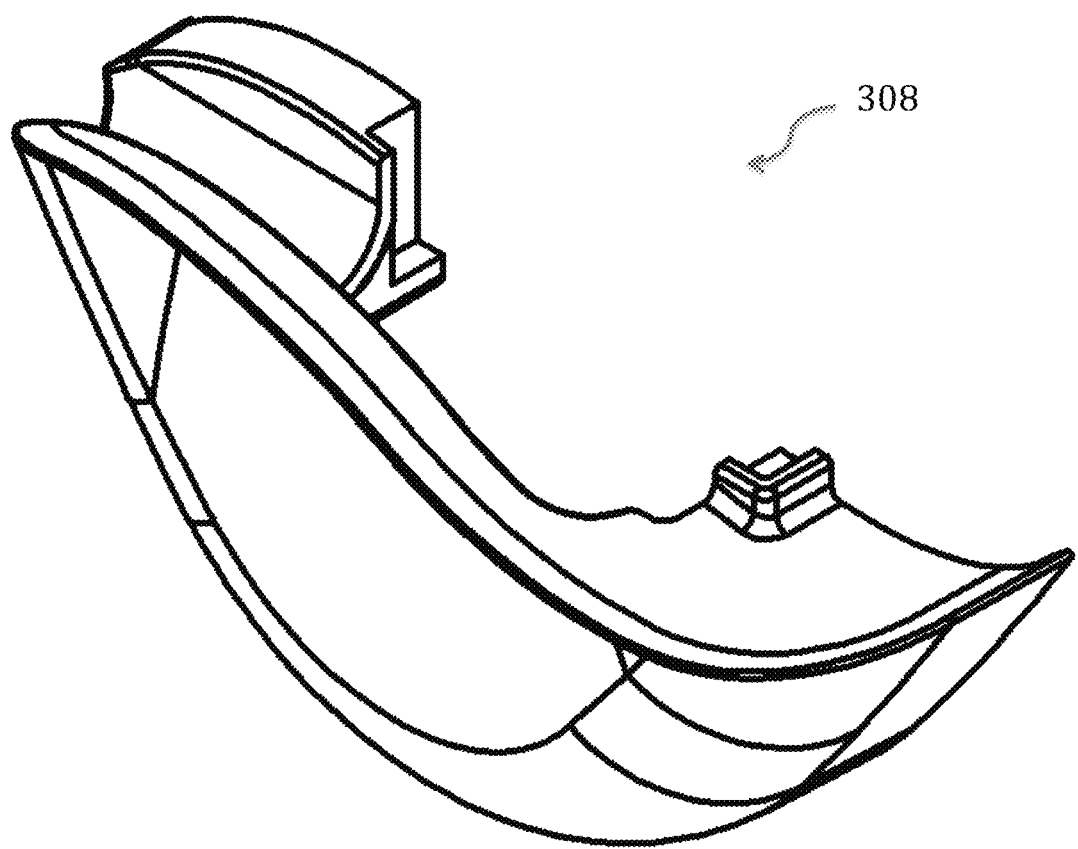
FIGS. 19A-19C illustrate a perspective view, front view and back view, respectively, of a front-bottom case of the cartridge system in accordance with an embodiment of the present invention.
Figure 19B:
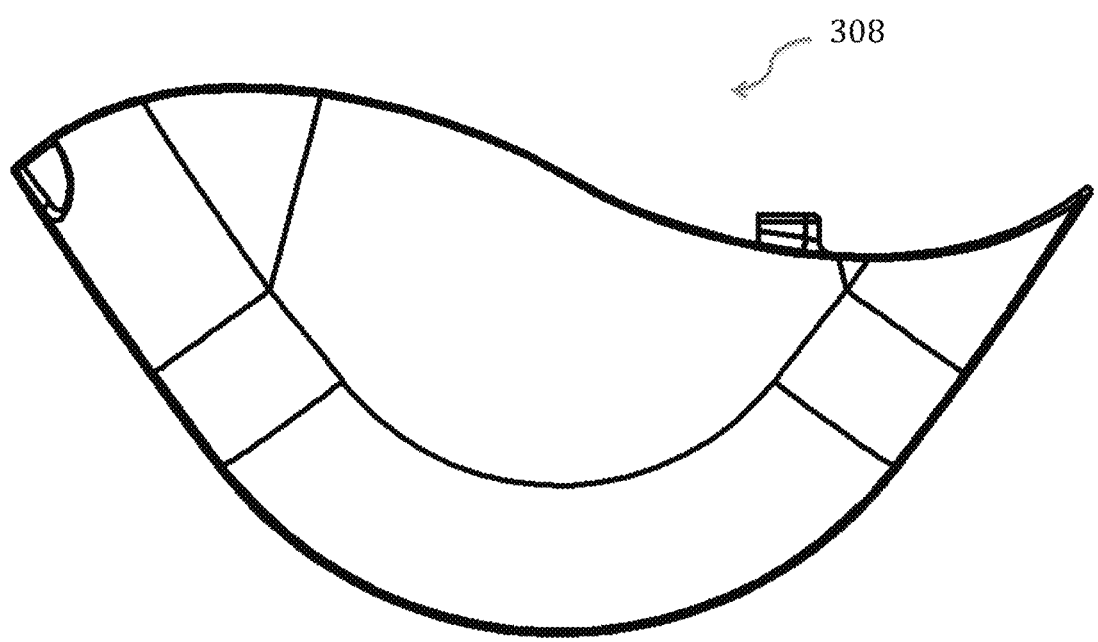
Figure 19C:
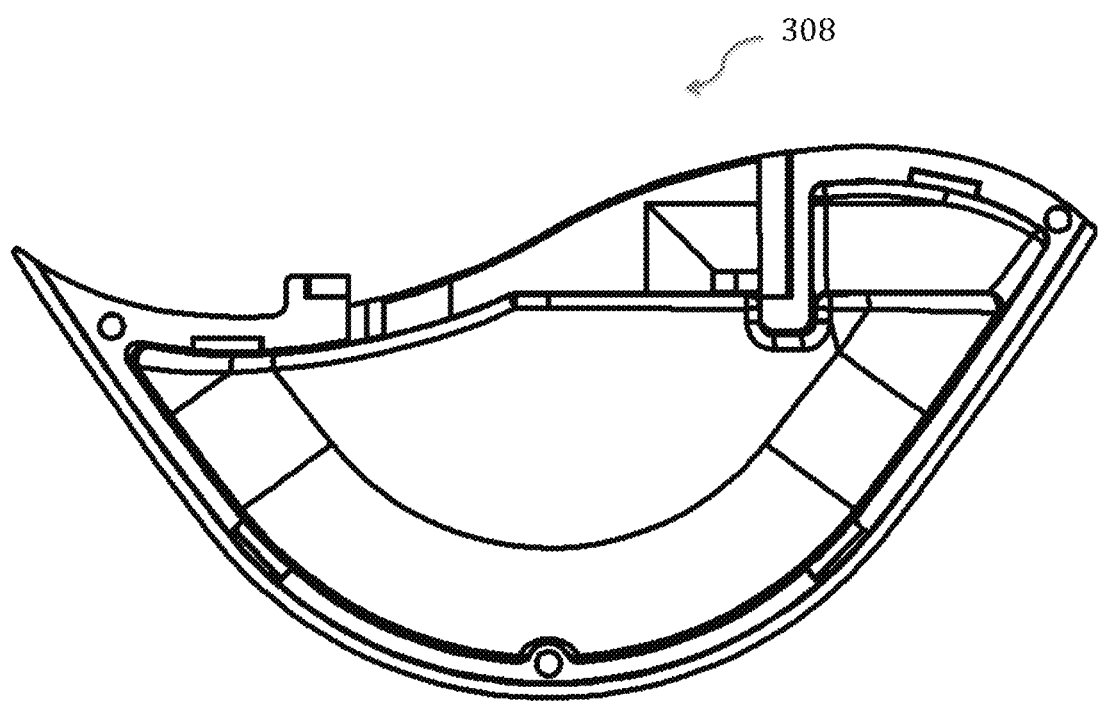
Figure 20A:
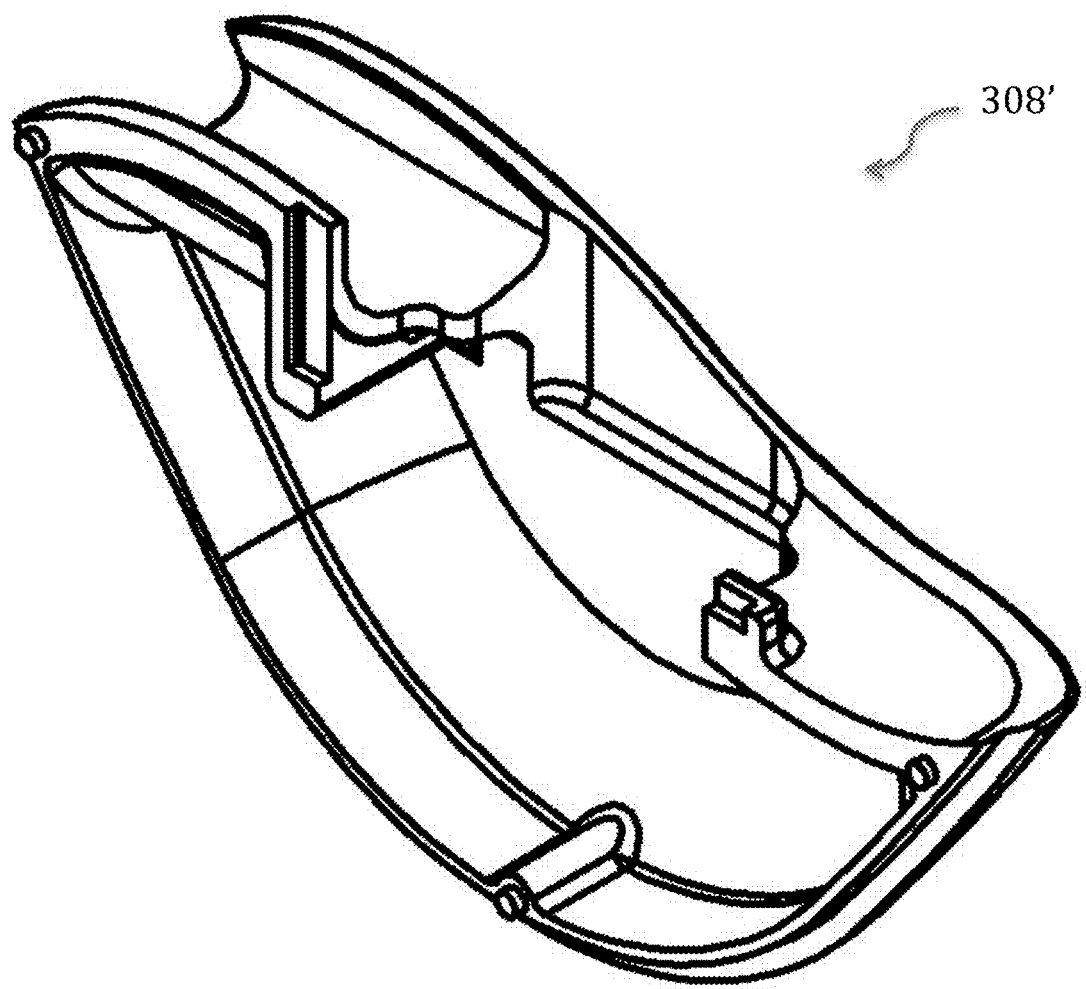
FIGS. 20A-20C illustrate a perspective view, front view and back view, respectively, of a rear-bottom case of the cartridge system in accordance with an embodiment of the present invention.
Figure 20B:
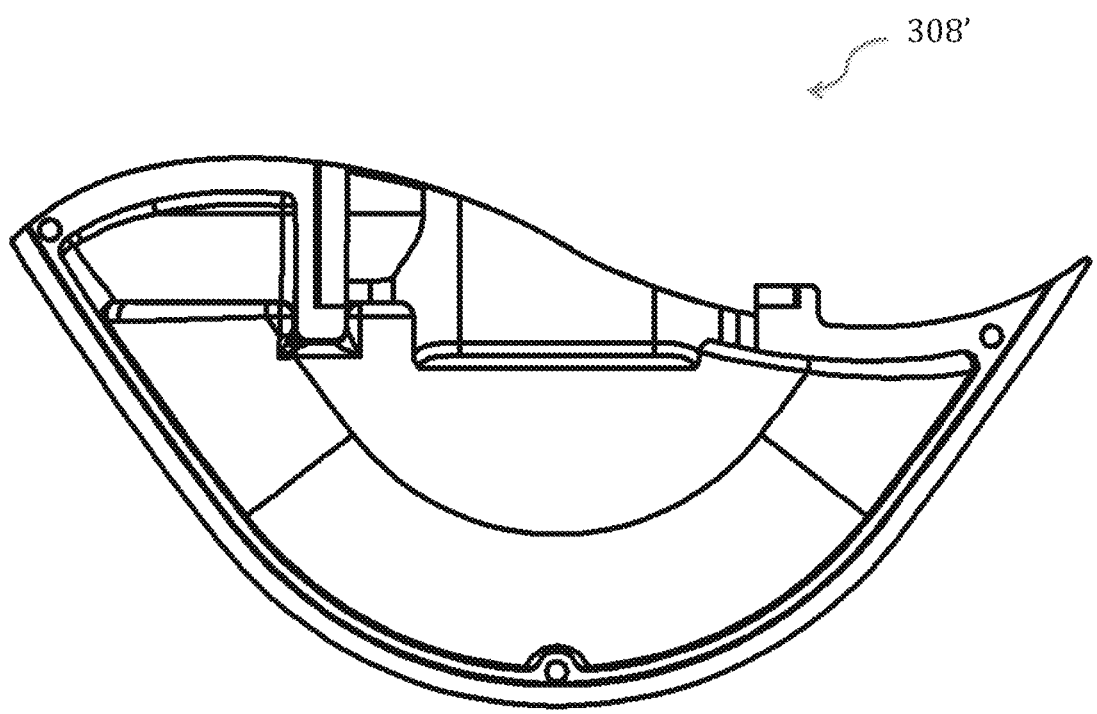
Figure 20C:
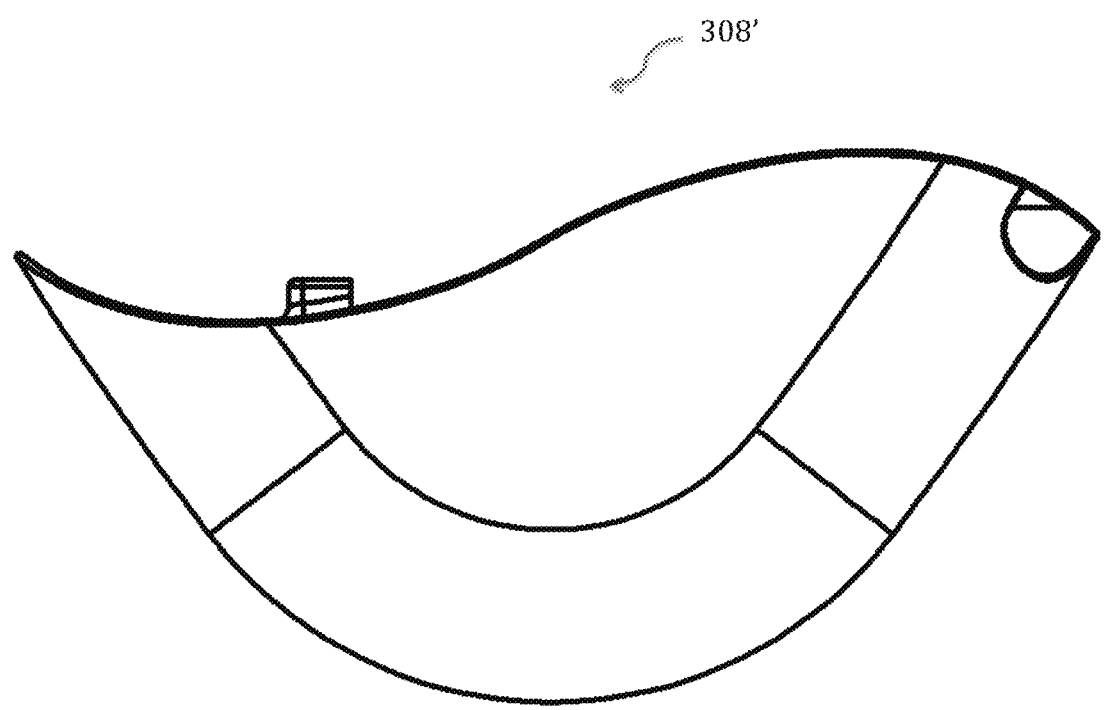

In another embodiment of the present invention, a system 370 is shown in FIG. 18A. Referring to FIG. 18A, in the system 370, the medicament can be filled in reservoirs 302, 302' of a cartridge system 300 using an instrument, for example, a syringe 371. Referring to FIGS. 18B-18C, the cartridge system 300 has orifices 372, 372' on the inlet/outlet members 307, 307' which are in fluid connection with reservoirs 302, 302', respectively.

Figure 21A:
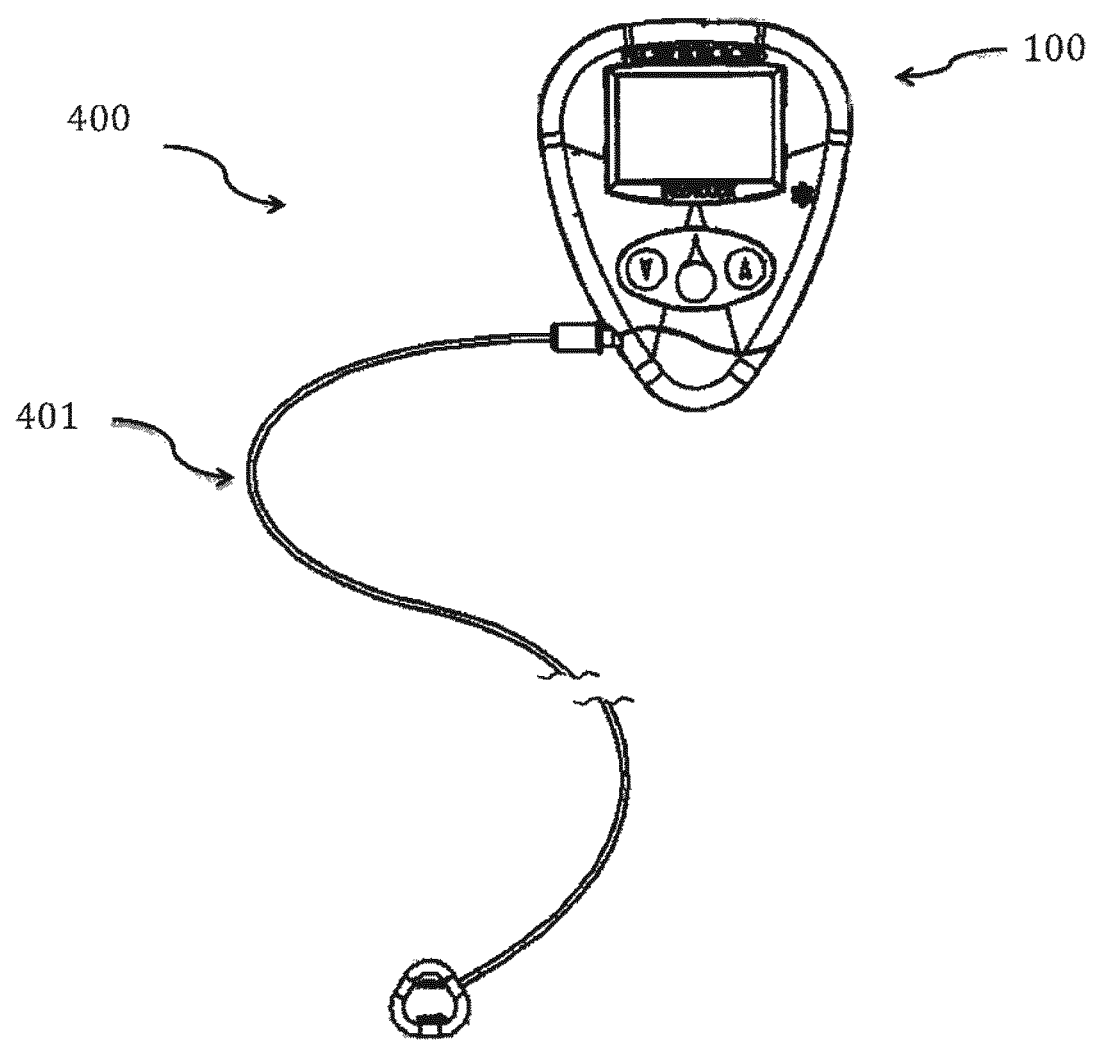
FIG. 21A-21B illustrate the drug delivery device with accessories, and the infusion set, respectively, in accordance with an embodiment of the present invention.
Figure 21B:
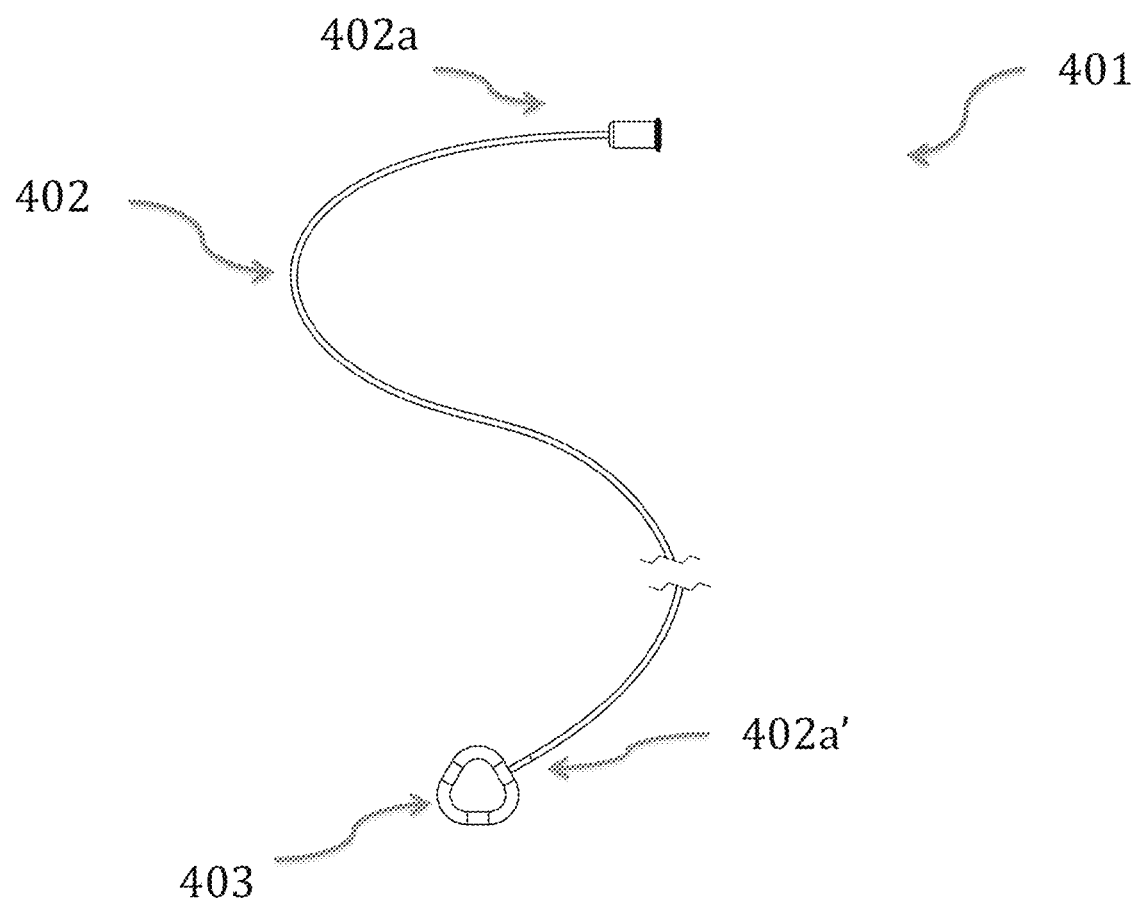

In a preferred embodiment of the present invention, shown in FIGS. 21A-21B, the drug delivery device 100 with an accessory 401 is shown. Preferably, the accessory 401 is an infusion set having a conduit 402 for delivering the fluid medicament from the drug delivery device 100. The conduit 402 is preferably, a single tube catheter or a Y-catheter. The distal end 402*a* of the conduit 402 is securely attached to a luer slip on the proximal end 307*a*" of the fluid outlet component 307*a* of the inlet/outlet member 307 in the cartridge system 300. The proximal end 402*a*' of the conduit 402 is securely engaged to a cannula and insertion mechanism 403 including a sensor and a needle. When the drug delivery device 100 uses two reservoirs 302, 302', the conduit 402 is preferably a duel tube Y-catheter whose distal ends 402*a* are securely attached to the luer slips on the proximal ends 307*a*" of the fluid outlet component 307*a* of the inlet/outlet member 307, 307'. The proximal end 402*a*' of the conduit 402 is securely engaged to a cannula and insertion mechanism 403 including a sensor and a needle whereby the two medicaments are mixed in the canola before entering the needle. In another method of delivering the medicament, multiple needles exist in the cannula and insertion mechanism 403 and the two medicaments are delivered through separate needles.

Referring to FIG. 21A, a drug delivery device 100 including a delivery pump system 200 and the cartridge system 300 is shown. The cartridge system 300 snaps into the delivery pump system 200 and is securely engaged to it. The delivery pump system 200 includes, among others, a driver, a controller, and a power source. The driver electromagnetically drives the magnets 305 that applies a force to the pump membrane 304 causing it to deflect resulting in precise volumetric delivery of the fluid medicament from the reservoirs 302, 302'. This deflection of the pump membrane 304 results in a change of pressure within the chambers of the reservoirs 302, 302' resulting in an outward flow of the fluid medicament contained within the reservoirs 302, 302'. The magnetic force applied by the driver onto the pump membrane 304 may be adjusted using the controller. The drug delivery device 100 may be powered by batteries or connected to a power outlet using an adapter, or other sources of power.

Figure 22:
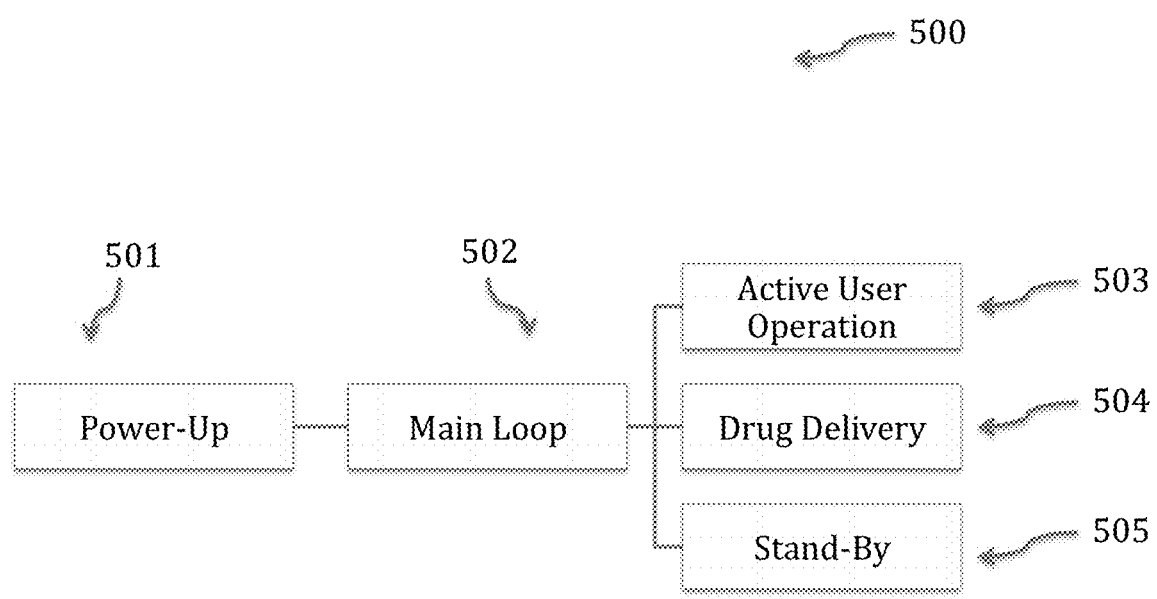
FIG. 22 illustrates a block diagram of the drug delivery device's mode of operation in accordance with an embodiment of the present invention.
Figure 23:
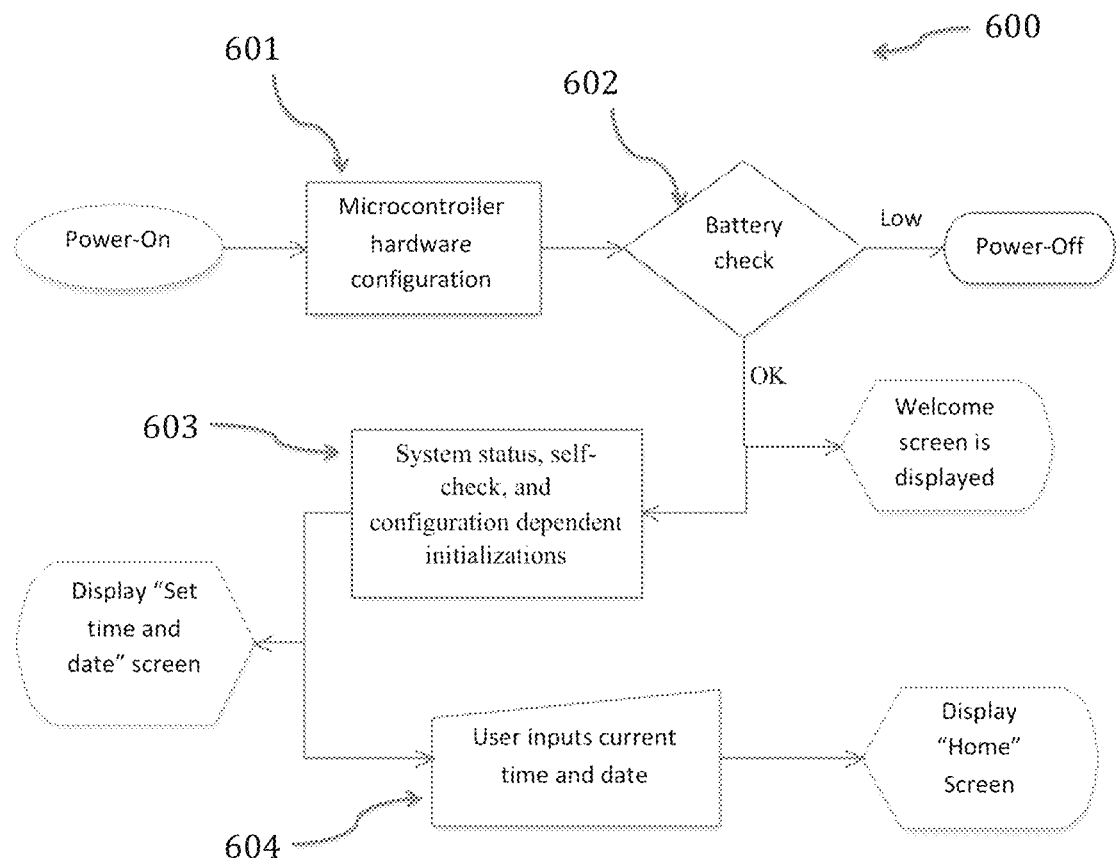
FIG. 23 illustrates a flow chart of the drug delivery device's power-up sequence in accordance with an embodiment of the present invention.

In a preferred embodiment of the invention, a machine-readable program stored within the microcontroller 208*c* of the delivery pump system 200 controls the operation of the drug delivery device 100. Preferably, the operation 500 can be subdivided into distinct modes, as shown in FIG. 22. Subsequent to providing the drug delivery device 100 with initial power, the drug delivery device 100 operates in a Power-Up 501 mode executing its Power-Up sequence 600, as shown in FIG. 23. By pressing the power button 208*f* on the delivery pump system 200, a user can trigger the microcontroller 208*c* to begin executing its Power-Up sequence 600.

In a preferred embodiment of the present invention, shown in FIG. 23, the Power-Up sequence 600 can be carried out in several steps. First, in step 601, the microcontroller hardware configuration for default power-up operation is set up including setting up the I/O ports, internal counters and timers, and initializing variables in volatile memory locations. Thereafter, the battery voltage is checked, in step 602. If the battery voltage is very low, for example, below 6.5V, a message is displayed on the screen indicating that the battery is dead. All peripherals, timers, and functions of the drug delivery device 100 are stopped and the drug delivery device 100 is shutdown. If the battery voltage is within operating range of 6.5V to 8.5V, power-up sequence execution is continued.

In step 603, the drug delivery device 100 performs a self-check, probes different portions of the system to obtain their status, and sets up the remainder of the configuration depended initializations. Next, the real-time clock is started and the display prompts the user to set the current time and date, in step 604. Finally, following the completion of the user setting the time and date, a "Home" screen is displayed and device operation moves from the Power-Up sequence 600 to execution of the Main Loop 502.

Figure 24:
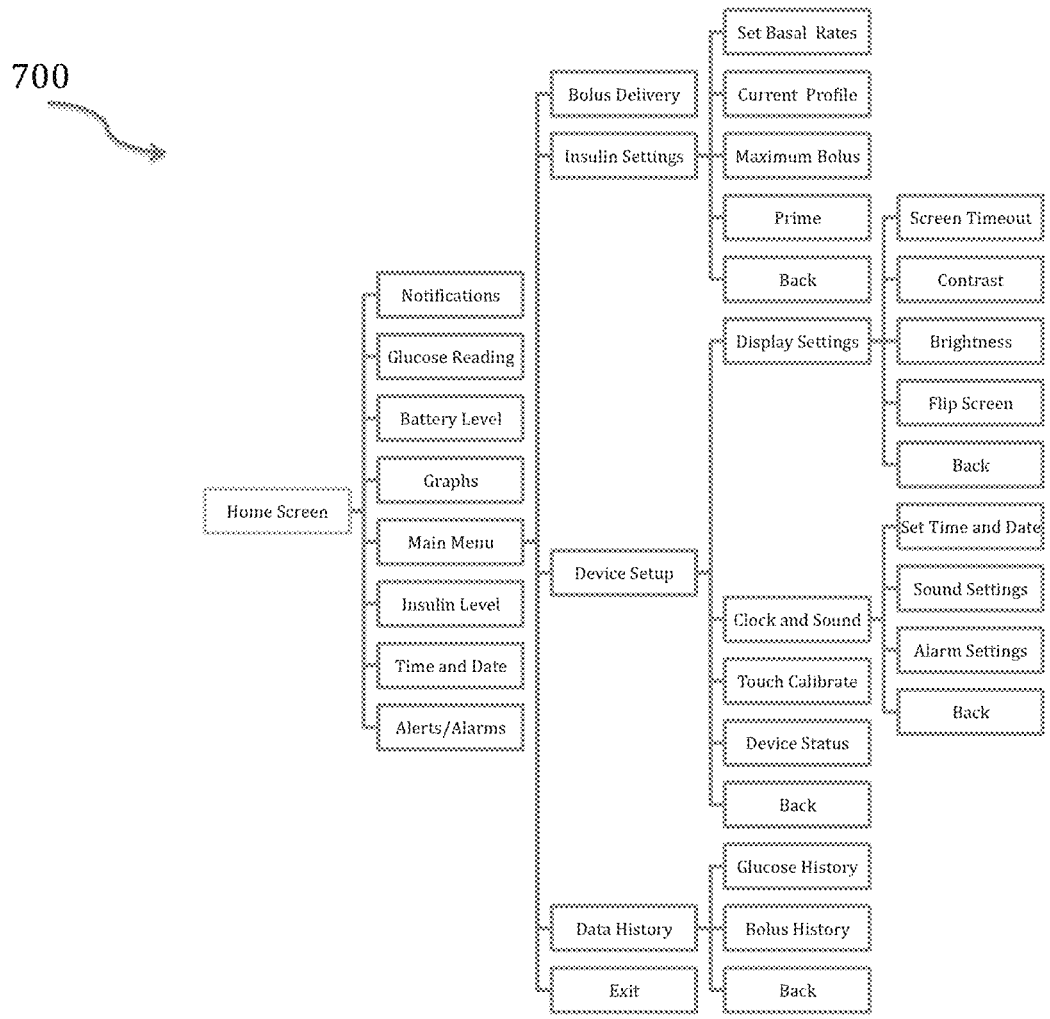
FIG. 24 illustrates a block diagram of the drug delivery device's operating system menu guide in accordance with an embodiment of the present invention.

In the "Main Loop" mode 502, the controller 208*c* executes code based on its current mode of operation. The "Home" screen is the screen that will be displayed most often to the user and displays various information, as shown in FIG. 24—time and date, insulin level in the reservoir(s), battery level, blood glucose reading, graphs of user selectable recorded data, main menu, alerts/alarms, and notifications. In one embodiment, the "Home" screen displays two graphs of user-selectable recorded data, an upper graph that displays the patient user's past blood glucose readings, and a lower graph that displays current basal profile. The patient user can toggle the lower graph between current basal profile and bolus history by pressing either the "Up" button 203*a* or the "Down" button 203*c*. The patient user can access the "Main Menu" by pressing the "Select/Enter" button 203*b* and can access various device settings and options from the "Main Menu" and its sub-menus that are hierarchically structured as shown in FIG. 24. The controller 208*c* runs the various checks and updates at regular intervals, for example, once per second and higher priority interrupts take precedence over checks and updates. For example, the drug delivery device 100 will pause the program from running checks and updates to deliver a basal delivery at a predetermined time.

The drug delivery device 100 can be programmed to deliver an appropriate bolus dose of insulin determined by the patient user's physician or caregiver. The patient user, patient user's physician, or patient user's caregiver may wish to set a maximum bolus dose that can be delivered by a single injection. This can be accomplished within the "Maximum Bolus" menu using the touch screen 204*c* or the "Up" 203*a* and "Down" 203*c* buttons. The bolus volume is displayed as a numerical amount as well as graphically in a syringe icon on the touch screen 204*c*. Once an appropriate bolus volume is selected, the patient user needs to press the "Select/Enter" button 203*b* to initiate administration of the bolus dose. The touch screen 204*c* will show a countdown and a graphical representation of the medicament being delivered.

The drug delivery device 100 operates by electromagnetically driving the magnets 305 on the pump membrane 304 in a reciprocating motion. The pump membrane 304 is deflected by the magnetic force between the electromagnetic coils 206 and the magnets 305 located on the pump membrane 304. As the magnets 305 and the pump membrane 304 are displaced, it results in a volumetric change within the pump chamber 303*e* resulting in fluid flow. This change in volume results in an increased pressure on one side of the pump membrane 304 and a pressure reduction on the other side. The pressure fluctuations drive a set of dynamic check valves installed along the flow process flow line. The valves are positioned to be directionally opposed, resulting in net flow of the fluid. The high-pressure side of the pump membrane 304 forces the corresponding intake valve closed and drives the fluid through the forward facing outlet valve. At the same time, the low-pressure side of the pump membrane 304 forces the opposing outlet valve closed and draws fluid in through the forward facing inlet valve. When the direction of the pump membrane 304 changes, the role of each chamber is reversed.

The deflection of the pump membrane 304 is controlled by an actuator assembly (not shown) magnetically coupled to it and a sensor configured to detect the pump membrane's 304 position. This actuator assembly includes a driver adjustable by the controller 208*c* that receives input from preferably three sensors, for example, Hall sensors (not shown) for spatial detection of the magnets' 305 position and preferably a single sensor if the magnets' 305 movements are linearly confined. The sensors can preferably be integrated within the pump housing 205 and oriented to only be sensitive to the radial component of the magnetic field (Br). They can preferably be positioned in an area where only the permanent magnet creates a non-negligible value of magnetic field (Br). The controller 208c regulates the motion of the magnets 305 based on flow rate requirements selected by the patient user. The magnetic force imparted on the pump magnets 305 and therefore on the pump membrane 304 results in volumetric stroke and flow of the medicament from the drug delivery device 100.

A patient can use the drug delivery device 100 along with the accessory 401 shown in FIG. 21A. In a method of delivering medicament using a drug delivery device 100, the drug delivery device 100 having the delivery pump system 200 and the cartridge system 300 is provided to the patient user. A plurality of pre-filled reservoirs 302, 302' containing fluid medicament are loaded to the cartridge system 300. The cartridge system 300 is then snapped into and securely engaged to the delivery pump system 200. The user then selects various parameters on a user interface on the delivery pump system 200. These parameters may include, but not be limited to, basal rate, insulin amount, bolus rate based on the calories of carbohydrates, protein, fat or fiber consumed, and the blood glucose level including the actual and target glucose levels. The user may either select pre-determined values or specify user-defined values for each of the parameters. The user connects an accessory, for example, an infusion set 401 to the drug delivery device 100.

The step of connecting an accessory, for example, an infusion set to the drug delivery device may include connecting the distal ends of a Y-catheter to the luer slips of the outlet component of the inlet/outlet members. Subsequently, the patient user can place an inset of the infusion set on a body part of the patient user, attach the infusion set to the body, and switch on the drug delivery device. When the patient user uses only one reservoir in the cartridge system, the step of connecting an infusion set to the drug delivery device may include connecting the distal end of the Y-catheter to the luer slip of the outlet component of the inlet/outlet member.

The delivery of medicaments may be at a controlled and continuous rate for a pre-determined or user-defined period of time. The delivery of medicament may also be at a programmable rate that is regulated by the patient. The drug delivery device may be preprogrammed to infuse medicaments at a constant basal rate or variable bolus rate over a certain period of time. The device can deliver micro-doses of medicaments—insulin, glucagon or other medication—at controlled and continuous rate for a pre-determined period of time.

The delivery of medicaments can be at a controlled and continuous rate for a pre-determined or user-defined period of time. Alternatively, the delivery of medicament can also be at a programmable rate that is regulated by the patient. The drug delivery device can be preprogrammed to infuse medicaments at a constant basal rate or variable bolus rate over a certain period of time. The device can deliver micro-doses of medicaments—insulin, glucagon or other medication—at controlled and continuous rate for a pre-determined period of time.

In another method of delivering medicament using the drug delivery device 100 having the delivery pump system 200 and the cartridge system 300, the drug delivery device 100 is provided to the patient user. A plurality of reservoirs 302, 302' are loaded to the cartridge system 300 and the reservoirs 302, 302' are filled with medicaments using an instrument, for example, a syringe. The cartridge system 300 is then snapped into and securely engaged to the delivery pump system 200. The patient user then selects various parameters on a user interface on the delivery pump system 200. These parameters may include, but not be limited to, basal rate, insulin amount, bolus rate based on the calories of carbohydrates, protein, fat or fiber consumed, and the blood glucose level including the actual and target glucose levels. The patient user can either select pre-determined values or specify user-defined values for each of the parameters. The patient user connects an infusion set having accessory 401 to the drug delivery device 100. Subsequently, the patient user can place an inset of the infusion set on a body part of the patient user, attach the infusion set to the body, and switch on the drug delivery device 100.

Figure 25A:
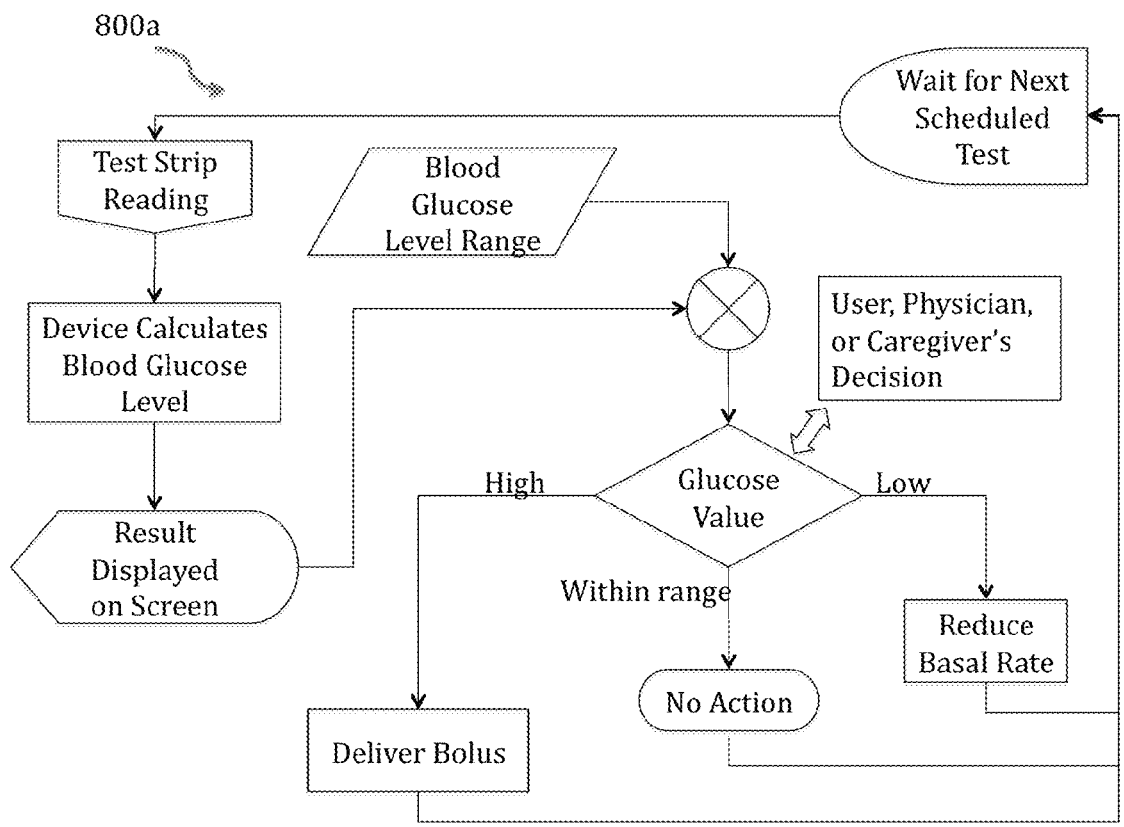
FIGS. 25A-25B illustrate flow charts of the drug delivery device's glucose feedback control using discrete test strips, and using continuous sampling, respectively in accordance with an embodiment of the present invention.

In another method of delivering medicament using the drug delivery device 100 of the present invention, the patient user measures his or her blood glucose level by inserting a test strip into the strip connector 208a housed on the circuit board 208 of the delivery pump system 200. The patient user applies a blood sample to the test strip, the integrated glucose meter automatically senses the application of blood, and subsequently calculates blood glucose level, as illustrated in FIG. 25A. The data result is automatically transmitted to the controller 208c and the data result is displayed on the touch screen 204c. If the blood glucose level is within a pre-determined range (the range having a low-end and a high-end), then no action is needed. If the glucose level is higher than the high-end of the range, a bolus dose of insulin can be administered either by the patient user manually with the depression of the delivery button, or automatically by pre-programming the drug delivery device 100. If the glucose level reading indicates that it is lower than the low-end of the range, the patient user can manually reduce the basal insulin level, or the drug delivery device 100 can be programmed to do this automatically. Thus, the drug delivery device 100 can sample and analyze a blood glucose test strip, and calibrate and display blood glucose value based on the analysis.

Typically, the normal blood glucose levels are as follows: fasting blood glucose (70-99 mg/dL), 2-hours after eating (70-145 mg/dL), and random (70-125 mg/dL). A fasting blood glucose level below 40 mg/dL in women or below 50 mg/dL in men are considered low values while a fasting blood glucose level of 126 mg/dL or higher is considered a high value.

Figure 25B:
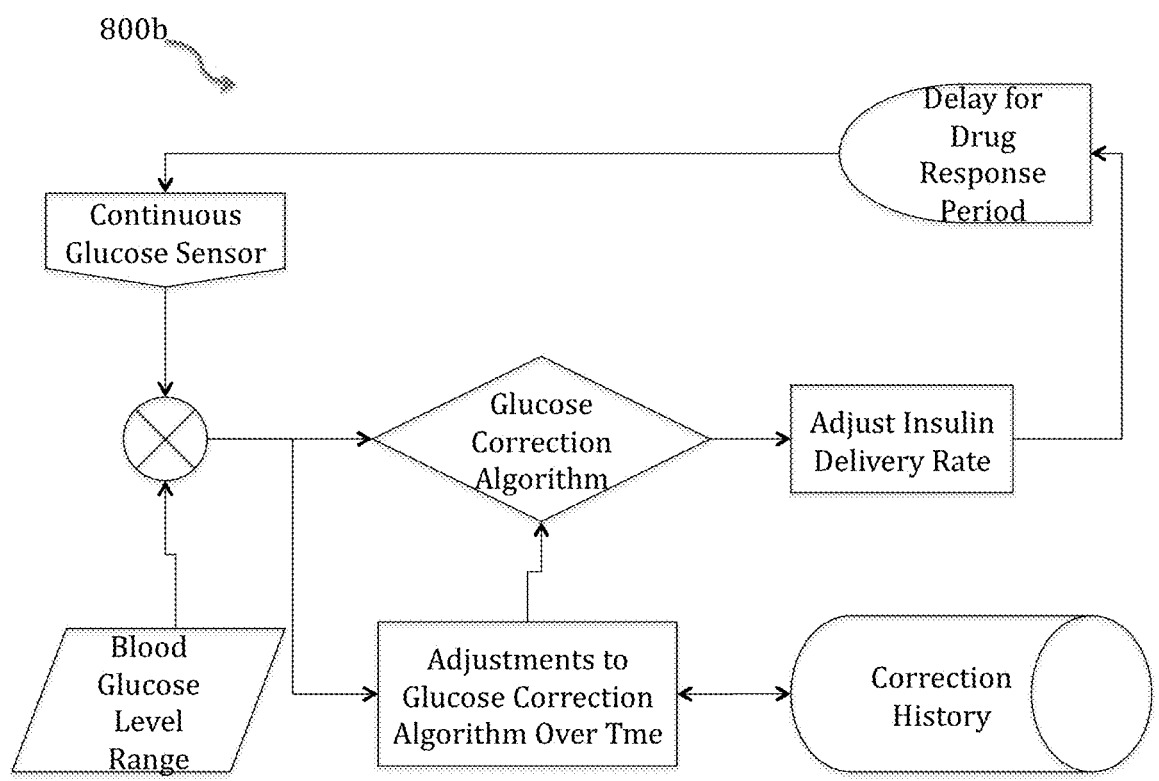

In another method of delivering medicament using the drug delivery device 100 of the present invention, the patient user measures his or her blood glucose level on a continuous basis, at pre-determined time intervals, using a continuous glucose sensor that calculates blood glucose level. The data result is automatically transmitted to the controller 208c and the data result is displayed on the touch screen. A glucose correction algorithm, illustrated in FIG. 25B, adjusts the insulin delivery rate based on the blood glucose level and a patient user-determined blood glucose level range. If the blood glucose level is within a pre-determined range (the range having a low-end and a high-end), then no action is needed. If the glucose level is higher than the high-end of the range, a bolus dose of insulin is administered automatically by the drug delivery device 100. If the glucose level reading indicates that it is lower than the low-end of the range, the drug delivery device 100 is programmed to automatically reduce the basal insulin level.

When the drug delivery device 100 is programmed, the controller 208c determines the basal or bolus rate and this data then becomes part of the algorithm that delivers the appropriate dose of medicament through an attached infusion set 401 (FIG. 21B) into the patient user's body. The controller 208c administers proper dosages based on twenty-four (24) basal rate values in units per hour that the patient user must determine with the help of a physician or caregiver. These values are then entered into the controller 208c prior to using the drug delivery device 100 for delivery of medicament. To enter these values manually, the patient user must press the "Select/Enter" button 203b on the membrane switch 203 to access a Main Menu screen, then follow the menu hierarchical structure to navigate to the "Set Basal Rates" menu. The patient user can enter each of the basal hourly rates by pressing the "Up" button 203a to increase a numerical value or the "Down" button 203c to increase the numerical value. When all twenty-four (24) hourly rates are entered, the controller 208c will return to the "Home" screen. The pump is then ready to deliver medicament automatically based on the data entered.

Figure 26A:
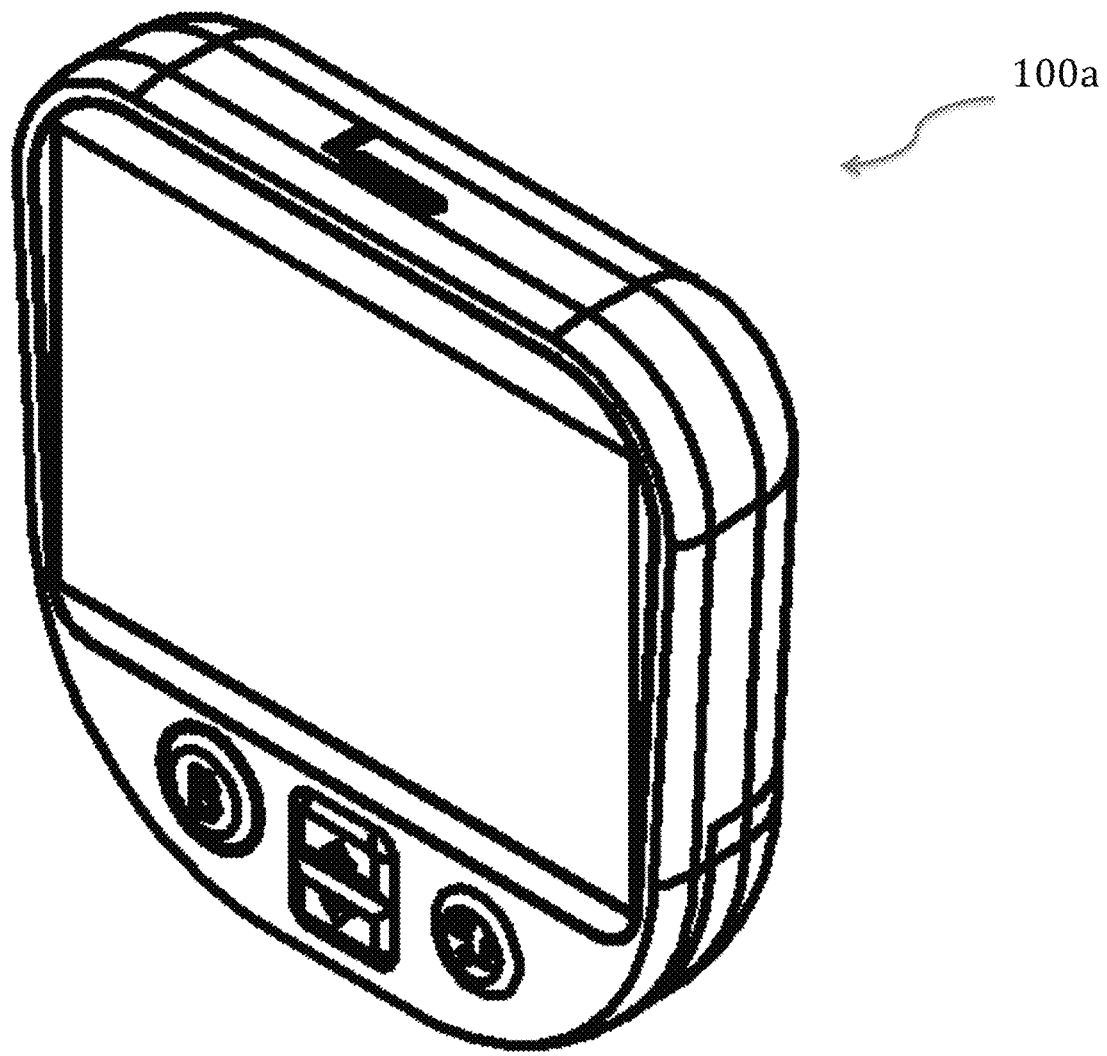
FIGS. 26A-26B illustrate a perspective view of a drug delivery device comprising a delivery pump system and a cartridge system in accordance with another embodiment of the present invention.
Figure 26B:
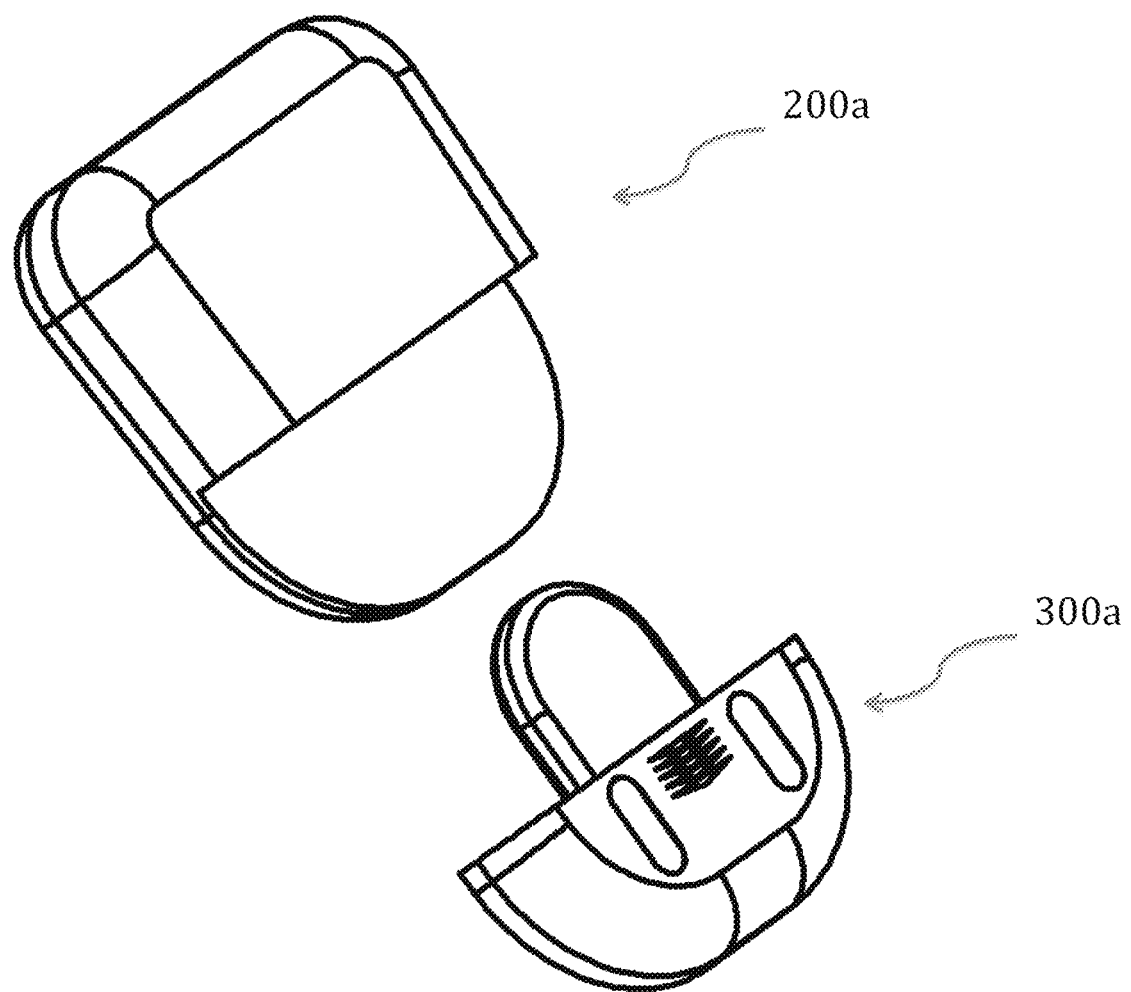

In another preferred embodiment of the invention, as shown in FIGS. 26A-26B, a drug delivery device 100a includes a delivery pump system 200a and a cartridge system 300a. The overall dimensions of the drug delivery device 100a are preferably 2.0" (length)×2.0" (width)×0.5" (thickness). In this embodiment, the drug delivery device 100a allows for insertion and removal of the cartridge system 300a in the rear. The single degree of freedom of the cartridge system 300a allows for easier insertion of the cartridge system 300a to the delivery pump system 200a. The delivery pump system 200a has a larger screen due to reduction in the slope of the front panel. The delivery pump system 200a has a button for direct access to bolus by a user enabling faster bolus delivery. The drug delivery device 100a has a plurality of windows that enable the user to view the medicament(s) and/or the various elements of the delivery pump system 200a and the cartridge system 300a.

Figure 27A:
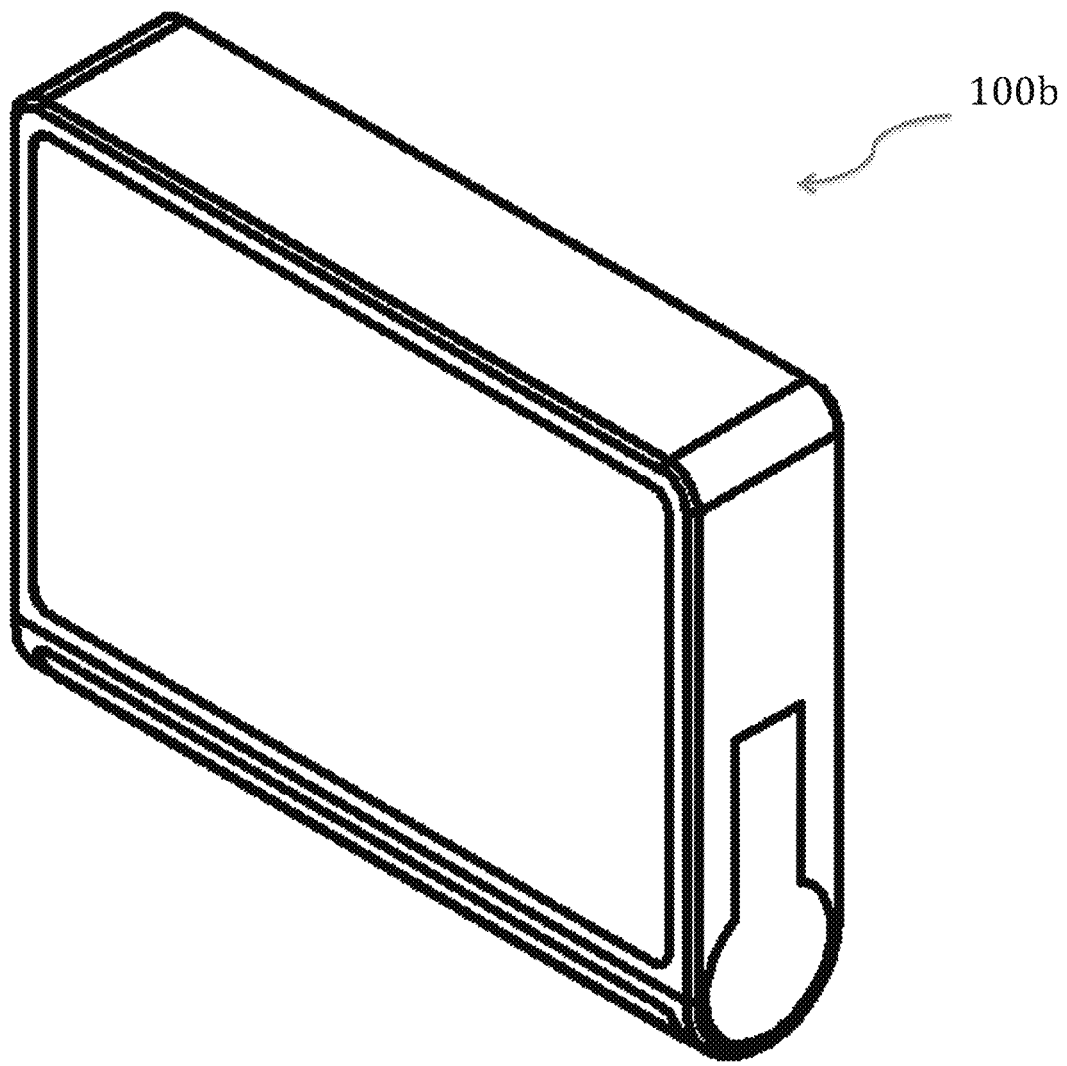
FIGS. 27A-27B illustrate a perspective view of a drug delivery device comprising a delivery pump system and a cartridge system in accordance with another embodiment of the present invention.
Figure 27B:
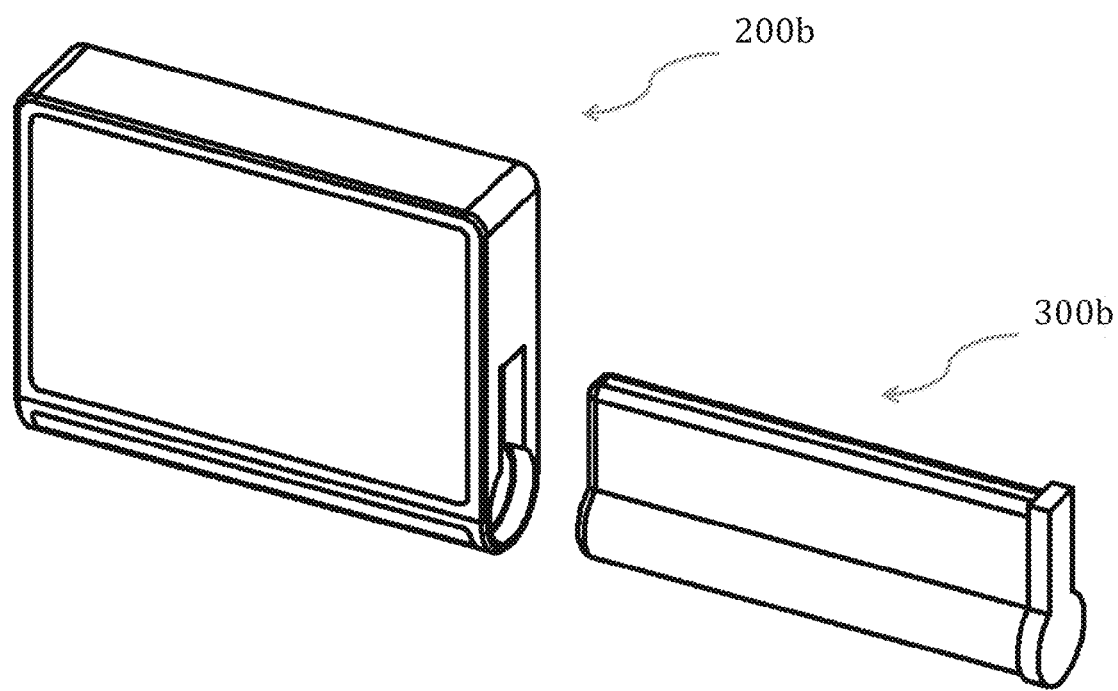

In yet another preferred embodiment of the invention, as shown in FIGS. 27A-27B, a drug delivery device 100b includes a delivery pump system 200b and a cartridge system 300b. The overall dimensions of the drug delivery device 100b are preferably 2.28" (length)×1.75" (width)×0.5" (thickness). In this embodiment, the drug delivery device 100b allows for insertion and removal of the cartridge system 300b laterally. The single degree of freedom of the cartridge system 300b allows for easier insertion of the cartridge system 300b to the delivery pump system 200b. The drug delivery device 100b has a plurality of windows that enable the user to view the medicament(s) and/or the various elements of the delivery pump system 200b and the cartridge system 300b. The delivery pump system 200b has a plurality of buttons on the side to navigate menus, administer medicament, review saved data, modify user settings, or input general information. The drug delivery device 100b can have a dual actuated system and direct infusion connection schemes.

Figure 28A:
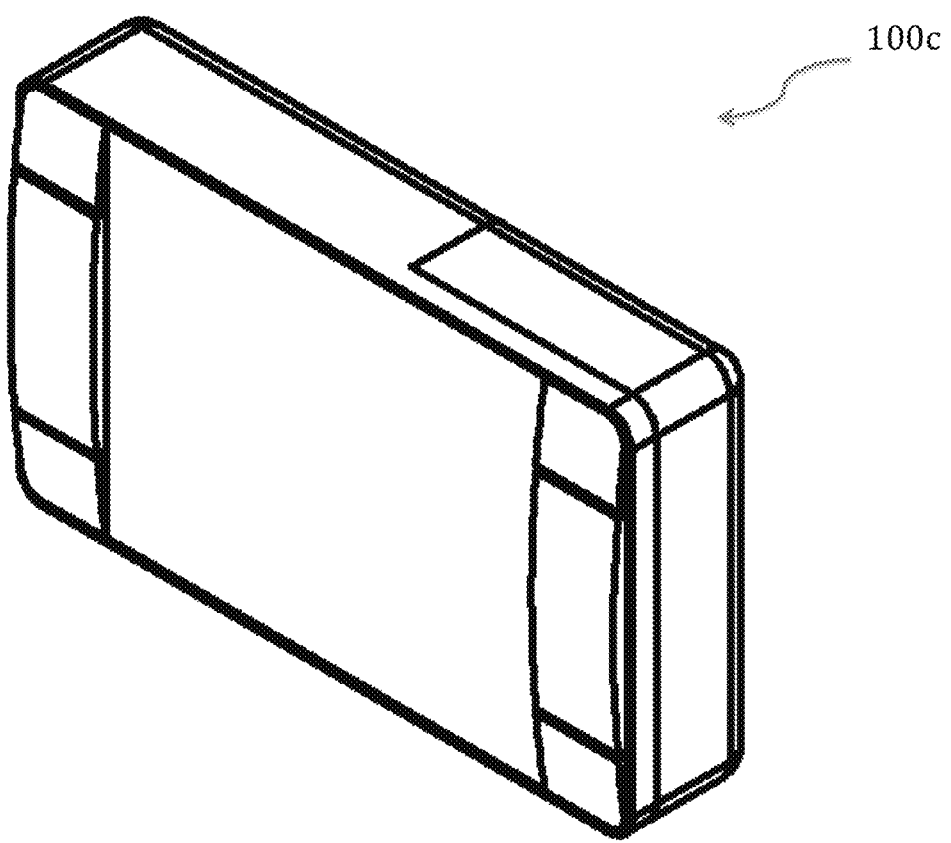
FIGS. 28A-28B illustrate a perspective view of a drug delivery device comprising a delivery pump system and a cartridge system in accordance with another embodiment of the present invention.
Figure 28B:
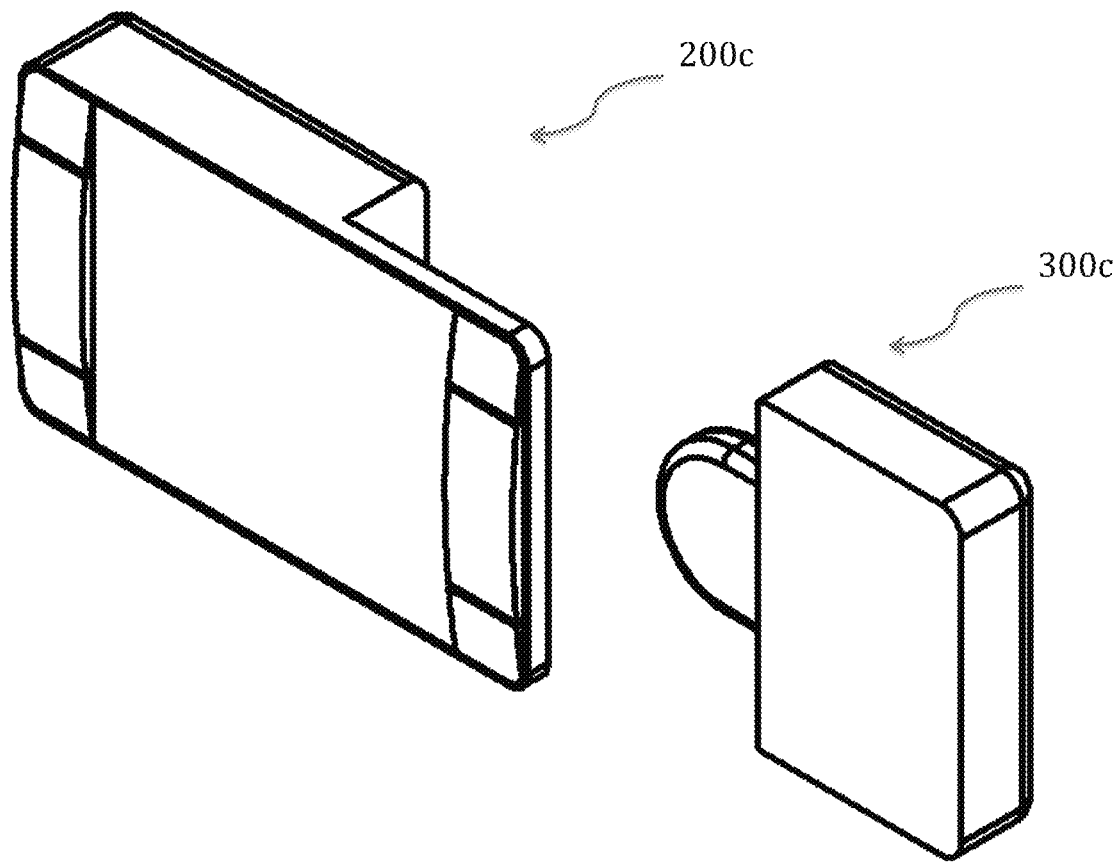

In another preferred embodiment of the invention, as shown in FIGS. 28A-28B, a drug delivery device 100c includes a delivery pump system 200c and a cartridge system 300c. The overall dimensions of the drug delivery device 100c are preferably 2.5" (length)×1.5" (width)×0.5" (thickness). In this embodiment, the drug delivery device 100c allows for insertion and removal of the cartridge system 300c in the rear. The single degree of freedom of the cartridge system 300c allows for easier insertion of the cartridge system 300c to the delivery pump system 200c. The delivery pump system 200c has a larger aspect ratio screen and a larger surface area for buttons to benefit visually impaired. Further, the drug delivery device 100c has a plurality of windows that enable the user to view the medicament(s) and/or the various elements of the delivery pump system 200c and the cartridge system 300c. The delivery pump system 200c has a plurality of buttons on the side to navigate menus, administer medicament, review saved data, modify user settings, or input general information. Additionally, the delivery pump system 200c has a storage area for storing a plurality of blood glucose test strips.

The preferred embodiments of the present invention shown in FIGS. 1-28 are related to insulin pumps and use by diabetic patients but it should be understood that the drug delivery device may have applications in other fields including, but not limited to, oncology and pain management. While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. A drug delivery device, comprising:
   a delivery pump system having a plurality of electromagnetic coils, a controller electrically coupled to the plurality of electromagnetic coils, and a power source; and
   a cartridge system, wherein the cartridge system includes:
      a first reservoir and a second reservoir, the first reservoir and the second reservoir each having a body with a top end and an opening formed in the top end;
      a first inlet/outlet member connected to the first reservoir, the first inlet/outlet member having a fluid receiving opening, a fluid discharge opening, and a fluid outlet component, the fluid receiving opening of the first inlet/outlet member in fluid communication with the first reservoir, and the fluid outlet component of the first inlet/outlet member in fluid communication with the fluid discharge opening of the first inlet/outlet member;
      a second inlet/outlet member connected the second reservoir, the second inlet/outlet member having a fluid receiving opening, a fluid discharge opening, and a fluid outlet component, the fluid receiving opening of the second inlet/outlet member in fluid communication with the second reservoir, and the fluid outlet component of the second inlet/outlet member in fluid communication with the fluid discharge opening of the second inlet/outlet member;
      a first pump body insert having a fluid receiving opening, a fluid discharge opening, a plurality of inlet channels, and a plurality of outlet channels, the fluid receiving opening of the first pump body insert in fluid communication with the plurality of inlet channels of the first pump body insert, the plurality of inlet channels of the first pump body insert in fluid communication with the plurality of outlet channels of the first pump body insert, and the plurality of outlet channels of the first pump body insert in fluid communication with the fluid discharge opening of the first pump body insert;
      a second pump body insert having a fluid receiving opening, a fluid discharge opening, a plurality of inlet channels, and a plurality of outlet channels, the fluid receiving opening of the second pump body insert in fluid communication with the plurality of inlet channels of the second pump body insert, the plurality of inlet channels of the second pump body insert in fluid communication with the plurality of outlet channels of the second pump body insert, and the plurality of outlet channels of the second pump body insert in fluid communication with the fluid discharge opening of the second pump body insert;

a pump membrane positioned between the first pump body insert and the second pump body insert; and a plurality of magnets, each of the plurality of magnets having a distal end, a proximal end, and a body extending between the distal and proximal ends, and at least one of the said proximal ends being in contact with the pump membrane, and at least one of the distal ends being housed within at least one of the said first and second pump body inserts, wherein the plurality of magnets and the plurality of electromagnetic coils are axially aligned, wherein the fluid receiving opening of the first pump body insert is in fluid communication with the fluid receiving opening of the first inlet/outlet member, and the fluid discharge opening of the first pump body insert is in fluid communication with the fluid discharge opening of the first inlet/outlet member, and wherein the fluid receiving opening of the second pump body insert is in fluid communication with the fluid receiving opening of the second inlet/outlet member, and the fluid discharge opening of the second pump body insert is in fluid communication with the fluid discharge opening of the second inlet/outlet member.

2. The device of claim 1, further comprising:

an infusion set having a conduit for delivery of medicament, the conduit having a distal end, a proximal end, and a body extending between the distal and proximal ends, wherein the distal end of the conduit is attached to a luer slip on the fluid outlet component of at least one of the first inlet/outlet member and the second inlet/outlet member, and wherein the proximal end of the conduit is connected to a cannula and an insertion mechanism.

3. The device of claim 2, wherein the cannula includes the insertion mechanism.

4. The device of claim 1, wherein the delivery pump system further comprises a blood glucose meter, the blood glucose meter being communicatively linked to the said controller, and the blood glucose meter having a port, wherein the port is capable of interacting with a blood glucose test strip, and the blood glucose meter is configured to compute a concentration of glucose based at least in part on the blood glucose test strip.

5. The device of claim 1, wherein the delivery pump system further comprises a plurality of membrane switches, the plurality of membrane switches being communicatively linked to the controller.

6. The device of claim 1, wherein the delivery pump system further comprises an input device, a display, and a backlight assembly, the backlight assembly being communicatively linked to the controller.

7. The device of claim 6, wherein the input device includes a touch screen.

8. The device of claim 1, wherein the delivery pump system further comprises a port, the port being communicatively linked to the controller and the port enabling the drug delivery device to communicate with a computer.

9. The device of claim 1, wherein the delivery pump system further comprises a front-top case and a rear-top case, the front-top case and the rear-top case being designed to form a housing.

10. The device of claim 1, wherein the cartridge system further comprises a plurality of reservoir shells and an insulation layer within at least one of the plurality of reservoir shells, wherein the first reservoir and the second reservoir are each mounted within one of the plurality of reservoir shells.

11. The device of claim 10, wherein the first reservoir and the second reservoir are mounted within the same reservoir shell.

12. The device of claim 10, wherein the first reservoir and the second reservoir are mounted within different reservoir shells.

13. The device of claim 1, wherein the first reservoir contains a first fluid medicament and the second reservoir contains a second fluid medicament.

14. The device of claim 13, wherein the first fluid medicament includes insulin, and the second fluid medicament includes glucagon.

15. The device of claim 1, further comprising a plurality of valve membranes, wherein each of the plurality of valve membranes is pre-stressed and made of silicone.

16. The device of claim 1, wherein the pump membrane is electromagnetically actuated and controlled by the controller using feedback control for delivery of medicament.

17. The device of claim 1, wherein the delivery pump system further comprises a continuous blood glucose sensor, the continuous blood glucose sensor being communicatively linked to the controller.

18. The device of claim 1, wherein the power source is rechargeable.

19. The device of claim 1, wherein at least one of the first reservoir and the second reservoir is pre-filled with at least one medicament.

20. The device of claim 1, wherein at least one of the first and the second reservoirs is refillable.

21. A method of delivering medicament using a drug delivery device, comprising:

loading a plurality of pre-filled reservoirs containing fluid medicament onto a cartridge system;

engaging the cartridge system and a delivery pump system;

selecting various one or more parameters using a user interface of the delivery pump system; and connecting an infusion set to the drug delivery device, wherein the drug delivery device includes plurality of electromagnetic coils, a controller electrically coupled to the plurality of electromagnetic coils, and a power source, wherein the cartridge system comprises:

a first reservoir and a second reservoir, the first reservoir and the second reservoir each having a body with a top end and an opening formed in the top end;

a first inlet/outlet member connected to the first reservoir, the first inlet/outlet member having a fluid receiving opening, a fluid discharge opening, and a fluid outlet component, the fluid receiving opening of the first inlet/outlet member in fluid communication with the first reservoir, and the fluid outlet component of the first inlet/outlet member in fluid communication with the fluid discharge opening of the first inlet/outlet member;

a second inlet/outlet member connected to the second reservoir, the second inlet/outlet member having a fluid receiving opening, a fluid discharge opening, and a fluid outlet component, the fluid receiving opening of the second inlet/outlet member in fluid communication with the second reservoir, and the fluid outlet component of the second inlet/outlet member in fluid communication with the fluid discharge opening of the second inlet/outlet member;

a first pump body insert having a fluid receiving opening, a fluid discharge opening, a plurality of inlet channels, and a plurality outlet channels, the fluid receiving opening of the first pump body insert in fluid communication with the plurality of inlet channels of the first pump body insert, the plurality of inlet channels of the first pump body insert in fluid communication with the plurality of outlet channels of the first pump body insert, and the plurality of outlet channels of the first pump body insert in fluid communication with the fluid discharge opening of the first pump body insert;

a second pump body insert having a fluid receiving opening, a fluid discharge opening, a plurality of inlet channels, and a plurality of outlet channels, the fluid receiving opening of the second pump body insert in fluid communication with the plurality of inlet channels of the second pump body insert, the plurality of inlet channels of the second pump body insert in fluid communication with the plurality of outlet channels of the second pump body insert, and the plurality of outlet channels of the second pump body insert in fluid communication with the fluid discharge opening of the second pump body insert;

a pump membrane positioned between the first pump body insert and the second pump body insert; and a plurality of magnets, each of the plurality of magnets having a distal end, a proximal end, and body extending between the distal and proximal ends, and at least one of the proximal ends being in contact with the pump membrane, and at least one of the distal ends being housed within at least one of the first and second pump body inserts, wherein the plurality of magnets and the plurality of electromagnetic coils are axially aligned, wherein the fluid receiving opening of the first pump body insert is in fluid communication with the fluid receiving opening of the first in inlet/outlet member, and the fluid discharge opening of the first pump body insert is in fluid communication with the fluid discharge opening of the first inlet/outlet member, and wherein the fluid receiving opening of the second pump body insert is in fluid communication with the fluid receiving opening of the second inlet/outlet member, and the fluid discharge opening of the second pump body insert is in fluid communication with the fluid discharge opening of the second inlet/outlet member.

22. The method of claim 21, further comprising: placing an inset of the infusion set on a body part of a patient; attaching the infusion set to the patient's body; connecting the infusion set to the drug delivery device; and turning on the drug delivery device.

23. The method of claim 21, further comprising:

using a glucose meter to determine a patient's blood glucose level;

transmitting blood glucose data to a controller within the delivery pump system; and determining a rate of delivery of the fluid medicament based at least in part on the blood glucose data.

* * * * *

UNITED STATES PATENT AND TRADEMARK OFFICE
CERTIFICATE OF CORRECTION

PATENT NO.        : 8,790,307 B2
APPLICATION NO.   : 13/370091
DATED             : July 29, 2014
INVENTOR(S)       : Amirouche et al.

Page 1 of 1

It is certified that error appears in the above-identified patent and that said Letters Patent is hereby corrected as shown below:

In the Claims

Claim 1, col. 18, lines 39-40, "connected the second reservoir" should read -- connected to the second reservoir --.

Claim 1, col. 19, line 9, "one of the said proximal ends" should read -- one of the proximal ends --.

Claim 21, col. 20, line 37, "selecting various one or more parameters" should read -- selecting one or more parameters --.

Signed and Sealed this
Twenty-first Day of October, 2014

Michelle K. Lee
*Deputy Director of the United States Patent and Trademark Office*